United States Patent
Quibell

(10) Patent No.: US 7,132,449 B2
(45) Date of Patent: Nov. 7, 2006

(54) INHIBITORS OF CRUZIPAIN AND OTHER CYSTEINE PROTEASES

(75) Inventor: Martin Quibell, Cambridge (GB)

(73) Assignee: Amura Therapeutics Limited, Cambridge (GB)

( * ) Notice: Subject to any disclaimer, the term of this patent is extended or adjusted under 35 U.S.C. 154(b) by 420 days.

(21) Appl. No.: 10/466,355

(22) PCT Filed: Jan. 7, 2002

(86) PCT No.: PCT/GB02/00188

§ 371 (c)(1),
(2), (4) Date: Jan. 8, 2004

(87) PCT Pub. No.: WO02/057248

PCT Pub. Date: Jul. 25, 2002

(65) Prior Publication Data

US 2004/0127424 A1 Jul. 1, 2004

Related U.S. Application Data

(60) Provisional application No. 60/275,360, filed on Mar. 13, 2001.

(30) Foreign Application Priority Data

Jan. 17, 2001 (GB) .................. 0101177.4

(51) Int. Cl.
*A61K 31/34* (2006.01)
*C07D 307/02* (2006.01)
(52) U.S. Cl. ..................... 514/473; 549/475
(58) Field of Classification Search ............... 514/473; 549/475
See application file for complete search history.

(56) References Cited

U.S. PATENT DOCUMENTS

| 3,652,574 A | 3/1972 | Garmaise ................... 260/296 |
| 6,841,571 B1* | 1/2005 | Bekkali et al. ............. 514/473 |
| 6,894,074 B1* | 5/2005 | Bretschneider et al. ..... 514/462 |
| 6,984,662 B1* | 1/2006 | Cottrell et al. .............. 514/471 |
| 7,008,666 B1* | 3/2006 | Ahotupa et al. ............ 426/648 |
| 7,026,353 B1* | 4/2006 | Kjelleberg et al. .......... 514/473 |

FOREIGN PATENT DOCUMENTS

| WO | 98/05336 | 2/1998 |
| WO | 98/08802 | 3/1998 |
| WO | 98/28268 | 7/1998 |
| WO | 98/50533 | 11/1998 |
| WO | 99/53039 | 10/1999 |
| WO | 00/29408 | 5/2000 |
| WO | 00/69855 | 11/2000 |
| WO | 02/040462 | 5/2002 |
| WO | 02/051983 | 7/2002 |

OTHER PUBLICATIONS

Fenwick, et al., "Diastereoselective Synthesis, Activity and Chiral Stability of Cyclic Alkoxyketone Inhibitors of Cathepsin K," *Bioorganic & Medicinal Chemistry Letters*, vol. 11, pp. 199-202 (2001).

Marquis, et al., "Conformationally Constrained 1, 3-Diamino Ketones: A Series of Potent Inhibitors of the Cysteine Protease Cathepsin K," *J. Med. Chem.*, vol. 41, pp. 3563-3567 (1998).

* cited by examiner

*Primary Examiner*—Deborah C. Lambkin
(74) *Attorney, Agent, or Firm*—Edwards Angell Palmer & Dodge; Kathleen M. Williams; Jeffrey L. Kopacz

(57) ABSTRACT

Compounds of general formula (I):

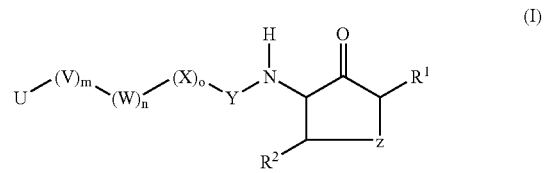

wherein $R^1$, $R^2$, Y, $(X)_o$, $(W)_n$, $(V)_m$, Z and U are as defined in the specification, are inhibitors of cruzipain and other cysteine protease inhibitors and are useful as therapeutic agents, for example in Chagas' disease, or for validating therapeutic target compounds.

35 Claims, No Drawings

INHIBITORS OF CRUZIPAIN AND OTHER CYSTEINE PROTEASES

THIS INVENTION relates to compounds which are inhibitors of the protease cruzipain, a gene product of the Trypanosoma cruzi parasite. In particular, the invention provides compounds that are useful for the therapeutic treatment of Trypanosoma cruzi infection, to the use of these compounds, and to pharmaceutical compositions comprising them. Furthermore, this invention relates to compounds which are inhibitors across a broad range of cysteine proteases, to the use of these compounds, and to pharmaceutical compositions comprising them. Such compounds are useful for the therapeutic treatment of diseases in which participation of a cysteine protease is implicated.

The trypanosomal family of parasites have a substantial worldwide impact on human and animal healthcare (McKerrow, J. H., et al, Ann. Rev. Microbiol. 47, 821–853, 1993). One parasite of this family, Trypanosoma cruzi, is the causative agent of Chagas' disease, which affects in excess of twenty million people annually in Latin and South America, is the leading cause of heart disease in these regions and results in more than 45,000 deaths per annum (Centers for Disease Control and prevention website). In addition, with the increase in migration of the infected population from rural to urban sites and movements from South and Central America into North America, the infection is spreading via blood transfusions, and at birth. The present treatments of choice for Trypanosoma cruzi infection, nifurtimox and benznidazole (an NADH fumarate reductase inhibitor, Turrens, J F, et al, Mol Biochem Parasitol., 82(1), 125–9, 1996) are at best moderately successful, achieving ~60% cure during the acute phase of infection (see Docampo, R. Curr. Pharm. Design, 7, 1157–1164, 2001 for a general discussion) whilst not being prescribed at all during the chronic phase where cardiomyopathy associated heart failure often occurs (Kirchhoff, L. V. New Engl. J. Med., 329, 639–644, 1993). Additionally, these two drugs have serious adverse toxic effects, requiring close medical supervision during treatment, and have been shown to induce chromosomal damage in chagastic infants (Gorla, N. B. et al, Mutat. Res. 206, 217–220, 1988). Therefore, a strong medical need exists for new effective drugs for the chemotherapeutic treatment of Trypanosoma cruzi infection.

Classically, the identification of enzymes found to be crucial for the establishment or propagation of an infectious disease has been instrumental in the development of successful drugs such as antivirals (e.g. HIV aspartyl protease inhibitors) and anti-bacterials (e.g. β-lactam antibiotics). The search for a similar Achilles heel in parasitic infections has examined numerous enzymes (e.g. parasitic dihydrofolate reductase, see Chowdhury, S. F. et al, J. Med. Chem., 42(21), 4300–4312, 1999; trypanothione reductase, see Li, Z. et al, Bioorg. Med. Chem. Lett., 11(2), 251–254, 2001; parasitic glyceraldehydes-3-phosphate dehydrogenase, see Aranov, A. M. et al, J. Med. Chem., 41(24), 4790–4799, 1998). A particularly promising area of research has identified the role of cysteine proteases, encoded by the parasite, that play a pivotal role during the life cycle of the parasite (McKerrow, J. H., et al, Bioorg. Med. Chem., 7, 639–644, 1999). Proteases form a substantial group of biological molecules which to date constitute approximately 2% of all the gene products identified following analysis of several genome sequencing programmes (e.g. see Southan, C. J. Pept. Sci, 6, 453–458, 2000). Proteases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which aligns the bond for cleavage precisely within the protease catalytic site. Catalytic hydrolysis then commences through nucleophilic attack of the amide bond to be cleaved either via an amino acid side-chain of the protease itself, or through the action of a water molecule that is bound to and activated by the protease. Proteases in which the attacking nucleophile is the thiol side-chain of a Cys residue are known as cysteine proteases. The general classification of 'cysteine protease' contains many members found across a wide range of organisms from viruses, bacteria, protozoa, plants and fungi to mammals.

Biological investigation of Trypanosoma cruzi infection has highlighted a number of specific enzymes that are crucial for the progression of the parasite's life cycle. One such enzyme, cruzipain, a cathepsin L-like cysteine protease, is a clear therapeutic target for the treatment of Chagas' disease ((a) Cazzulo, J. J. et al, Curr. Pharm. Des. 7, 1143–1156, 2001; (b) Caffrey, C. R. et al, Curr. Drug Targets, 1, 155–162, 2000). Although the precise biological role of cruzipain within the parasite's life cycle remains unclear, elevated cruzipain messenger RNA levels in the epimastigote developmental stage indicate a role in the nutritional degradation of host-molecules in lysosomal-like vesicles (Engel, J. C. et al, J. Cell. Sci, 1597–606, 1998). The validation of cruzipain as a viable therapeutic target has been achieved with increasing levels of complexity. Addition of a general cysteine protease inhibitor, Z-Phe-Ala-FMK to Trypanosoma cruzi-infected mammalian cell cultures blocked replication and differentiation of the parasite, thus arresting the parasite life cycle (Harth, G., et al, Mol. Biochem. Parasitol. 58, 17–24, 1993). Administration of a vinyl sulphone-based inhibitor in a Trypanosoma cruzi-infected murine animal model not only rescued the mice from lethal infections, but also produced a complete recovery (Engel, J. C. et al, J. Exp. Med, 188(4), 725–734, 1998). Numerous other in vivo studies have confirmed that infections with alternative parasites such as Leishmania major (Selzer, P. M. et al, Proc. Nat'l. Acad. Sci. U.S.A., 96, 11015–11022, 1999), Schistosoma mansoni and Plasmodium falciparium (Olson, J. E. et al, Bioorg. Med. Chem., 7, 633–638, 1999) can be halted or cured by treatment with cysteine protease inhibitors.

A variety of synthetic approaches have been described towards the design of cruzipain inhibitors. However, although providing a biological 'proof-of-principle' for the treatment of Trypanosoma cruzi infection, current inhibitors exhibit a number of biochemical and physical properties that may preclude their clinical development. (e.g. see (a) Brinen, L. S. et al, Structure, 8, 831–840, 2000, peptidomimetic vinyl sulphones, possible adverse mammalian cell toxicity (see McKerrow, J. H. and Engel, J. unpublished results cited in Scheidt, K. A. et al, Bioorg. Med. Chem, 6, 2477–2494, 1998); (b) Du, X. et al, Chem. Biol., 7, 733–742, 2000, aryl ureas, generally with low μM activity, and high ClogP values, thus poor aqueous solubility and probably low oral bioavailability; (c) Roush, W. R. et al, Tetrahedron, 56, 9747–9762, 2000, peptidyl epoxysuccinates, irreversible inhibitors, with potent activity verses house-keeping mammalian proteases such as cathepsin B; (d) Li, R. et al, Bioorg. Med. Chem. 4(9), 1421–1427, 1996, bisarylacylhydrazides and chalcones, polyhydroxylated aromatics; (e) U.S. Pat. No. 6,143,931, WO 9846559, non-peptide α-ketoamides). Of the many different approaches to enzyme inhibition to date, only the cruzipain protease inhibitors have proven effective in curing disease-related animal models of *Trypanosoma cruzi* infection. Therefore, a clear medical need exists to progress these 'proof-of-principle' findings towards clinical candidates, suitable for human use, through the discovery of more efficacious cruzipain inhibitors that have a desirable combination of potency, selectivity, low toxicity and optimised pharmacokinetic parameters.

Cruzipain and indeed many other crucial parasitic proteases belong to the papain-like CA C1 family and have close structural mammalian homologues. Cysteine proteases are classified into 'clans' based upon a similarity in the three-dimensional structure or a conserved arrangement of catalytic residues within the protease primary sequence. Additionally, 'clans' are further classified into 'families' in which each protease shares a statistically significant relationship with other members when comparing the portions of amino acid sequence which constitute the parts responsible for the protease activity (see Barrett, A. J. et al, in 'Handbook of Proteolytic Enzymes', Eds. Barrett, A. J., Rawlings, N. D., and Woessner, J. F. Publ. Academic Press, 1998, for a thorough discussion). To date, cysteine proteases have been classified into five clans, CA, CB, CC, CD and CE (Barrett, A. J. et al 1998). A protease from the tropical papaya fruit 'papain' forms the foundation of clan CA, which currently contains over 80 distinct and complete entries in various sequence databases, with many more expected from the current genome sequencing efforts. Proteases of clan CA/family C1 have been implicated in a multitude of disease processes e.g. human proteases such as cathepsin K (osteoporosis), cathepsin S (autoimmune disorders), cathepsin L (metastases) or parasitic proteases such as falcipain (malaria parasite *Plasmodium falciparum*), cruzipain (*Trypanosoma cruzi* infection). Recently a bacterial protease, staphylopain (*S. aureus* infection) has also been tentatively assigned to clan CA. X-ray crystallographic structures are available for a range of the above mentioned proteases in complex with a range of inhibitors e.g. papain (PDB entries, 1pad, 1pe6, 1pip, 1pop, 4pad, 5pad, 6pad, 1ppp, 1the, 1csb, 1huc), cathepsin K (1au0, 1au2, 1au3, 1au4, 1atk, 1mem, 1bgo, 1ayw, 1ayu), cathepsin L (1cs8), cathepsin S (currently on-hold, but published McGrath, M. E. et al, *Protein Science*, 7, 1294–1302, 1998), cruzain (a recombinant form of cruzipain see Ealdn, A. E. et al, 268(9), 6115–6118, 1993) (1ewp, 1aim, 2aim, 1F29, 1F2A, 1F2B, 1F2C), staphylopain (1cv8). Each of the structures displays a similar overall active-site topology, as would be expected by their 'clan' and 'family' classification and such structural similarity exemplifies one aspect of the difficulties involved in discovering a selective inhibitor of cruzipain suitable for human use. However, subtle differences in terms of the depth and intricate shape of the active site groove of each CA C1 protease are evident, which may be exploited for selective inhibitor design. Additionally, many of the current substrate-based inhibitor complexes of CA C1 family proteases show a series of conserved hydrogen bonds between the inhibitor and the protease backbone, which contribute significantly to inhibitor potency. Primarily a bidentate hydrogen-bond is observed between the protease Gly66 (C=O)/inhibitor N—H and the protease Gly66(NH)/inhibitor (C=O), where the inhibitor (C=O) and (NH) are provided by an amino acid residue N̲H̲C̲H̲R̲C̲O̲ that constitutes the S2 sub-site binding element within the inhibitor (see Berger, A. and Schecter, I. *Philos. Trans. R. Soc. Lond. [Biol.]*, 257, 249–264, 1970 for a description of protease binding site nomenclature). A further hydrogen-bond between the protease main-chain (C=O) of asparagine or aspartic acid (158 to 163, residue number varies between proteases) and an inhibitor (N—H) is often observed, where the inhibitor (N—H) is provided by the S1 sub-site binding element within the inhibitor. Thus, the motif X—N̲H̲CHR C̲O̲—NH—Y is widely observed amongst the prior art substrate-based inhibitors of CA C1 proteases.

In the prior art, the development of cysteine protease inhibitors for human use has recently been an area of intense activity. Considering the CA C1 family members, particular emphasis has been placed upon the development of inhibitors of human cathepsins, primarily cathepsin K (osteoporosis), cathepsin S (autoimmune disorders) and cathepsin L (metastases), through the use of peptide and peptidomimetic nitriles (e.g. see WO-A-0109910, WO-A-0051998, WO-A-0119816, WO-A-9924460, WO-A-0049008, WO-A-0048992, WO-A-0049007, WO-A-0130772, WO-A-0055125, WO-A-0055126, WO-A-0119808, WO-A-0149288, WO-A-0147886), linear and cyclic peptide and peptidomimetic ketones (e.g. see Veber, D. F. and Thompson, S. K., *Curr. Opin. Drug Discovery Dev.*, 3(4), 362–369, 2000, WO-A-0170232, WO-A-0178734, WO-A-0009653, WO-A-0069855, WO-A-0029408, WO-A-0134153 to WO-A-0134160, WO-A-0029408, WO-A-9964399, WO-A-9805336, WO-A-9850533), ketoheterocycles (e.g. see WO-A-0055144, WO-A-0055124) and monobactams (e.g. see WO-A-0059881, WO-A-9948911, WO-A-0109169). The prior art describes potent in vitro inhibitors, but also highlights the many difficulties in developing a human therapeutic. For example, WO-A-9850533 and WO-A-0029408 describe compounds that may be referred to as cyclic ketones and are inhibitors of cysteine proteases with a particular reference towards papain family proteases and as a most preferred embodiment, cathepsin K. WO-A-9850533 describes compounds subsequently detailed in the literature as potent inhibitors of cathepsin K with good oral bioavailability (Witherington, J., 'Tetrahydrofurans as Selective Cathepsin K Inhibitors', RSC meeting, Burlington House, London, 1999). The compounds of WO-A-9850533 were reported to bind to cathepsin K through the formation of a reversible covalent bond between the tetrahydrofuran carbonyl and the active site catalytic cysteine residue (Witherington, J., 1999). Additionally, the same cyclic ketone compounds are described in WO-A-9953039 as part of a wide-ranging description of inhibitors of cysteine proteases associated with parasitic diseases, with particular reference to the treatment of malaria by inhibition of falcipain. However, subsequent literature describes the cyclic ketone compounds of WO-A-9850533 to be unsuitable for further development or for full pharmacokinetic evaluation due to a physiochemical property of the inhibitors, the poor chiral stability of the α-aminoketone chiral centre (Marquis, R. W. et al, *J. Med. Chem.*, 44(5), 725–736, 2001). WO-A-0069855 describes compounds that may also be referred to as cyclic ketones with particular reference towards inhibition of cathepsin S. The compounds of WO-A-0069855 are considered to be an advance on compounds of WO-A-9850533 due to the presence of the β-substituent on the cyclic ketone ring system that provides chiral stability to the α-carbon of the cyclic ketone ring system. However, the compounds of WO-A-0069855 and indeed those of WO-A-9850533 describe an absolute requirement for the presence of an amino acid substituent $R^1R^2$N̲H̲CHR$^3$C̲O̲— that provides the N-terminal portion of the inhibitor molecules, i.e. contain the potential hydrogen-bonding motif X—N̲H̲CHR C̲O̲—NH—Y that is widely observed amongst the prior art substrate-based inhibitors of CA C1 proteases. Although the number of amino acids described both in the literature and commercially available constitute many hundreds of possibilities, in many instances an amino acid backbone may not provide the appropriate balance of properties required for further inhibitor development.

It has now been discovered that certain compounds, defined by general formula (I), are potent and selective cruzipain protease inhibitors which are useful in the treatment of *Trypanosoma cruzi* infection. Other compounds defined by general formula (I) are protease inhibitors across a broad range of CA C1 cysteine proteases and compounds useful in the treatment of diseases caused by cysteine proteases. Compounds described by general formula (I) do not contain the X—NHCHRCO—NH—Y motif that is widely observed amongst the prior art substrate-based inhibitors of CA C1 proteases, yet surprisingly compounds defined by general formula (I) retain good potency. The present invention provides substituted (2-alkyl-4-oxo-tetrahydrofuran-3-yl)amide, (2-alkyl-4-oxo-tetrahydrothiophen-3-yl) amide and (2-alkyl-5-oxocyclopentyl) amide compounds defined by general formula (I).

Accordingly, the first aspect of the invention provides a compound according to general formula (I):

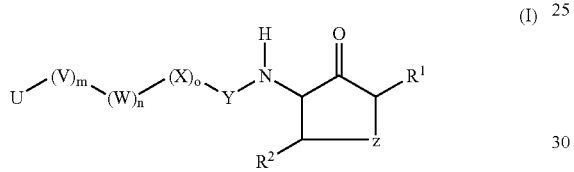

wherein: $R^1=C_{0-7}$-alkyl (when C=0, $R^1$ is simply hydrogen), $C_{3-6}$-cycloalkyl or
Ar—$C_{0-7}$-alkyl (when C=0, $R^1$ is simply an aromatic moiety Ar);
$R^2=C_{1-7}$-alkyl, $C_{3-6}$-cycloalkyl or Ar—$C_{0-7}$-alkyl;
Y=CHR$^3$—CO or CR$^3$R$^4$—CO where R$^3$ and R$^4$ are independently chosen from $C_{0-7}$-alkyl, $C_{3-6}$-cycloalkyl and Ar—$C_{0-7}$-alkyl, or Y represents

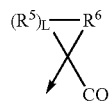

where L is a number from one to four and $R^5$ and $R^6$ are independently chosen from CR$^7$R$^8$ where $R^7$ and $R^8$ are independently chosen from $C_{0-7}$-alkyl, $C_{3-6}$-cycloalkyl, Ar—$C_{0-7}$-alkyl or halogen; and for each $R^5$ and $R^6$ either $R^7$ or $R^8$ (but not both $R^7$ and $R^8$) may additionally be chosen from O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N—($C_{0-7}$-alkyl)$_2$, N—($C_{3-6}$-cycloalkyl)$_2$, and N—(Ar—$C_{0-7}$-alkyl)$_2$;
$(X)_o$=CR$^9$R$^{10}$, where R$^9$ and R$^{10}$ are independently chosen from $C_{0-7}$-alkyl, $C_{3-6}$-cycloalkyl and Ar—$C_{0-7}$-alkyl and o is a number from zero to three;
$(W)_n$=O, S, C(O), S(O) or S(O)$_2$ or, when o is one or greater, NR$^{11}$, where R$^{11}$ is chosen from $C_{0-7}$-alkyl, $C_{3-6}$-cycloalkyl and Ar—$C_{0-7}$-alkyl and n is zero or one;

$(V)_m$=C(O), C(S), S(O), S(O)$_2$, S(O)$_2$NH, OC(O), NHC(O), NHS(O), NHS(O)$_2$, OC(O)NH, C(O)NH or CR$^{12}$R$^{13}$, where R$^{12}$ and R$^{13}$ are independently chosen from $C_{0-7}$-alkyl, $C_{3-6}$-cycloalkyl, Ar—$C_{0-7}$-alkyl and m is a number from zero to three, provided that when m is greater than one, $(V)_m$ contains a maximum of one carbonyl or sulphonyl group;

Z=O (in which case compounds of general formula (I) may be named as (2-alkyl-4-oxo-tetrahydrofuran-3-yl) amides), S (in which case compounds of general formula (I) may be named as (2-alkyl-4-oxo-tetrahydrothiophen-3-yl)amides), or CH$_2$ (in which case compounds of general formula (I) may be named as (2-alkyl-5-oxocyclopentyl) amides);

U=a stable 5- to 7-membered monocyclic or a stable 8- to 11-membered bicyclic ring which is either saturated or unsaturated and which includes zero to four heteroatoms (as detailed below):

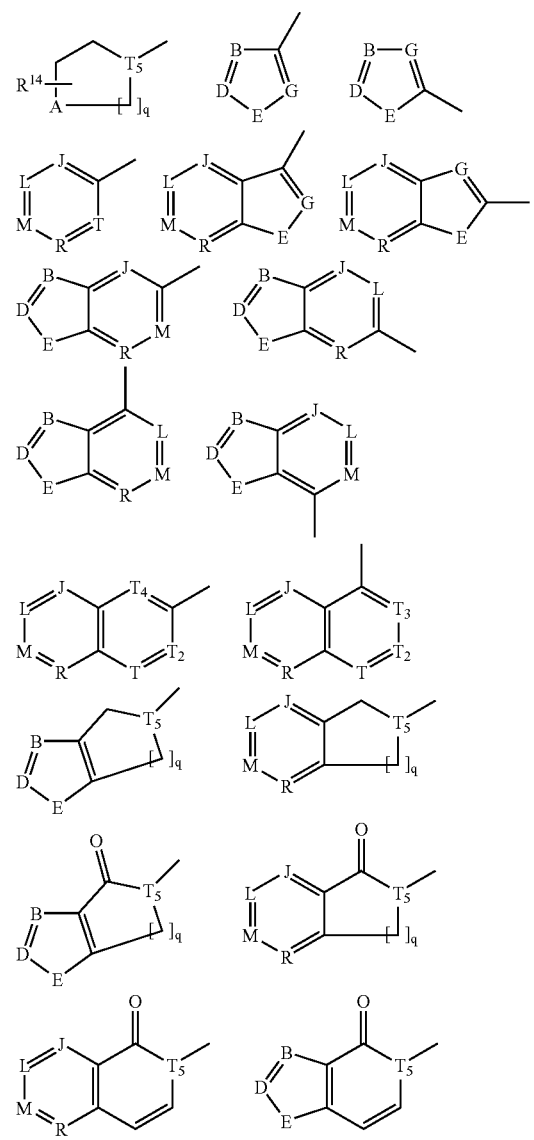

-continued

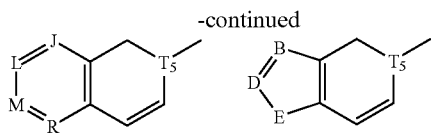

wherein $R^{14}$ is chosen from:
$C_{0-7}$-alkyl, $C_{3-6}$-cycloalkyl, Ar—$C_{0-7}$-alkyl, halogen, O—$C_{0-7}$-alkyl, O—$C_{3-6}$-cycloalkyl, O—Ar—$C_{0-7}$-alkyl, S—$C_{0-7}$-alkyl, S—$C_{3-4}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N—($C_{0-7}$-alkyl)$_2$, N—($C_{3-6}$-cycloalkyl)$_2$ and N—(Ar—$C_{0-7}$-alkyl)$_2$;

A is chosen from:
$CH_2$, $CHR^{14}$, O, S and $NR^{15}$, where $R^{14}$ is as defined above and where $R^{15}$ is chosen from $C_{0-7}$alkyl, $C_{3-6}$-cycloalkyl and Ar—$C_{0-7}$-alkyl;

B, D and G are independently chosen from:
$CR^{14}$, where $R^{14}$ is as defined above, or N;

E is chosen from:
$CH_2$, $CHR^{14}$, O, S and $NR^{15}$, where $R^{14}$ and $R^{15}$ are defined as above;

J, L, M, R, T, $T_2$, $T_3$ and $T_4$ are independently chosen from:
$CR^{14}$ and N, where $R^{14}$ is as defined above;

$T_5$ is chosen from:
CH or, only when $m+n+o \geq 1$, $T_5$ may additionally be N;

q is a number from one to three, thereby defining a 5-, 6- or 7-membered ring.

B, D, G, J, L, M, R, T, $T_2$, $T_3$ and $T_4$ may additionally represent an N-oxide (N→O).

The present invention includes all salts, hydrates, solvates, complexes and prodrugs of the compounds of this invention. The term "compound" is intended to include all such salts, hydrates, solvates, complexes and prodrugs, unless the context requires otherwise.

Appropriate pharmaceutically and veterinarily acceptable salts of the compounds of general formula (I) include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Salts which are not pharmaceutically or veterinarily acceptable may still be valuable as intermediates.

Prodrugs are any covalently bonded compounds which release the active parent drug according to general formula (I) in vivo. A prodrug may for example constitute an acetal or hemiacetal derivative of the exocyclic ketone functionality present in the (2-alkyl-4-oxo-tetrahydrofuran-3-yl) amide, (2-alkyl-4-oxo-tetrahydrothiophen-3-yl) amide and (2-alkyl-5-oxocyclopentyl)amide scaffold. If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

'Halogen' as applied herein is meant to include F, Cl, Br, I;

'Heteroatom' as applied herein is meant to include O, S and N;

'$C_{0-7}$-alkyl' as applied herein is meant to include stable straight and branched chain aliphatic carbon chains containing zero (i.e. simply hydrogen) to seven carbon atoms such as methyl, ethyl, n-propyl, isopropyl, n-butyl, isobutyl, t-butyl, pentyl, isopentyl, hexyl, heptyl and any simple isomers thereof. Additionally, any $C_{0-7}$-alkyl may optionally be substituted at any point by one, two or three halogen atoms (as defined above) for example to give a trifluoromethyl substituent. Furthermore, $C_{0-7}$-alkyl may contain one or more heteroatoms (as defined above) for example to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. A heteroatom or halogen is only present when $C_{0-7}$-alkyl contains a minimum of one carbon atom.

$C_{1-7}$-alkyl as applied herein is meant to include the definitions for $C_{0-7}$-alkyl (as defined above) but describes a substituent that comprises a minimum of one carbon.

'$C_{3-6}$-cycloalkyl' as applied herein is meant to include any variation of '$C_{0-7}$-alkyl' which additionally contains a carbocyclic ring such as cyclopropyl, cyclobutyl, cyclopentyl, cyclohexyl. The carbocyclic ring may optionally be substituted with one or more halogens (as defined above) or heteroatoms (as defined above) for example to give a tetrahydrofuran, pyrrolidine, piperidine, piperazine or morpholine substituent.

'Ar—$C_{0-7}$-alkyl' as applied herein is meant to include any variation of $C_{0-7}$-alkyl which additionally contains an aromatic ring moiety 'Ar'. The aromatic ring moiety Ar can be a stable 5 or 6-membered monocyclic or a stable 9 or 10 membered bicyclic ring which is unsaturated, as defined previously for U in general formula (I). The aromatic ring moiety Ar may be substituted by $R^{14}$ (as defined above for U in general formula (I)). When C=0 in the substituent Ar—$C_{0-7}$-alkyl, the substituent is simply the aromatic ring moiety Ar.

Other expressions containing terms such as alkyl and cycloalkyl are intended to be construed according to the definitions above. For example "$C_{1-4}$ alkyl" is the same as $C_{0-7}$-alkyl except that it contains from one to four carbon atoms.

If different structural isomers are present, and/or one or more chiral centres are present, all isomeric forms are intended to be covered. Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3$^{rd}$ edition, ed. March, J., John Wiley and Sons, New York, 1985).

Preferred compounds of general formula (I) include those in which $R^1$ comprises $C_{0-7}$-alkyl or Ar—$C_{0-7}$-alkyl. Thus, for example, preferred $R^1$ moieties include hydrogen, or a straight or branched alkyl chain, or a straight or branched heteroalkyl chain, or an optionally substituted arylalkyl chain, or an optionally substituted arylheteroalkyl chain.

It is particularly preferred that $R^1$ is hydrogen or $C_{1-4}$ alkyl or Ar—$C_{1-4}$-alkyl and examples of such $R^1$ substituents include, but are not limited to:

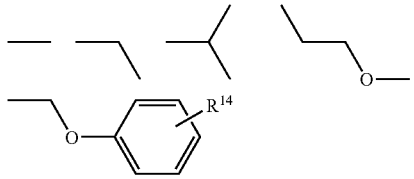

It is preferred that $R^2$ is $C_{1-7}$-alkyl or Ar—$C_{0-7}$-alkyl, for example, straight or branched alkyl chains or heteroalkyl chains or optionally substituted aralkyl chains or an alkyl-carboxylic ester chain or an N-(alkylcarbonyl)sulphonamide chain or an alkyl carboxamide chain.

Particularly preferred compounds include those in which $R^2$ is $C_{1-4}$-alkyl or Ar—$C_{1-4}$-alkyl and examples of such $R^2$ substituents include, but are not limited to:

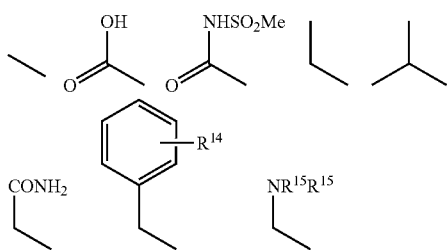

wherein $R^{14}$ and $R^{15}$ are as defined previously.

Additionally, preferred compounds of general formula (I) comprise those in which Z='O'.

Combining the preferred examples of the substituents $R^1$ and $R^2$ with an exemplary (2-alkyl-4-oxo-tetrahydrofuran-3-yl)amide scaffold yields the following compounds, which are among those preferred:

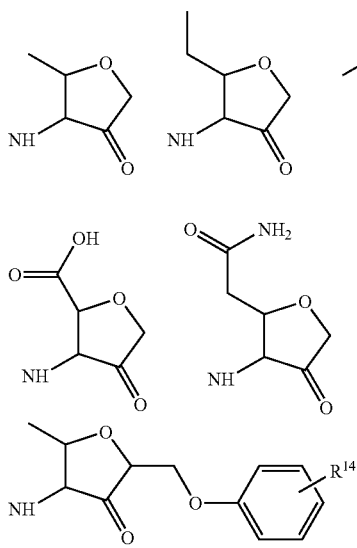

-continued

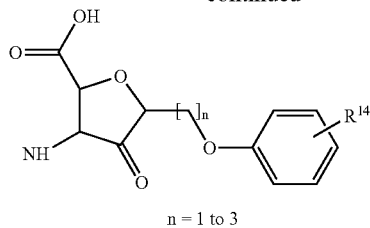

n = 1 to 3

In preferred compounds of general formula (I), Y is $CHR^4CO$ where $R^4$ is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted aryl-heteroalkyl chain. Additionally in preferred compounds of general formula (I), $R^4$ is selected from $C_{3-6}$-cycloalkyl, for example cyclohexylmethyl or cyclopentylmethyl.

Other preferred compounds of general formula (I) are those in which Y comprises a group:

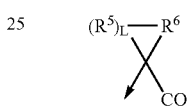

where $R^5$ and $R^6$ are each $CR^7R^8$ and each $R^7$ and $R^8$ is, independently, selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted arylheteroalkyl chain.

More preferred $R^7$ and $R^8$ groups include $C_{0-4}$ alkyl, for example hydrogen, methyl and ethyl.

Examples of preferred Y substituents include the following:

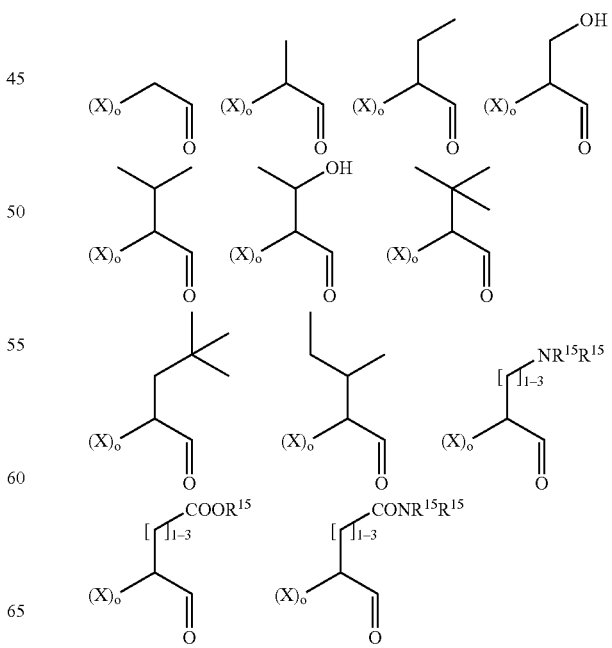

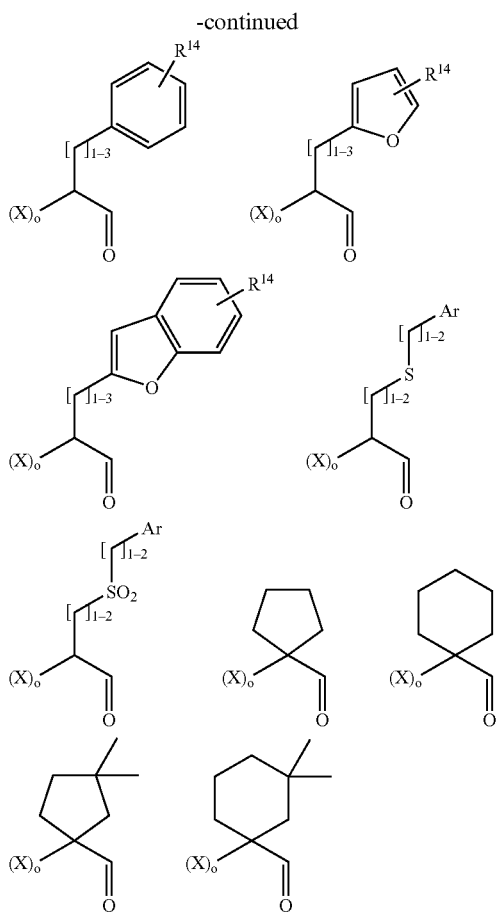

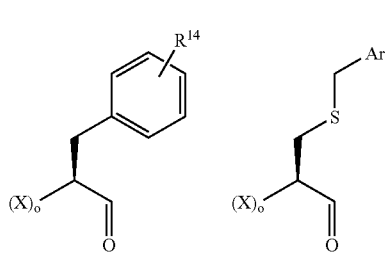

wherein R[14] and R[15] and Ar are as defined previously.

More preferred compounds of general formula (I), comprise an R[4] group chosen from $C_{1-4}$-alkyl, which may be substituted with OH, NR[15]R[15], COOR[15], or CONR[15]; or Ar—$C_{1-4}$-alkyl, where the aryl group may be substituted with R[14]; wherein each R[14] and R[15] is independently as defined above.

Even more preferred R[4] groups comprise Ar—CH$_2$—, where the aromatic ring is an optionally substituted phenyl or monocyclic heterocycle Additionally, even more preferred R[4] groups comprise simple branched alkyl groups such as isobutyl or straight heteroalkyl chains such as benzylsulfanylmethyl or benzylsulphonylmethyl. Furthermore, even more preferred R[4] groups comprise cyclohexylmethyl. Examples of even more preferred Y substituents comprise the following, wherein R[14] and Ar are as defined previously It is preferred that in the group (X)$_o$, each of R[9] and R[10] is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted arylheteroalkyl chain.

More preferred (X)$_o$ groups comprise R[9] chosen from hydrogen; R[10] is $C_{1-4}$-alkyl, which may be substituted with OH, NR[15]R[15], COOR[15], or CONR[15]; or Ar—$C_{1-4}$-alkyl, where the aryl group may be substituted with R[14], wherein each R[14] and R[15] is independently as defined above.

Examples of preferred (X)$_o$ groups include the following:

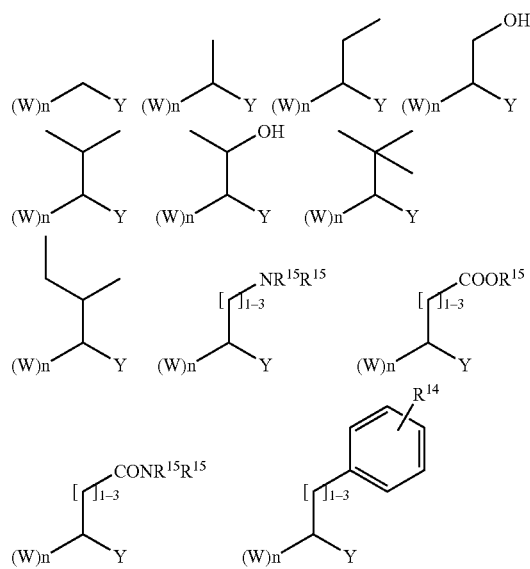

wherein R[14] and R[15] are as defined previously.

Even more preferred compounds of general formula (I), comprise $(X)_o$ groups that are simple alkyl groups such as methylene and where o=0 or 1.

In the group $(W)_n$:

W is preferably O, S, SO$_2$, S(O), C(O) or when o is one or greater, NR$^{11}$, where R$^{11}$ is C$_{0-4}$-alkyl; and n is 0 or 1.

More preferred compounds of general formula (I), comprise $(W)_n$ groups defined as O, S, SO$_2$, C(O) and where n=0 or 1.

In the group $(V)_m$:

V is preferably C(O), C(O)NH or CHR$^{13}$, where R$^{13}$ is C$_{0-4}$-allyl; and m is 0 or 1.

Preferred V and W substituent combinations encompassed by general formula (I) include, but are not limited to:

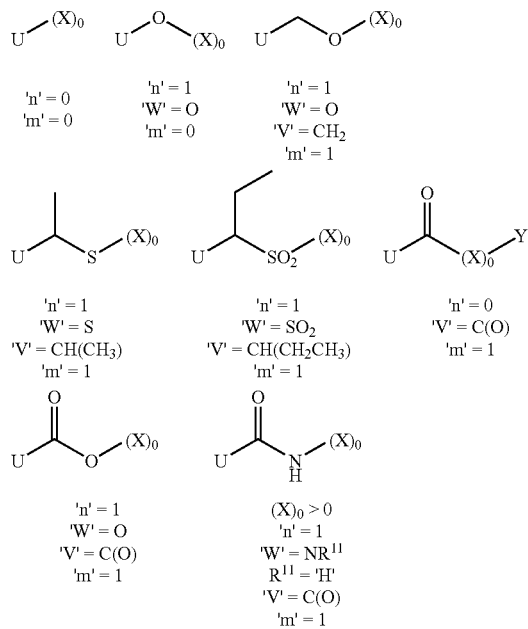

More preferred V, W and X substituent combinations encompassed by general formula (I) comprise, but are not limited to

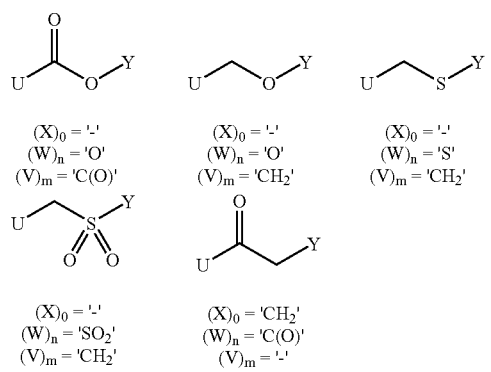

In preferred compounds of general formula (I), U comprises an optionally substituted 5- or 6-membered saturated or unsaturated heterocycle or Ar group or an optionally substituted saturated or unsaturated 9- or 10-membered heterocycle or Ar group. Examples of such preferred U rings include the following:

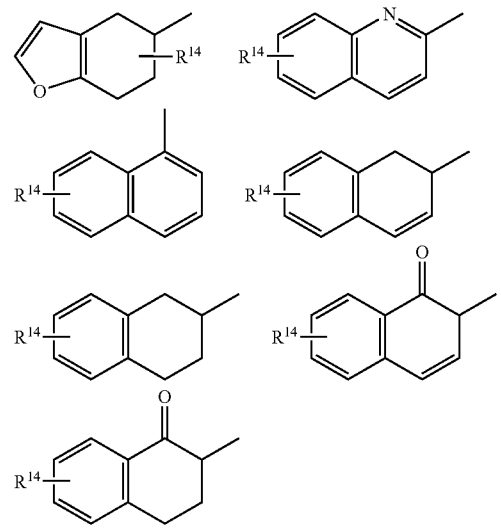

and also the following

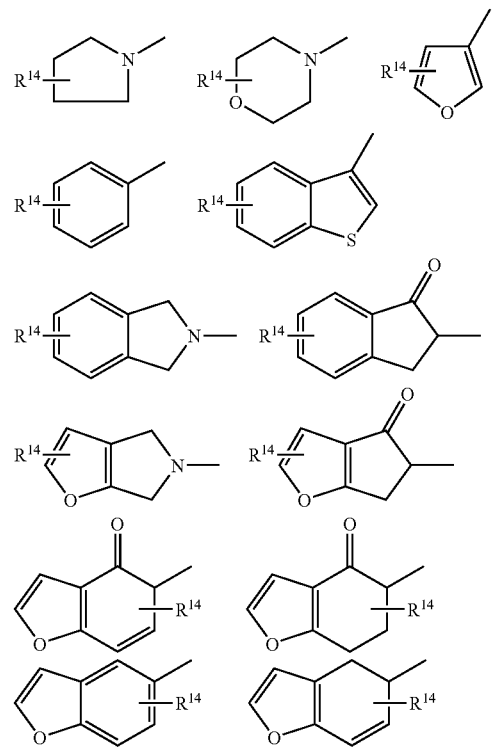

wherein R$^{14}$ is as defined previously.

More preferred compounds of general formula (I), contain a U group comprising of a bulky alkyl or aryl group at the para position of an aryl Ar. Also, more preferred compounds contain a meta or para-biaryl Ar—Ar, where Ar is as previously defined. Additionally, more preferred compounds contain a 6, 6 or 6, 5 or 5,6-fused aromatic ring. Examples of more preferred U groups are

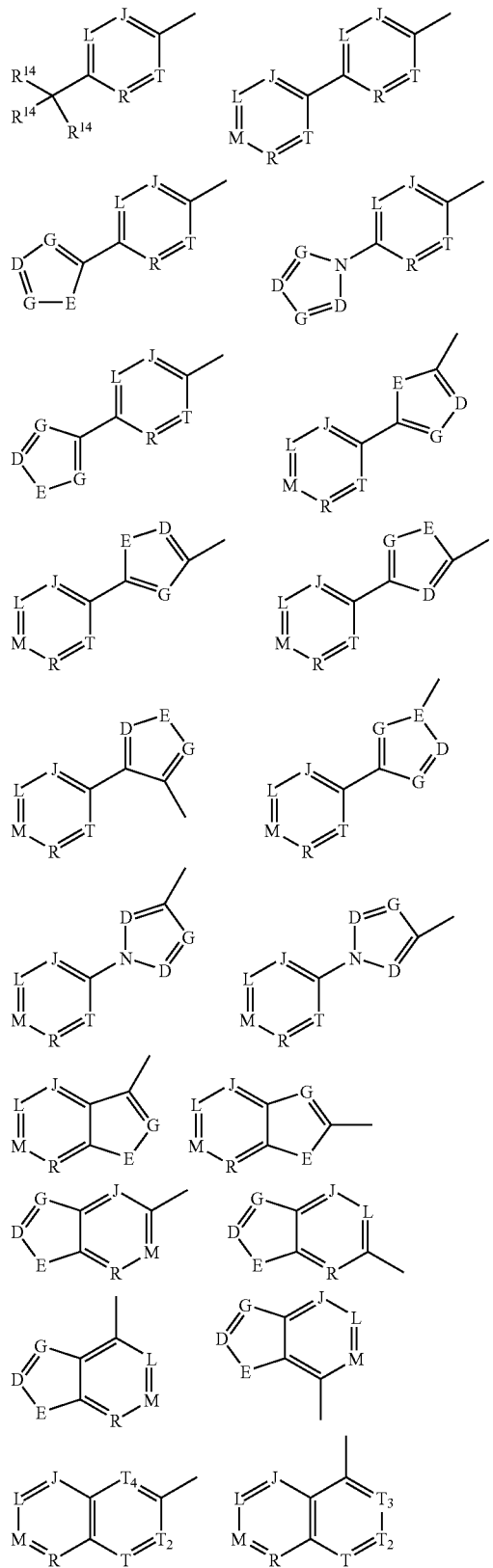

wherein $R^{14}$, D, E, G, J, L, M, R, T, $T_2$, $T_3$ and $T_4$ are as defined previously.

Even more preferred compounds of general formula (I), particularly for inhibition of cruzipain, contain a U group comprising a 6-membered Ar ring containing a bulky alkyl or aryl group at the para position, where Ar is as previously defined

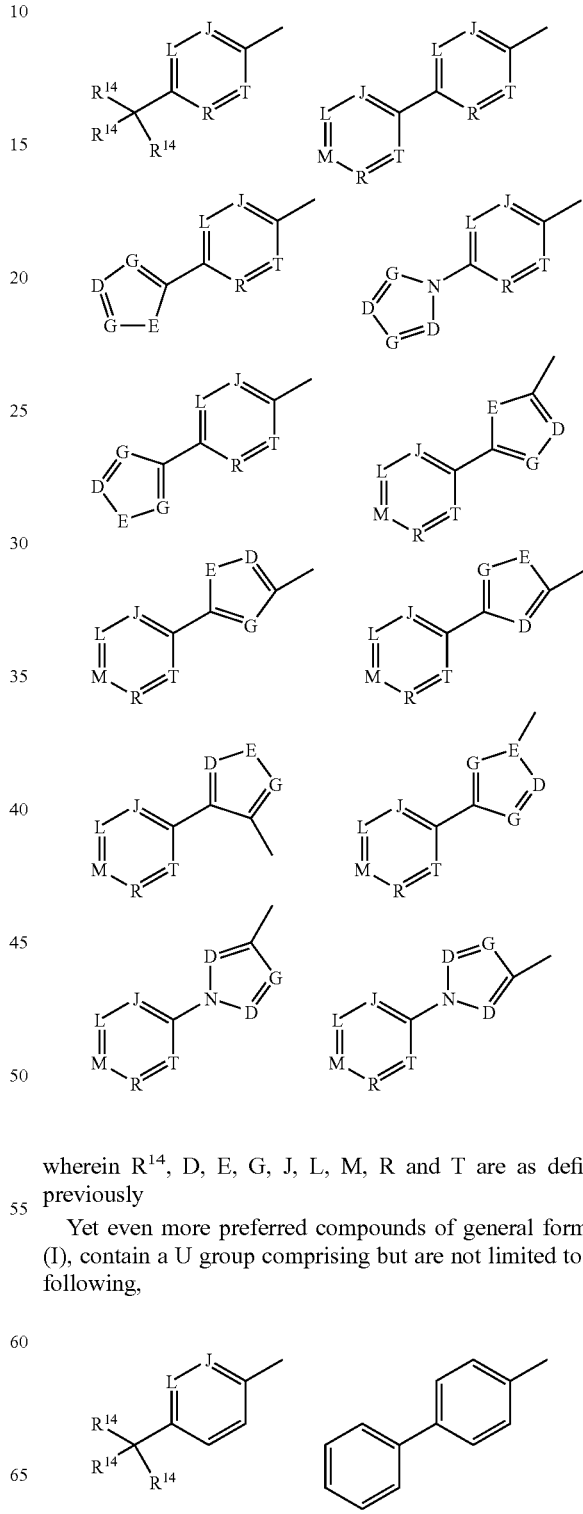

wherein $R^{14}$, D, E, G, J, L, M, R and T are as defined previously

Yet even more preferred compounds of general formula (I), contain a U group comprising but are not limited to the following, -continued

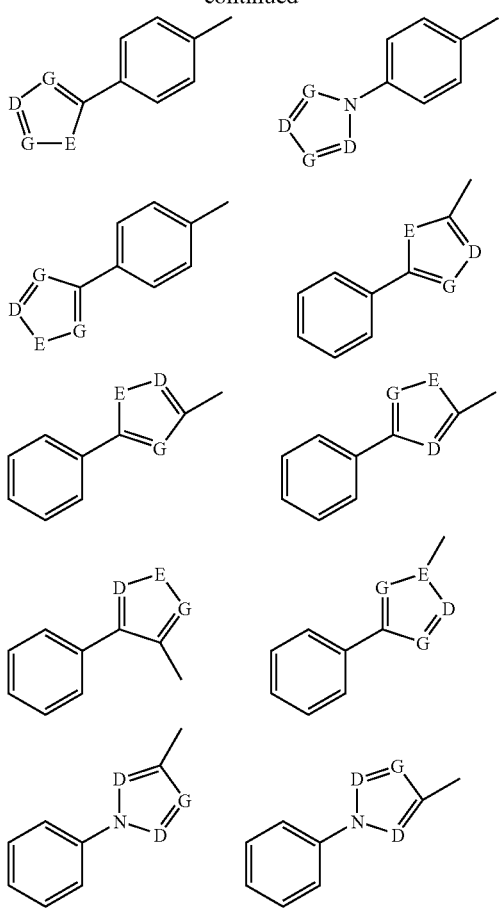

wherein $R^{14}$, D, E, G, J and L are as defined previously.

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984. Compounds of formula (I) and the intermediates and starting materials used in their preparation are named in accordance with the IUPAC rules of nomenclature in which the characteristic groups have decreasing priority for citation as the principle group. An example compound of formula (I), compound (1) in which $R^1$ is H, $R^2$ is methyl, Z is oxygen, Y is 4-methylpentyl, $(X)_o$ is zero, $(W)_n$ is oxygen, $(v)_m$ is methylene and U is phenyl is thus named:—

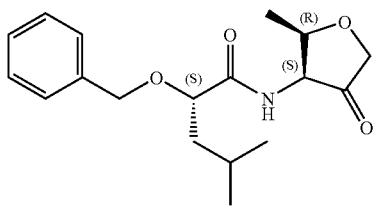

(1)

2S-Benzyloxy-4-methyl-pentanoic acid (2R-methyl-4-oxo-tetrahydrofuran-3S-yl)-amide A second example compound of formula (I), compound (2) in which $R^1$ is H, $R^2$ is methyl, Z is sulphur, Y is 4-methylpentyl, $(X)_0$ is zero, $(W)_n$ is oxygen, $(V)_m$ is methylene and U is phenyl is thus named:—

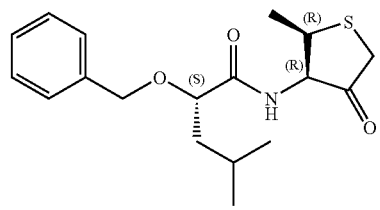

(2)

2S-Benzyloxy-4-methyl-pentanoic Acid (2R-methyl-4-oxo-tetrahydrothiophen-3R-yl)amide A third example compound of formula (I), compound (3) in which $R^1$ is H, $R^2$ is methyl, Z is methylene, Y is 4-methylpentyl, $(X)_0$ is zero, $(W)_n$ is oxygen, $(V)_m$ is methylene and U is phenyl is thus named:—

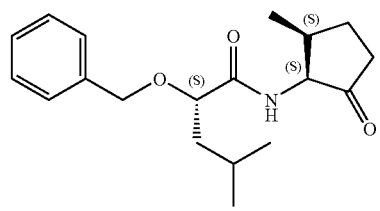

(3)

2S-Benzyloxy-4-methylpentanoic Acid (2S-methyl-5-oxo-cyclopent-3S-yl)amide

Compounds of the invention include, but are not limited to, the following examples where all 4 stereoisomeric combinations of the cyclic ketone are included, i.e. (2S, 3S), (2R, 3S), (2S, 3R), (2R, 3R) and where Z='O' and $R^1$='H', and also include the equivalent analogues included in the full definition of Z and $R^1$ and $R^2$ 4-Methyl-2-(4-trifluoromethylbenzyloxy)-pentanoic acid (2-methyl 4-oxo-tetrahydro furan-3-yl)-amide N-(2-Methyl-4-oxo-tetrahydro-furan-3-yl)-3-phenyl-2-(4-trifluoromethylbenzyloxy)-propionamide 3-(4-Hydroxyphenyl)-N-(2-methyl-4-oxo-tetrahydro-furan-3-yl)-2-(4-trifluoromethyl-benzyloxy)-propionamide 2-Benzyloxy-4-methyl-pentanoic acid (2-methyl-4-oxo-tetrahydro-furan-3-yl)-amide 2-Benzyloxy-N-(2-methyl-4-oxo-tetrahydro-furan-3-yl)-3-phenyl-propionamide 2-Benzyloxy-3-(4-hydroxyphenyl)-N-(2-methyl-4-oxo-tetrahydro-furan-3-yl)-propionamide 4-Methyl-2-(4-thiophen-2-yl-benzyloxy)-pentanoic acid (2-methyl-4-oxo-tetrahydro-furan-3-yl)-amide N-(2-Methyl-4-oxo-tetrahydro-furan-3-yl)-3-phenyl-2-(4-thiophen-2-yl-benzyloxy)-propionamide 3-(4-Hydroxyphenyl)-N-(2-methyl-4-oxo-tetrahydro-furan-3-yl)-2-(4-thiophen-2-yl-benzyloxy)-propionamide 2-(4-tert-Butyl-benzyloxy)-4-methyl-pentanoic acid (2-methyl-4-oxo-tetrahydro-furan-3-yl)-amide 2-(4-tert-Butyl-benzyloxy)-N-(2-methyl-4-oxo-tetrahydro-furan-3-yl)-3-phenyl-propionamide 2-(4-tert-Butyl-benzyloxy)-3-(4-hydroxyphenyl)-N-(2-methyl-4-oxo-tetrahydro-furan-3-yl)-propionamide 2-(Biphenyl-4-ylmethoxy)-4-methyl-pentanoic acid (2-methyl-4-oxo-tetrahydro-furan-3-yl)-amide 2-(Biphenyl-4-ylmethoxy)-N-(2-methyl-4-oxo-tetrahydro-furan-3-yl)-3-phenyl-propionamide 2-(Biphenyl-4-ylmethoxy)-3-(4-hydroxyphenyl)-N-(2-methyl-4-oxo-tetrahydro-furan-3-yl)-propionamide 2-(4-tert-Butyl-benzylsulfanyl)-4-methyl-pentanoic acid (2-methyl-4-oxo-tetrahydro-furan-3-yl)-amide 2-(4-tert-Butyl-benzylsulfanyl)-3-(4-hydroxyphenyl)-N-(2-methyl-4-oxo-tetrahydro-furan-3-yl)-propionamide 2-(Biphenyl-4-ylmethylsulfanyl)-4-methyl-pentanoic acid (2-methyl-4-oxo-tetrahydro-furan-3-yl)-amide 2-(Biphenyl-4-ylmethylsulfanyl)-3-(4-hydroxyphenyl)-N-(2-methyl-4-oxo-tetrahydro-furan-3-yl)-propionamide 4-Methyl-2-(4-thiophen-2-yl-benzylsulfanyl)-pentanoic acid (2-methyl-4-oxo-tetrahydro-furan-3-yl)-amide 3-(4-Hydroxyphenyl)-N-(2-methyl-4-oxo-tetrahydro-furan-3-yl)-2-(4-thiophen-2-yl-benzylsulfanyl)-propionamide 2-(4-tert-Butyl-phenylmethanesulfonyl)-4-methyl-pentanoic acid (2-methyl-4-oxo-tetrahydro-furan-3-yl)-amide 2-(4-tert-Butyl-phenylmethanesulfonyl)-3-(4-hydroxyphenyl)-N(2-methyl-4-oxo-tetrahydro-furan-3-yl)-propionamide 2-(Biphenyl-4-ylmethanesulfonyl)-4-methyl-pentanoic acid (2-methyl-4-oxo-tetrahydro-furan-3-yl)-amide 2-(Biphenyl-4-ylmethanesulfonyl)-3-(4-hydroxyphenyl)-N-(2-methyl-4-oxo-tetrahydro-furan-3-yl)-propionamide 4-Methyl-2-(4-thiophen-2-yl-phenylmethanesulfonyl)-pentanoic acid (2-methyl-4-oxo-tetrahydro-furan-3-yl)-amide 3-(4-Hydroxyphenyl)-N-(2-methyl-4-oxo-tetrahydro-furan-3-yl)-2-(4-thiophen-2-yl-phenylmethanesulfonyl)-propionamide 3-Phenyl-pyrrole-1-carboxylic acid 2-(4-hydroxyphenyl)-1-(2-methyl-4-oxo-tetrahydro-furan-3-ylcarbamoyl)-ethyl ester 3-Phenyl-pyrrole-1-carboxylic acid 3-methyl-1-(2-methyl-4-oxo-tetrahydro-furan-3-ylcarbamoyl)-butyl ester 1,3-Dihydro-isoindole-2-carboxylic acid 2-(4-hydroxyphenyl)-1-(2-methyl-4-oxo-tetrahydro-furan-3-ylcarbamoyl)-ethyl ester 1,3-Dihydro-isoindole-2-carboxylic acid 3-methyl-1-(2-methyl-4-oxo-tetrahydro-furan-3-ylcarbamoyl)-butyl ester 3,4-Dihydro-1H-isoquinoline-2-carboxylic acid 2-(4-hydroxyphenyl)-1-(2-methyl-4-oxo-tetrahydro-furan-3-ylcarbamoyl)-ethyl ester 3,4-Dihydro-1H-isoquinoline-2-carboxylic acid 3-methyl-1-(2-methyl-4-oxo-tetrahydro-furan-3-ylcarbamoyl)-butyl ester 2-(4-Hydroxybenzyl)-N-(2-methyl-4-oxo-tetrahydro-furan-3-yl)-4-oxo-4-(3-phenylpyrrol-1-yl)-butyramide 4-Methyl-2-[2-oxo-2-(3-phenyl-pyrrol-1-yl)-ethyl]-pentanoic acid (2-methyl-4-oxo-tetrahydro-furan-3-yl)-amide 4-(1,3-Dihydro-isoindol-2-yl)-2-(4-hydroxybenzyl)-N-(2-methyl-4-oxo-tetrahydro-furan-3-yl)-4-oxo-butyramide 2-[2-(1,3-Dihydro-isoindol-2-yl)-2-oxo-ethyl]4-methyl-pentanoic acid (2-methyl-4-oxo-tetrahydro-furan-3-yl)-amide 4-(3,4-Dihydro-1H-isoquinolin-2-yl)-2-(4-hydroxybenzyl)-N-(2-methyl-4-oxo-tetrahydro-furan-3-yl)-4-oxo-butyramide 2-[2-(3,4-Dihydro-1H-isoquinolin-2-yl)-2-oxo-ethyl]-4-methyl-pentanoic acid (2-methyl-4-oxo-tetrahydro-furan-3-yl)-amide Additional compounds of the invention include, but are not limited to, the following examples where all 4 stereoisomeric combinations of the cyclic ketone are included, i.e. (2S, 3S), (2R, 3S), (2S, 3R), (2R, 3R) and where Z='O' and $R^1$='H', and also include the equivalent analogues included in the full definition of Z and $R^1$ and $R^2$ 3-(4-Hydroxyphenyl)-N-(2-methyl-4-oxo-tetrahydro-furan-3-yl)-2-(naphthalen-1-ylmethoxy)-propionamide N-(2-Methyl-4-oxo-tetrahydro-furan-3-yl)-2-(naphthalen-1-ylmethoxy)-3-phenyl-propionamide 2-Benzyloxy-3-cyclohexyl-N-(2-methyl oxo-tetrahydro-furan-3-yl)-propionamide 3-Cyclohexyl-2-(furan-3-ylmethoxy)-N-(2-methyl-4-oxo-tetrahydro-furan-3-yl)-propionamide 3-Cyclohexyl-N-(2-methyl-4-oxo-tetrahydro-furan-3-yl)-2-(thiophen-3-ylmethoxy)-propionamide 3-Cyclohexyl-2-(furan-2-ylmethoxy)-N-(2-methyl-4-oxo-tetrahydro-furan-3-yl)-propionamide 3-Cyclohexyl-N-(2-methyl-4-oxo-tetrahydro-furan-3-yl)-2-(thiophen-2-ylmethoxy)-propionamide 2-(Benzo[b]thiophen-3-ylmethoxy)-3-cyclohexyl-N-(2-methyl-4-oxo-tetrahydro-furan-3-yl)-propionamide 2-(Furan-3-ylmethoxy)-4,4-dimethyl-pentanoic acid (2-methyl-4-oxo-tetrahydro-furan-3-yl)-amide 4,4-Dimethyl-2-(thiophen-3-ylmethoxy)-pentanoic acid (2-methyl-4-oxo-tetrahydro-furan-3-yl)-amide 2-(Furan-2-ylmethoxy)-4,4-dimethyl-pentanoic acid (2-methyl-4-oxo-tetrahydro-furan-3-yl)amide 4,4-Dimethyl-2-(thiophen-2-ylmethoxy)-pentanoic acid (2-methyl-4-oxo-tetrahydro-furan-3-yl)-amide 2-(Benzo[b]thiophen-3-ylmethoxy)-4,4-dimethyl-pentanoic acid (2-methyl-4-oxo-tetrahydro-furan-3-yl)-amide 3-Cyclohexyl-2-(furan-3-ylmethylsulfanyl)-N-(2-methyl-4-oxo-tetrahydro-furan-3-yl)-propionamide 3-Cyclohexyl-N-(2-methyl-4-oxo-tetrahydro-furan-3-yl)-2-(thiophen-3-ylmethylsulfanyl)-propionamide 3-Cyclohexyl-2-(furan-2-ylmethylsulfanyl)-N-(2-methyl-4-oxo-tetrahydro-furan-2-yl)-propionamide 3-Cyclohexyl-N-(2-methyl-4-oxo-tetrahydro-furan-3-yl)-2-(thiophen-2-ylmethylsulfanyl)-propionamide 2-(Benzo[b]thiophen-3-ylmethylsulfanyl)-3-cyclohexyl-N-(2-methyl-4-oxo-tetrahydro-furan-3-yl)-propionamide 2-(Furan-3-ylmethylsulfanyl)-4,4-dimethyl-pentanoic acid (2-methyl-4-oxo-tetrahydro-furan-3-yl)-amide 4,4-Dimethyl-2-(thiophen-3-ylmethylsulfanyl)-pentanoic acid (2-methyl-4-oxo-tetrahydro-furan-3-yl)-amide 2-(Furan-2-ylmethylsulfanyl)-4,4-dimethyl-pentanoic acid (2-methyl-4-oxo-tetrahydro-furan-3-yl)-amide 4,4-Dimethyl-2-(thiophen-2-ylmethylsulfanyl)-pentanoic acid (2-methyl-4-oxo-tetrahydro-furan-3-yl)-amide 2-(Benzo[b]thiophen-3-ylmethylsulfanyl)-4,4-dimethyl-pentanoic acid (2-methyl-4-oxo-tetrahydro-furan-3-yl)-amide 3-(4-Hydroxyphenyl)-N-(2-methyl-4-oxo-tetrahydro-furan-3-yl)-2-naphthalen-1-ylmethylsulfanyl)-propionamide 3-Cyclohexyl-2-(furan-3-ylmethanesulfonyl)-N-(2-methyl-4-oxo-tetrahydro-furan-3-yl)-propionamide 3-Cyclohexyl-N-(2-methyl-4-oxo-tetrahydro-furan-3-yl)-2-(thiophen-3-ylmethanesulfonyl)-propionamide 3-Cyclohexyl-2-(furan-2-ylmethylsulfonyl)-N-(2-methyl-4-oxo-tetrahydro-furan-2-yl)-propionamide 3-Cyclohexyl-N-(2-methyl-4-oxo-tetrahydro-furan-3-yl)-2-(thiophen-2-ylmethylsulfonyl)-propionamide 2-(Benzo[b]thiophen-3-ylmethylsulfonyl)-3-cyclohexyl-N-(2-methyl-4-oxo-tetrahydro-furan-3-yl)-propionamide 2-(Furan-3-ylmethylsulfonyl)-4,4-dimethyl-pentanoic acid (2-methyl-4-oxo-tetrahydro-furan-3-yl)-amide 4,4-Dimethyl-2-(thiophen-3-ylmethylsulfonyl)-pentanoic acid (2-methyl-4-oxo-tetrahydro-furan-3-yl)-amide 2-(Furan-2-ylmethylsulfonyl)-4,4-dimethyl-pentanoic acid (2-methyl-4-oxo-tetrahydro-furan-3-yl)-amide 4,4-Dimethyl-2-(thiophen-2-ylmethylsulfonyl)-pentanoic acid (2-methyl-4-oxo-tetrahydro-furan-3-yl)-amide 2-(Benzo[b]thiophen-3-ylmethylsulfonyl)-4,4-dimethyl-pentanoic acid (2-methyl-4-oxo-tetrahydro-furan-3-yl)-amide 3-(4-Hydroxyphenyl)-N-(2-methyl-4-oxo-tetrahydro-furan-3-yl)-2-(naphthalen-1-ylmethylsulfonyl)-propionamide Morpholine-4-carboxylic acid 2-cyclohexyl-1-(2-methyl-4-oxo-tetrahydro-furan-3-ylcarbamoyl)-ethyl ester Morpholine-4-carboxylic acid 3,3-dimethyl-1-(2-methyl-4-oxo-tetrahydro-furan-3-ylcarbamoyl)-butyl ester 2-Cyclohexylmethyl-N-(2-methyl-4-oxo-tetrahydro-furan-3-yl)-4-morpholin-4-yl-4-oxo-butyramide 4,4-Dimethyl-2-(2-morpholinyl-2-oxo-ethyl)-pentanoic acid (2-methyl-4-oxo-tetrahydro-furan-3-yl)-amide 2-Biphenyl-3-yl-4-methyl-pentanoic acid (2-methyl-4-oxo-tetrahydro-fan-3-yl)-amide To those skilled in the practices of organic chemistry, compounds of general formula (I) may be readily synthesised by a number of chemical strategies, performed either in solution or on the solid phase (see Atherton, E. and Sheppard, R. C. In 'Solid Phase Peptide Synthesis: A Practical Approach', Oxford University Press, Oxford, U.K. 1989, for a general review of solid phase synthesis principles). The solid phase strategy is attractive in being able to generate many thousands of analogues, typically on a 5–100 mg scale, through established parallel synthesis methodologies (e.g. see (a) Bastos, M.; Maeji, N.J.; Abeles, R. H. *Proc. Natl. Acad. Sci. USA*, 92, 6738–6742, 1995).

Therefore, one strategy for the synthesis of compounds of general formula (I) comprises:—

(a) Preparation of an appropriately functionalised and protected (2-alkyl-4-oxo-tetrahydrofuran-3-yl)amide or a (2-alkyl-4-oxo-tetrahydrothiophen-3-yl)amide or a (2-alkyl-5-oxocyclopentyl)amide building block in solution.

(b) Attachment of the building block (a) to the solid phase through a linker that is stable to the conditions of synthesis but readily labile to cleavage at the end of a synthesis (see James, I. W., *Tetrahedron*, 55(*Report N°* 489), 4855–4946, 1999, for examples of the 'linker' function as applied to solid phase synthesis).

(c) Solid phase organic chemistry (see Brown, P D. *J. Chem. Soc., Perkin Trans.* 1, 19, 3293–3320, 1998), to construct the remainder of the molecule.

(d) Compound cleavage from the solid phase into solution.

(e) Cleavage work-up and compound analysis.

The first stage in a synthesis of compounds of general formula (I) is the preparation in solution of a functionalised and protected building block. A typical scheme towards the (2-alkyl-4-oxo-tetrahydrofuran-3-yl)amide (6) is detailed in Scheme 1.

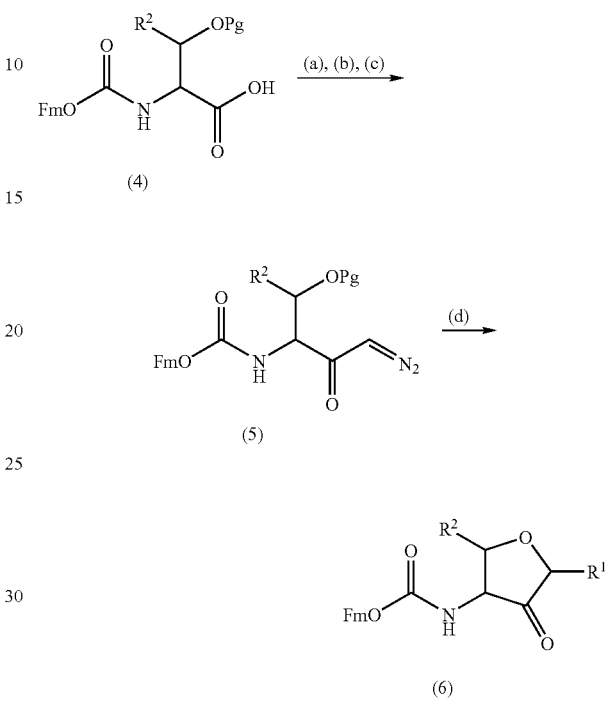

Scheme 1. (a) $^t$BuOCOCl, NMM, DCM, −15° C., 10 mins, under argon. (b) Diazomethane in diethyl ether, −15° C. to RT over 1 hr. (c) Acetic acid (d) LiCl (10 eq) in 80% aq acetic acid, 5° C. to RT over 1 hr.

FmOC(O) denotes the well known amine protecting group 9-fluorenyl methoxycarbonyl (Fmoc, see Atherton, E. and Sheppard, R. C., 1989) and 'Pg' denotes either a free hydroxyl or an hydroxylprotecting group such as tert-butyl ether. In the illustrated case, condensation with diazomethane provides $R^1$=H.

Considering step (a), synthesis may commence from suitably protected β-hydroxy-α-amino acids (4), which are accessible through a variety of literature methods e.g. (a) Adams, Z. M., Jackson, R. F. W., Palmer, N.J., Rami, H. K, Wythes, M. J., *J. Chem. Soc., Perkin Trans I*, 937–947, 1999, (b) Hubschwerlen, C., et al, *J. Med. Chem.*, 4, 3972–3975, 1998, (c) Luzzio, F. A., et al, *Tet. Lett.*, 41, 7151–7155, 2000, (d) Morgan, A. J. et al, *Org. Lett.* 1(12), 1949–1952, 1999. (e) Zhang, H., Xia, P., Zhou, W., *Tetrahedron: Asymmetry*, 11, 3439–3447, 2000, (f) Blaskovich, M. A., et al, *J. Org. Chem.*, 6, 3631–3646, 1998.

In the simplest case where $R^2$ is a methyl substituent, the β-hydroxy-α-amino acid (4) is threonine (Thr) for which all four stereoisomers (i.e. α 'R' or 'S' and β 'R' or 'S') are commercially available. Activation of the suitably protected β-hydroxy-α-amino acids (4) via isobutyl chloroformate mixed anhydride, followed by condensation with diazomethane, yields the diazomethylketone intermediates (5). Treatment of diazomethylketone intermediates (5) with lithium chloride in aqueous acetic acid provides the protected (2-alkyl-4-oxo-tetrahydrofuran-3-yl)amide (6). Introduction of simple $R^1$ substituents may be achieved by condensation of activated (4) with alternatives to diazomethane such as diazoethane ($R^1$=$CH_3$), or 1-phenyloxy-diazoethane ($R^1$=$CH_2OPh$).

The protected building blocks (synthesis exemplified by the (2-alkyl-4-oxo-tetrahydrofuran-3-yl)amide (6) detailed in Scheme 1) may be utilised in a solid phase synthesis of inhibitor molecules (steps (b) to (e)). Step (b), the solid phase linkage of an aldehyde or ketone, has previously been described by a variety of methods (e.g. see (a) James, I. W., 1999, (b) Lee, A., Huang, L., Ellman, J. A., *J. Am. Chem. Soc*, 121(43), 9907–9914, 1999, (c) Murphy, A. M., et al, J. Am. Chem. Soc, 114, 3156–3157, 1992). A suitable method amenable to the reversible linkage of an alkyl ketone functionality such as (6) is through a combination of the previously described chemistries. The semicarbazide, 4-[[(hydrazinocarbonyl)amino] methyl]cyclohexane carboxylic acid.trifluoroacetate (7) (Murphy, A. M., et al, J. Am. Chem. Soc, 114, 3156–3157, 1992), may be utilised as illustrated in Scheme 2, exemplified by linkage of the (2-alkyl-4-oxo-tetrahydrofuran-3-yl)amide (6).

Loaded construct (9) may be reacted with a wide range of carboxylic acids available commercially or in the literature, to introduce the left-hand portion 'U-V-W-X-Y' in general formula (I). In the simplest example, the entire left hand portion of an inhibitor of general formula (I) can be prepared in solution by traditional organic chemistry methods and coupled to construct (9) on the solid phase (Schemes 3–7). For example (Scheme 3), treatment in solution of an amino acid, exemplified by (10) with sodium nitrite/$H_2SO_4$, provides the α-hydroxyacid, exemplified by (11) (Degerbeck, F. et al, *J. Chem. Soc, Perkin Trans.* 1, 11–14, 1993). Treatment of α-hydroxyacid, (11) with sodium hydride in a dimethylformamide/dichloromethane mixture followed by addition of benzyl bromide, provides 2RS-benzyloxy-3-cyclohexyl-propionic acid (12). Coupling of (12) to the solid phase construct (9) followed by cleavage, provides (13), an example of general formula (I) where $R^3$='H', $(X)_o$='-', $(W)_n$='O', n=1, $(V)_m$='$CH_2$', i.e. $R^{12}$, $R^{13}$='H', m=1 and U=phenyl. To those skilled in the practices of organic synthesis, a wide variety of aminoacids such as (10) may be converted to the corresponding α-hydroxyacid such as (11) following the general conditions detailed. Additionally, ben-

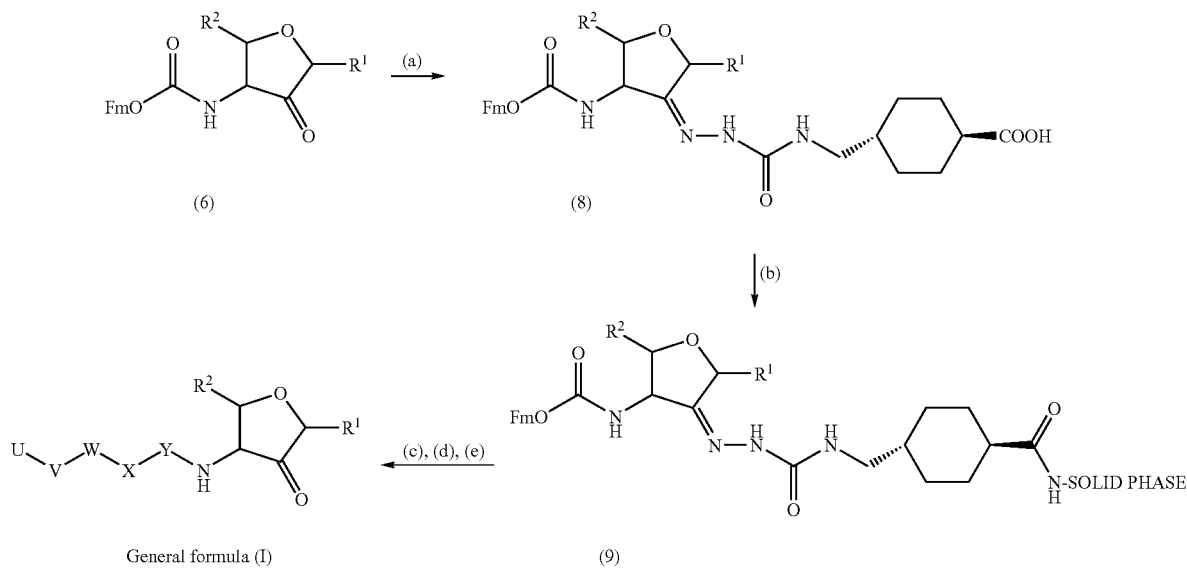

Scheme 2. (a) (6) in 90% EtOH/$H_2O$/1.5 eq NaOAc/4-[[(hydrazinocarbonyl)amino] methyl]cyclohexane carboxylic acid.trifluoroacetate (7), 2 hr reflux. (O) 3 eq construct (8)/HBTU/HOBt/NMM, NH$_2$-SOLID PHASE, DMF, RT, o/n. (c) 20% piperidine/DMF, 30 mins. (d) Range of chemistries to introduce U-V-W-X-Y (e) TFA/$H_2O$ (95:5, v/v), RT, 2 hr.

Construct (8) is prepared through reaction of the linker molecule (7) and the (2-alkyl-4-oxo-tetrahydrofuran-3-yl) amide (6) by reflux in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of (8), providing the loaded construct (9).

zylbromide may be replaced by any reasonable Ar—$CR^{12}R^{13}$-halogen, providing many variations of carboxylic acid (12) following the general conditions detailed. In certain instances, it may be advantageous to temporarily protect the carboxylic acid as the methyl ester (for example compound (18), Scheme 5) prior to reaction with the alkylhalide. The ester intermediate is then simply hydrolysed to acid (12). Thus analogues of (13) exploring a wide range of $(V)_m$ and U in general formula (I) may be prepared through the general conditions detailed in Scheme 3. Since the final synthetic step involves a trifluoroacetic acid (TFA) mediated cleavage of the solid phase bound compound, compounds where the substituted ether is labile to TFA may be prepared in solution by an alternative route (see Scheme 10).

Scheme 3.

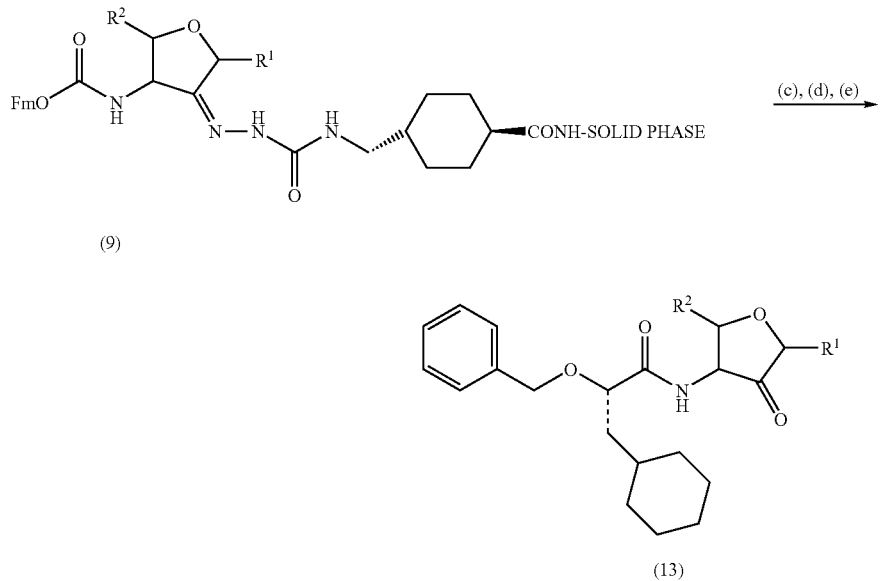

(9)

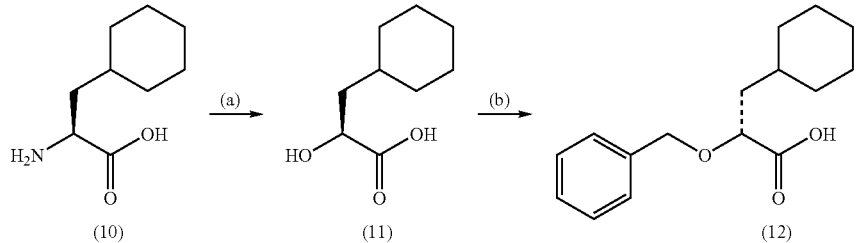

(10) → (11) → (12)

(a) NaNO$_2$/H$_2$SO$_4$, 0° C → RT, 24 hr (b) 2.3 eq NaH, 1:1 DMF/DCM, 1.4 eq benzylbromide, o/n (c) 20% piperidine/DMF, 30 mins. (d) 5 eq (12)/HBTU/HOBt/NMM, DMF, RT, o/n (e) TFA/H$_2$O (95:5, v/v), RT, 2 hr.

General formula (I) where
$R^3$ = 'H'
$(X)_0$ = '-'
$(W)_n$ = 'O', n = 1
$(V)_m$ = 'CH$_2$', i.e. $R^{12}$, $R^{13}$ = 'H', m = 1
U = phenyl
z = 'O'

Alternatively, coupling of construct (9) (following removal of Fmoc) with the α-hydroxyacid (11), provides a versatile solid phase bound intermediate 'Y' substituent in general formula (I) that may be reacted with many reagents. For example, the α-hydroxyl can be reacted under Mitsunobu conditions (Hughes, D. L. *Org. React.* (*N.Y*), 42, 335–656, 1992) to give ethers (i.e. X='-', W='O', in general formula (I)) (see Grabowska, U. et al, *J. Comb. Chem.*, 2(5), 475–490, 2000, for an example of Mitsunobu reaction on the solid phase). Alternatively, the α-hydroxyl can be reacted with a carbamoyl chloride to give a carbamate (i.e. X='-', W='O', V='NHC(O)', in general formula (I)).

Alternatively, (Scheme 4), treatment in solution of an amino acid, exemplified by (10) with sodium nitrite/H$_2$SO$_4$/potassium bromide provides the α-bromoacid, exemplified by (14) (Souers, A. J. et al, *Synthesis*, 4, 583–585, 1999) with retention of configuration. Treatment of α-bromoacid (14) with an alkylthiol exemplified by furan-2-ylmethanethiol (15) in dimethylformamide/triethylamine, provides 3-cyclohexyl-2R-(furan-2-ylsulfanyl)propionic acid (16), with inversion of configuration. Coupling of (16) to the solid phase construct (9) followed by cleavage, provides (17), an example of general formula (I) where $R^3$='H', $(X)_o$='-', $(W)_n$='S', n=1, $(V)_m$='CH$_2$', i.e. $R^{12}$, $R^{13}$='H', m=1 and U=2-furanyl. To those skilled in the practices of organic synthesis, a wide variety of aminoacids such as (10) may be converted to the corresponding α-bromoacid such as (14) following the general conditions detailed. Additionally, furan-2-ylmethanethiol (15) may be replaced by any reasonable Ar—CR$^{12}$R$^{13}$-SH, providing many variations of carboxylic acid (16) following the general conditions detailed. Thus analogues of (17) exploring a wide range of $(V)_m$ and U in general formula (I) may be prepared through the general conditions detailed in Scheme 4.

Scheme 4.

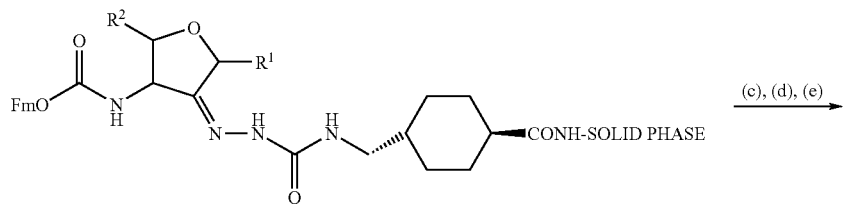

(9)

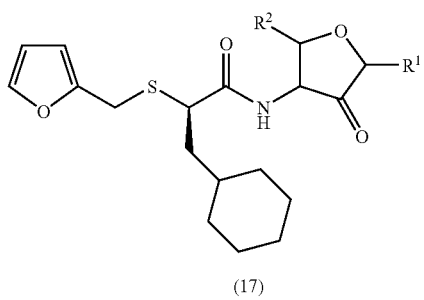

(17)

General formula (I) where
$R^3 = \text{'H'}$
$(X)_0 = \text{'-'}$
$(W)_n = \text{'S'}, n = 1$
$(V)_m = \text{'CH}_2\text{'}$, i.e. $R^{12}, R^{13} = \text{'H'}, m = 1$
$U$ = 2-furanyl
$Z = \text{'O'}$

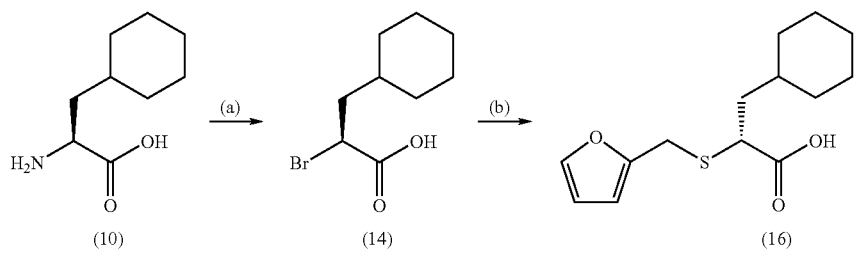

(10)         (14)         (16)

(a) $NaNO_2/H_2SO_4$, KBr 0° C → RT, o/n (b) Alkylthiol (15) /DMF/NEt$_3$, o/n (c) 20% piperidine/DMF, 30 mins. (d) 5 eq (16)/HBTU/HOBt/NMM, DMF, RT, o/n (e) TFA/H$_2$O (95:5, v/v), RT, 2hr.

Alternatively, coupling of construct (9) (following removal of Fmoc) with an α-bromoacid e.g. (14), provides a versatile intermediate 'Y' substituent in general formula (I) that may be reacted with many reagents. For example, the α-bromide can be displaced with nucleophiles e.g. alcohols, thiols, carbanions etc, to give ethers (i.e. X='-', W='O', in general formula (I)), thioethers (i.e. X='-', W='S', in general formula (I)). The thioethers may optionally be oxidised to the sulphone (see Scheme 8, i.e. X='-', W='SO$_2$', in general formula (I)) (see Grabowska, U. et al, *J. Comb. Chem.*, 2(5), 475–490, 2000, for an example of bromide displacement and thioether oxidation on the solid phase).

Alternatively, (Scheme 5), treatment of an α-hydroxyacid, exemplified by (11) with trimethylsilylchloride and methanol provides the methyl ester (18). Activation of the free hydroxyl to the chloroformate with phosgene in dichloromethane followed by addition of morpholine, then hydrolysis provides morpholine-4-carboxylic acid-1S-carboxy-2-cyclohexyl ethyl ester (19). Coupling of (19) to the solid phase construct (9) followed by cleavage, provides (20), an example of general formula (I) where $R^3=\text{'H'}$, $(X)_o\text{'-'}$, $(W)_n=\text{'O'}$, n=1, $(V)_m=\text{'CO'}$ and U=morpholino. To those skilled in the practices of organic synthesis, a wide variety of α-hydroxyacid esters such as (18) could be converted to the activated chloroformate following the general conditions detailed. Additionally, morpholine may be replaced by any reasonable amine, providing many variations of carboxylic acid (19) following the general conditions detailed. Thus analogues of (20) exploring a wide range of $(V)_m$ and U in general formula (I) may be prepared through the general conditions detailed in Scheme 5.

Scheme 5.

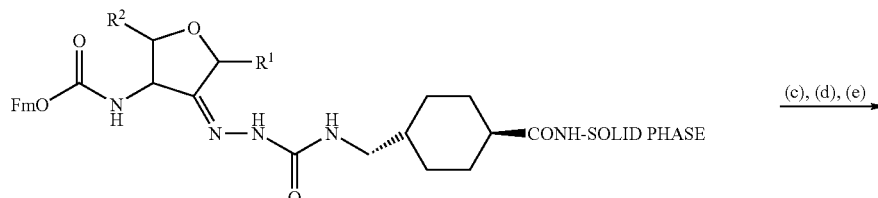

(9)

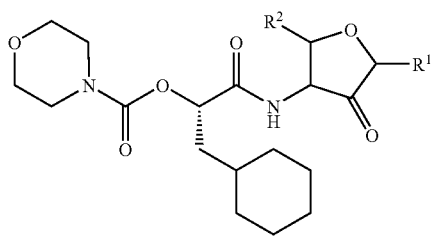

(20)

General formula (I) where
$R^3 = 'H'$
$(X)_o = '-'$
$(W)_n = 'O', n = 1$
$(V)_m = 'CO', m = 1$
$U = $ morpholino
$Z = 'O'$

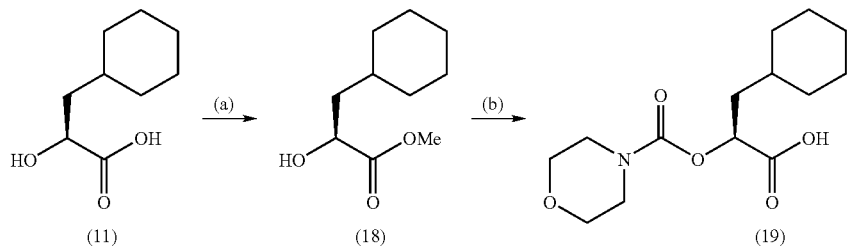

(11)　　　　　(18)　　　　　(19)

(a) Me₃SiCl, MeOH, RT, o/n. (b) i. COCl₂/DCM/ o/n, ii. Morpholine/DCM 0° C., 2 hr, iii. LiOH in H₂O/dioxan, 0° C. (c) 20% piperidine/DMF, 30 mins. (d) 5 eq (19)/HBTU/HOBt/ NMM, DMF, RT, o/n (e) TFA/H₂O (95:5, v/v), RT, 2 hr.

Alternatively, (Scheme 6), a wide range of alkylsuccinate esters exemplified by 2R-cyclohexylmethylsuccinic acid 1-methyl ester (21) are commercially available or readily prepared by known methods (see (a) Azam et al, *J. Chem Soc. Perkin Trans.* 1, 621-, 1996; (b) Evans et al, *J. Chem. Soc. Perkin Trans.* 1, 103, 2127, 1981; (c) Oikawa et al, *Tet. Lett,* 37, 6169, 1996). Carboxyl activation of alkylsuccinate ester (21) followed by addition of morpholine in dimethylformamide and subsequent ester hydroylsis, provides 2R-cyclohexylmethyl-4-morpholin-4-yl-4-oxo-butyric acid (22). Coupling of (22) to the solid phase construct (9) followed by cleavage, provides (23), an example of general formula (I) where $R^3='H'$, $(X)_o='CH_2'$ i.e. $R^9$, $R^{10}='H'$, o=1, $(W)_n='CO'$, n=1, $(V)_m='-'$ and U=morpholino. To those skilled in the practices of organic synthesis, a wide variety of alkylsuccinate esters such as (21) may be prepared and converted to the corresponding substituted alkylsuccinate acid such as (22) following the general conditions detailed. Additionally, morpholine may be replaced by any reasonable amine, providing many variations of carboxylic acid (22) following the general conditions detailed. Thus analogues of (23) exploring a wide range of $(X)_o$, $(V)_m$ and U in general formula (I) may be prepared through the general conditions detailed in Scheme 6.

Scheme 6.

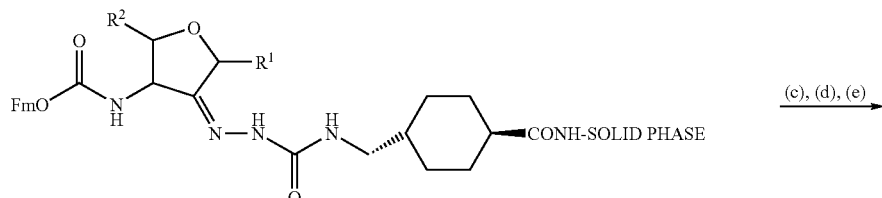

(9)

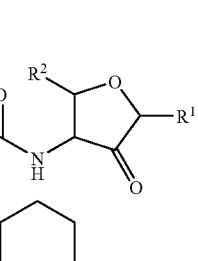

(23)

General formula (I) where
$R^3 = 'H'$
$(X)_o = 'CH_2'$ i.e. $R^9, R^{10} = 'H', o = 1$
$(W)_n = 'CO', n = 1$
$(V)_m = '-'$
U = morpholino
Z = 'O'

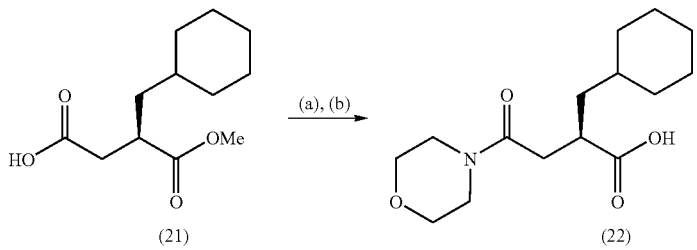

(21)  (22)

(a) i.EDC/1-hydroxybenzotriazole/DMF, 0° C., 30 mins. ii. Morpholine, RT, o/n. (b) LiOH in H₂O/dioxan, 0° C. (c) 20% piperidine/DMF, 30 mins. (d) 5 eq (22)/HBTU/HOBt/NMM, DMF, RT, o/n (e) TFA/H₂O (95:5, v/v), RT, 2 hr.

Alternatively, (Scheme 7), a wide range of biarylalkylacetic acids, exemplified by 2RS-biphenyl-3-yl-4-methylpentanoic acid (25) are readily available by known methods (see (a) DesJarlais, R L. et al, *J. Am. Chem. Soc,* 120, 9114–9115, 1998; (b) Oballa, R. M. et al, WO 0149288). Coupling of biarylalkylacetic acid (25) to the solid phase construct (9) followed by cleavage, provides (26), an example of general formula (I) where $R^3$='H', $(X)_o$='-', $(W)_n$='-', $(V)_m$='-' and U=m-biphenyl. To those skilled in the practices of organic synthesis, a wide variety of biarylalkylacetic acids such as (25) may be prepared by alkylation of the α-anion of the free acid analogue of (24), which in turn is prepared by Suzuki coupling of phenylboronic acid and 3-bromophenylacetic acid methyl ester. Phenylboronic acid may be replaced by a wide range of arylboronic acids in the Suzuki coupling, providing many variations of carboxylic acid (25) following the general conditions detailed. Thus analogues of (26) exploring a wide range of group 'U' in general formula (I) may be prepared through the general conditions detailed in Scheme 7.

Scheme 7.

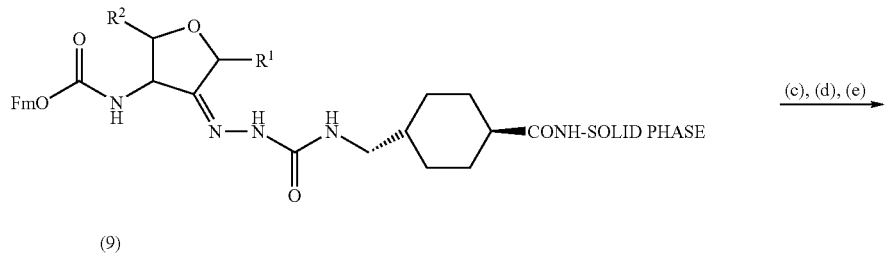

(9)

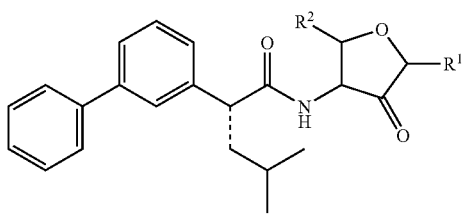

(26)

General formula (I) where
$R^3 = $ 'H'
$(X)_0 = $ '-'
$(W)_n = $ '-'
$(V)_m = $ '-'
U = m-biphenyl
Z = 'O'

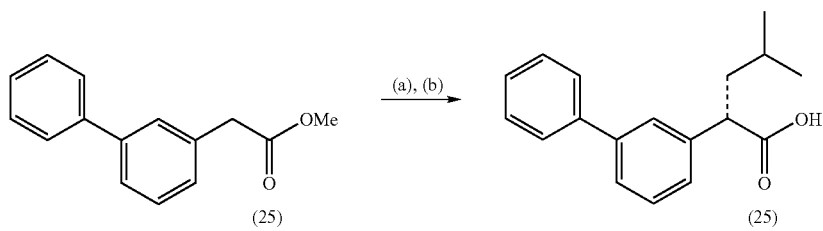

(a) LiOH in $H_2O$/Dioxan, 0° C. (b) i. LDA, THF, 2-methylpropenylbromide. ii. Pd/C, EtOH, $H_2$ (c) 20% piperidine/DMF, 30 mins. (d) 5 eq (25)/HBTU/HOBt/NMM, DMF, RT, o/n (e) TFA/$H_2O$ (95:5, v/v), RT, 2 hr.

Many other possibilities for solid phase organic chemistry (e.g. see Brown, R. D. *J. Chem. Soc., Perkin Trans.* 1, 19, 3293–3320, 1998, for a review of recent SPOC publications) can be used to derivatise construct (9) towards compounds of general formula (I). For example, the left-hand portion 'U-V-W-X-Y' in general formula (I) can be partially constructed in solution, coupled to construct (9) and further modified on the solid phase (Scheme 8). For instance, a simple extension of Scheme 4 is through the oxidation of the intermediate solid phase bound species, with m-chloroperbenzoic acid in dichloromethane prior to cleavage, to give the sulphone analogue (27). As described in Scheme 4, many variations of carboxylic acid (16) may be prepared following the general conditions detailed. Thus analogues of (27) exploring a wide range of $(V)_m$ and U in general formula (I) may be prepared through the general conditions detailed in Schemes 4 and 8.

Scheme 8.

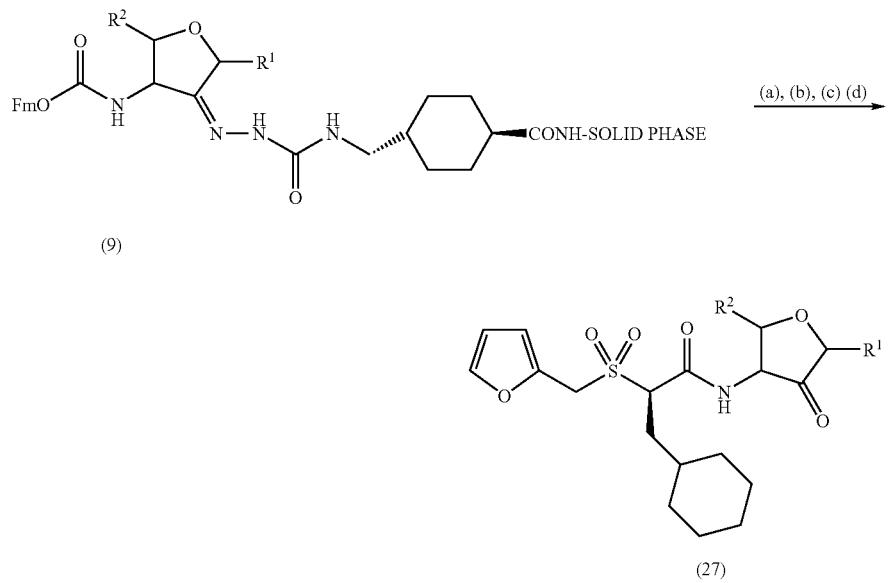

General formula (I) where
$R^3$ = 'H'
$(X)_0$ = '-'
$(W)_n$ = '$SO_2$', n = 1
$(V)_m$ = '$CH_2$', i.e. $R^{12}$, $R^{13}$ = 'H', m = 1
U = 2-furanyl
Z = 'O'

(a) 20% piperdine/DMF, 30 mins. (b) 5 eq (16)/HBTU/HOBt/NMM, DMF, RT, o/n
(c) 5 eq m-chloroperbenzoic acid/DCM, RT, 5 hr. (d) TFA/$H_2O$ (95:5, v/v), RT, 2 hr.

Compounds of general formula (I) can be finally released from the solid phase by treatment with trifluoroacetic acid/water, followed by evaporation, lyophylisation and standard analytical characterisation.

A second strategy for the synthesis of compounds of general formula (I) comprises:—

(f) Preparation of an appropriately functionalised and protected (2-alkyl-4-oxo-tetrahydrofuran-3-yl)amide or a (2-alkyl-4-oxo-tetrahydrothiophen-3-yl)amide or a (2-alkyl-5-oxocyclopentyl)amide building block in solution. Preferred protecting groups for solution phase chemistry are the Nα-tert-butoxycarbonyl group and the Nα-benzyloxycarbonyl group.

(g) Standard organic chemistry methods for the conversion of building block (f) towards compounds of general formula (I).

In the simplest example, the entire left hand portion of an inhibitor of general formula (I) can be prepared in solution by traditional organic chemistry methods and coupled to building block (f) (see Scheme 9 exemplified by preparation and use of the (2-alkyl-4-oxo-tetrahydrofuran-3-yl)carbamic acid tert-butyl ester (30)).

Scheme 9.

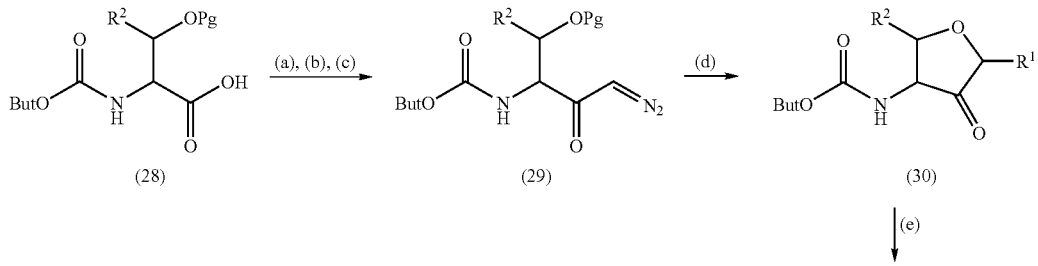

-continued

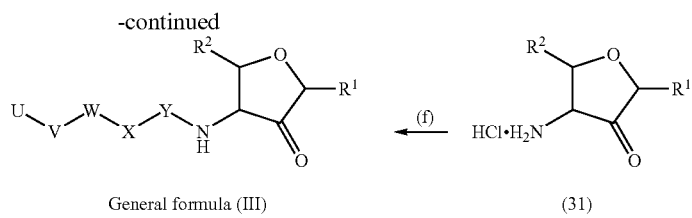

General formula (III)　　　(31)

(a) ⁱBuOCOCl, NMM, DCM, -15° C., 10 mins, under argon. (b) Diazomethane in diethyl ether, -15° C. to RT over 1hr. (c) Acetic acid (d) LiCl (10eq) in 80%aq acetic acid, 5° C. to RT over 1 hr.
(e) 4M HCl in dioxan, 0° C., 2 hrs. (f) Pre-prepared U—V—W—X—Y—COOH/HBTU/HOBt/NMM, DMR, RT, o/n.

The general strategy detailed in Scheme 9 is particularly useful when the compound of general formula (I) contains a substituent that is labile to trifluoroacetic acid, this being the final reagent used in each of the solid phase Schemes 3–8. For example (Scheme 10), treatment in solution of α-hydroxyacid (32) with sodium hydride in a dimethylformamide/dichloromethane mixture followed by addition of 4-tert-butylbenzyl bromide, provides 2RS-(4-tert-butylbenzyloxy)-4-methylpentanoic acid (33). Coupling of (33) to hydrochloride salt (31), provides (34), an example of general formula (I) where $R^3$='H', $(X)_o$='-', $(W)_n$='O', n=1, $(V)_m$='CH$_2$', i.e. $R^{12}$, $R^{13}$='H', m=1 and U=4-tert-butylphenyl. To those skilled in the practices of organic synthesis, 4-tert-butylbenzyl bromide may be replaced by any reasonable Ar—$CR^{12}R^{13}$-halogen, providing many variations of carboxylic acid (33) under the conditions shown. Thus analogues of (34) exploring a wide range of $(V)_m$ and U in general formula (I) may be prepared through the conditions detailed in Scheme 10.

Scheme 10.

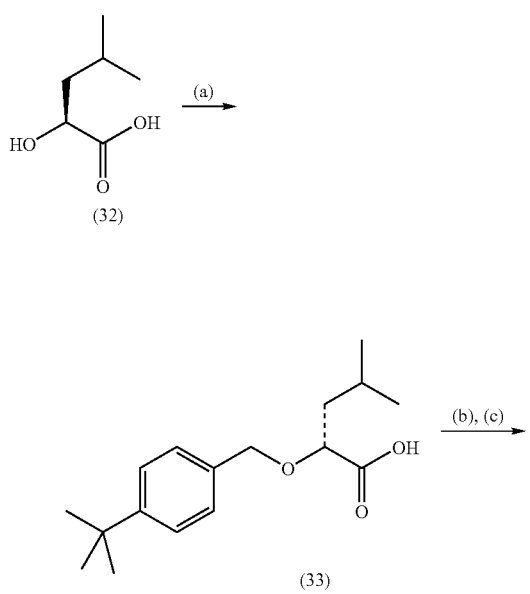

-continued

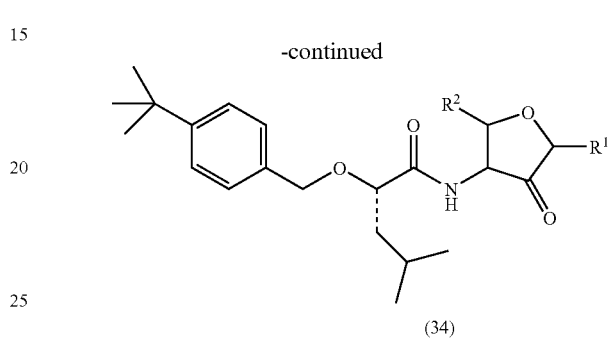

(34)

General formula (I) where
$R^3$ = 'H'
$(X)_0$ = '-'
$(W)_n$ = 'O', n = 1
$(V)_m$ = 'CH$_2$', i.e. $R^{12}$, $R^{13}$ = 'H', m = 1
U = 4-tert-butylphenyl
Z = 'O'

(a) 2.2eq NaH, 1:1 DMF/DCM, 1.25eq 4-tert-benzylbromide, 2 hr
(b) ⁱBuOCOCl, MNN, DCM, -15° C., 1 hr, under nitrogen.
(c) 1eq (31), NMM, RT, o/n.

A third strategy for the synthesis of compounds of general formula (I) where the addition of U-V-W-X-Y to the protected (2-alkyl-4-oxo-tetrahydrofuran-3-yl)amide or a (2-alkyl-4-oxo-tetrahydrothiophen-3-yl)amide or a (2-alkyl-5-oxocyclo pentyl)amide building block involves multistep organic reactions comprises:—

(h) Preparation of an appropriately functionalised and protected (2-alkyl-4-oxo-tetrahydrofuran-3-yl)amide or a (2-alkyl-4-oxo-tetrahydrothiophen-3-yl)amide or a (2-alkyl-5-oxocyclopentyl)amide building block in solution. Preferred protecting groups for solution phase chemistry are the Nα-tert-butoxycarbonyl group and the Nα-benzyloxycarbonyl group.

(i) Protection of the ketone functionality of the (2-alkyl-4-oxo-tetrahydrofuran-3-yl)amide or a (2-alkyl-4-oxo-tetrahydrothiophen-3-yl)amide or a (2-alkyl-5-oxocyclopentyl)amide building block e.g. as a dimethylacetal. Alternatively, the ketone may be reduced to the achiral secondary alcohols and re-oxidised as the final synthetic step.

(j) Standard organic chemistry methods for the conversion of building block (i) towards compounds of general formula (I).

Intermediates may be prepared in solution, followed by coupling to building block (i) and further derivitisation towards compounds of general formula (I) (see Scheme 11 exemplified by preparation and use of the (4-Hydroxy-2-alkyl-tetrahydrofuran-3-yl) carbamic acid tert-butyl ester (35)).

Scheme 11.

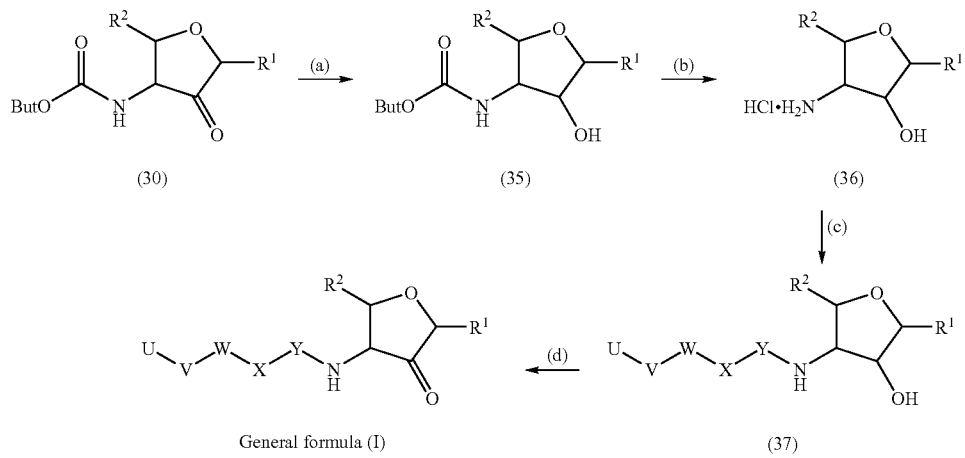

General formula (I)

(a) Reduction, e.g. NaBH$_4$ (b) 4M HCl in dioxan, 0° C., 2 hrs. (c) Stepwise reaction with intermediates of Y, then X, then W etc., to stepwise construct compounds (37). (d) Oxidation, e.g. Dess-Martin periodane, CH$_2$Cl$_2$.

Alternatively, depending upon the types of chemistry used to construct the left hand side U-V-W-X-Y of compounds of general formula (I), the ketone may require protection e.g. as the dimethyl acetal. Such a method is detailed and exemplified in Scheme 12 by the preparation and use of (4,4-Dimethoxy-2-alkyl-tetrahydrofuran-3-yl)-carbamic acid benzyl ester (38).

Scheme 12.

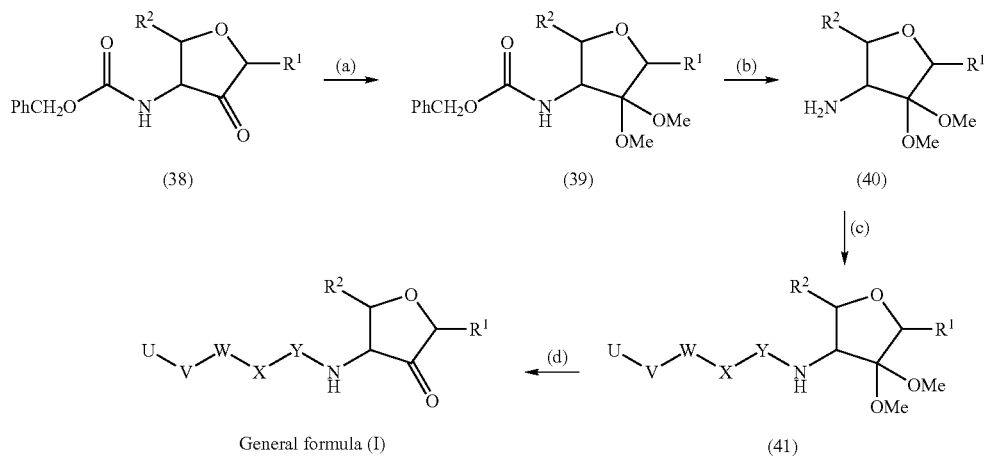

General formula (I)

(a) Triethylorthoformate/pTSA/MeOH. (b) H$_2$, Pd-C. (c) Stepwise reaction with intermediates of Y, then X, then W etc., to stepwise construct compounds (41). (d) Trifluoroacetic acid/CH$_2$Cl$_2$/H$_2$O.

The invention extends to novel intermediates as described above, and to processes for preparing compounds of general formula (I) from each of its immediate precursors. In turn, processes for preparing intermediates from their immediate precursors also form part of the invention.

Compounds of general formula (I) are useful both as laboratory tools and as therapeutic agents. In the laboratory certain compounds of the invention are useful in establishing whether a known or newly discovered cysteine protease contributes a critical or at least significant biochemical function during the establishment or progression of a disease state, a process commonly referred to as 'target validation'.

According to a second aspect of the invention, there is provided a method of validating a known or putative cys teine protease inhibitor as a therapeutic target, the method comprising:

(a) assessing the in vitro binding of a compound as described above to an isolated known or putative cysteine protease, providing a measure of potency; and optionally, one or more of the steps of:

(b) assessing the binding of the compound to closely related homologous proteases of the target and general housekeeping proteases (e.g. trypsin) to provides a measure of selectivity;

(c) monitoring a cell-based functional marker of a particular cysteine protease activity, in the presence of the compound; and (d) monitoring an animal model-based functional marker of a particular cysteine protease activity in the presence of the compound.

The invention therefore provides a method of validating a known or putative cysteine protease inhibitor as a therapeutic target. Differing approaches and levels of complexity are appropriate to the effective inhibition and 'validation' of a particular target. In the first instance, the method comprises assessing the in vitro binding of a compound of general formula (I) to an isolated known or putative cysteine protease, providing a measure of 'potency'. An additional assessment of the binding of a compound of general formula (I) to closely related homologous proteases of the target and general house-keeping proteases (e.g. trypsin) provides a measure of 'selectivity'. A second level of complexity may be assessed by monitoring a cell-based functional marker of a particular cysteine protease activity, in the presence of a compound of general formula (I). For example, a 'human osteoclast resorption assay' has been utilised as a cell-based secondary in vitro testing system for monitoring the activity of cathepsin K and the biochemical effect of protease inhibitors (e.g. see WO-A-9850533). An 'MHC-II processing—T-cell activation assay' has been utilised as a cell-based secondary in vitro testing system for monitoring the activity of cathepsin S and the biochemical effect of protease inhibitors (Shi, G-P., et al, *Immunity,* 10, 197–206, 1999). When investigating viral or bacterial infections such a marker could simply be a functional assessment of viral (e.g. count of mRNA copies) or bacterial loading and assessing the biochemical effect of protease inhibitors. A third level of complexity may be assessed by monitoring an animal model-based functional marker of a particular cysteine protease activity, in the presence of a compound of general formula (I). For example, murine models of *Leishmania* infection, *P. vinckei* infection, malaria (inhibition of falcipain) and *T. cruzi* infection (cruzipain), indicate that inhibition of cysteine proteases that play a key role in pathogen propagation is effective in arresting disease symptoms, 'validating' said targets.

The invention therefore extends to the use of a compound of general formula (I) in the validation of a known or putative cysteine protease inhibitor as a therapeutic target.

Compounds of general formula (I) are useful for the in vivo treatment or prevention of diseases in which participation of a cysteine protease is implicated.

According to a third aspect of the invention, there is provided a compound of general formula (I) for use in medicine, especially for preventing or treating diseases in which the disease pathology may be modified by inhibiting a cysteine protease.

According to a fourth aspect of the invention, there is provided the use of a compound of general formula (I) in the preparation of a medicament for preventing or treating diseases in which the disease pathology may be modified by inhibiting a cysteine protease.

Certain cysteine proteases function in the normal physiological process of protein degradation in animals, including humans, e.g. in the degradation of connective tissue. However, elevated levels of these enzymes in the body can result in pathological conditions leading to disease. Thus, cysteine proteases have been implicated in various disease states, including but not limited to, infections by *Pneumocystis carinii, Trypsanoma cruzi, Trypsanoma brucei brucei* and *Crithidia fsiculata*; as well as in osteoporosis, autoimmunity, schistosomiasis, malaria, tumour metastasis, metachromatic leukodystrophy, muscular dystrophy, amytrophy, and the like. See WO-A-9404172 and EP-A-0603873 and references cited in both of them. Additionally, a secreted bacterial cysteine protease from *S. Aureus* called staphylopain has been implicated as a bacterial virulence factor (Potempa, J., et al. *J. Biol. Chem,* 262(6), 2664–2667,1998).

The invention is useful in the prevention and/or treatment of each of the disease states mentioned or implied above. The present invention also is useful in a methods of treatment or prevention of diseases caused by pathological levels of cysteine proteases, particularly cysteine proteases of the papain superfamily, which methods comprise administering to an animal, particularly a mammal, most particularly a human, in need thereof a compound of the present invention. The present invention particularly provides methods for treating diseases in which cysteine proteases are implicated, including infections by *Pneumocystis carinii, Trypsanoma cruzi, Trypsanoma brucei, Leishmania mexicana, Clostridium histolyticum, Staphylococcus aureus*, foot-and-mouth disease virus and *Crithidia fusiculata*; as well as in osteoporosis, autoimmunity, schistosomiasis, malaria, tumour metastasis, metachromatic leukodystrophy, muscular dystrophy and amytrophy.

Inhibitors of cruzipain, particularly cruzipain-specific compounds, are useful for the treatment of Chagas' disease.

In accordance with this invention, an effective amount of a compound of general formula (I) may be administered to inhibit the protease implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine protease. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiacetals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

According to a fifth aspect of the invention, there is provided a pharmaceutical or veterinary composition comprising one or more compounds of general formula (I) and a pharmaceutically or veterinarily acceptable carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Formulations for oral administration in the present invention may be presented as: discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

According to a sixth aspect of the invention, there is provided a process for the preparation of a pharmaceutical or veterinary composition as described above, the process comprising bringing the active compound(s) into association with the carrier, for example by admixture.

Preferred features for each aspect of the invention are as for each other aspect *mutatis mutandis*.

The invention will now be illustrated with the following examples:

Solution Phase Chemistry—General Methods

All solvents were purchased from ROMIL Ltd (Waterbeach, Cambridge, UK) at SpS or Hi-Dry grade unless otherwise stated. General peptide synthesis reagents were obtained from Chem-Impex Intl. Inc. (Wood Dale Ill. 60191. USA). Thin layer chromatography (TLC) was performed on pre-coated plates (Merck aluminium sheets silica 60 F254, part no. 5554). Visualisation of compounds was achieved under ultraviolet light (254 nm) or by using an appropriate staining reagent. Flash column purification was performed on silica gel 60 (Merck 9385). All analytical HPLC were obtained on Phenomenex Jupiter $C_4$, 5μ, 300 A, 250×4.6 mm, using mixtures of solvent A=0.1% aq trifluoroacetic acid (TFA) and solvent B=90% acetonitrile/10% solvent A on automated Agilent systems with 215 and/or 254 nm UV detection. Unless otherwise stated a gradient of 10–90% B in A over 25 minutes at 1.5 mL/min was performed for full analytical HPLC analysis. HPLC-MS analysis was performed on an Agilent 1100 series LC/MSD, using automated Agilent HPLC systems, with a gradient of 10–90% B in A over 10 minutes on Phenomenex Columbus $C_8$, 5 μ, 300 A, 50×2.0 mm at 0.4 mL/min. Nuclear magnetic resonance (NMR) were obtained on a Bruker DPX400 (400 MHz 1H frequency; QXI probe) in the solvents and temperature indicated. Chemical shifts are expressed in parts per million (δ) and are referenced to residual signals of the solvent. Coupling constants (J) are expressed in Hz.

Example inhibitors (1–47) were prepared through a combination of solution chemistry and solid phase Fmoc-based chemistries (see 'Solid Phase Peptide Synthesis', Atherton, E. and Sheppard, R. C., IRL Press Ltd, Oxford, UK, 1989, for a general description) (Schemes 1–12).

Solid Phase Chemistry—General Methods

An appropriately protected and functionalised building block was prepared in solution (e.g. general compound (6), Scheme 1), then reversibly attached to the solid phase through an appropriate linker. Rounds of coupling/deprotection/chemical modification e.g. oxidation, were then performed until the full length desired molecule was complete (Scheme 2). Example inhibitors (1–47) were then released (cleaved) from the solid phase, analysed, purified and assayed for inhibition verses a range of proteases.

Generally, multipins (polyamide 1.2→10 µmole loadings, see www.mimotopes.com) were used for the solid phase synthesis, although any suitable solid phase surface could be chosen. In general, the 1.2 µmole gears were used to provide small scale crude examples for preliminary screening, whilst the 10 µmole crowns were used for scale-up synthesis and purification of preferred examples. Standard coupling and Fmoc deprotection methods were employed (see Grabowska, U. et al, *J. Comb. Chem.* 2(5), 475–490, 2000. for a thorough description of solid phase multipin methodologies).

Preparation of Initial Assembly

Building Block-linker constructs (e.g. (8), typically 100 mg to 2 g) were carboxyl activated with 2-(1H-benzotriazole-1-yl)-1,1,3,3-tetramethyluronium hexafluoro phosphate (HBTU, 1 mole equivalent), 1-hydroxybenzotriazole.hydrate (HOBT, 1 mole equivalent) and N-methylmorpholine (NMM, 2 mole equivalents) in dimethylformamide (DMF, typically 1 to 10 mL) for 5 minutes. Amino functionalised DA/MDA crowns or HEMA gears (10 µmole per crown/1.2 µmole per gear, 0.33 mole equivalent of total surface amino functionalisation compared to activated construct) were added, followed by additional DMF to cover the solid phase surface. The loading reaction was left overnight. Following overnight loading, crowns/gears were taken through standard cycles washing, Fmoc deprotection and loading quantification (see Grabowska, U. et al) to provide loaded Building Block-linker constructs (e.g. (9)). Analysis indicated virtually quantitative loading in all examples.

Coupling Cycles

The coupling of standard Fmoc-aminoacids and novel carboxylic acids (e.g. (12) Scheme 3, (16) Scheme 4, (19) Scheme 5, (22) Scheme 6, (25) Scheme 7) (10 or 20 mole equivalent) were performed via carboxyl activated with 2-(1H-benzotriazole-1-yl)-1,1,3,3-tetramethyluronium hexafluorophosphate (HBTU, 10 or 20 mole equivalent), 1-hydroxybenzotriazole.hydrate (HOBT, 10 or 20 mole equivalent) and N-methylmorpholine (NMM, 20 or 40 mole equivalents) in dimethylformamide, with pre-activation for 5 minutes. Activated species were dispensed to the appropriate wells of a polypropylene 96-well plate (Beckman, 1 mL wells, 500 µL solution per well for crowns or 250 µL solution per well for gears) in a pattern required for synthesis. Loaded free amino Building Block-linker constructs (e.g. (9)) were added and the coupling reaction left overnight. Following overnight coupling, crowns/gears were taken through standard cycles washing and Fmoc deprotection (see Grabowska, U. et al.). Identical activation and coupling conditions were used for the coupling of a range of carboxylic acids (R—COOH). Alternatively, chloroformates e.g. morpholine-4-carbonylchloride (10 mole equivalent), were coupled in DMF with the addition of NMM (10 mole equivalents).

Acidolytic Cleavage Cycle

A mixture of 95% TFA/5% water was pre-dispensed into two polystyrene 96-well plates (Beckman, 1 mL wells, 600 µL solution per well for crowns or 300 µL solution per well for gears) in a pattern corresponding to that of the synthesis. The completed multipin assembly was added to the first plate (mother plate), the block covered in tin foil and cleaved for 2 hours. The cleaved multipin assembly was then removed from the first plate and added to the second plate (washing plate) for 15 minutes. The spent multipin assembly was then discarded and the mother/washing plates evaporated on a HT-4 GeneVac plate evaporator.

Analysis and Purification of Cleaved Examples (a) Ex 1.2 µmole Gears. 100 µL dimethylsulphoxide (DMSO) was added to each post cleaved and dried washing plate well, thoroughly mixed, transferred to the corresponding post cleaved and dried mother plate well and again thoroughly mixed. 10 µL of this DMSO solution was diluted to 100 µL with a 90% acetonitrile/10% 0.1% aq TFA mixture. 20 µL aliquots were analysed by HPLC-MS and full analytical HPLC. In each case the crude example molecules gave the expected $[M+H]^+$ ion and an HPLC peak at >80% (by 215 nm UV analysis). This provided an approximately 10 mM DMSO stock solution of good quality crude examples for preliminary protease inhibitory screening.

(b) Ex 10 mole Crowns. 500 µL of a 90% acetonitrile/10% 0.1% aq TFA mixture was added to each washing plate well, thoroughly mixed, transferred to the corresponding mother plate well and again thoroughly mixed. 5 mL of this solution was diluted to 100 µL with a 90% acetonitrile/10% 0.1% aq TFA mixture. 20 µL aliquots were analysed by HPLC-MS and full analytical HPLC. In each case the crude example molecules gave the expected $[M+H]^+$ ion and an HPLC peak at >80% (by 215 nm UV analysis). The polystyrene blocks containing crude examples were then lyophilised.

(c) Individual examples (ex (b)) were re-dissolved in a 1:1 mixture of 0.1% aq TFA/acetonitrile (1 mL) and purified by semi-preparative HPLC (Phenomenex Jupiter $C_4$, 5µ, 300 A, 250×10 mm, a 25–90% B in A gradient over 25 mins, 4.0 mL/min, 215 nm UV detection). Fractions were lyophilised into pre-tarred glass sample vials to provide purified examples (typically 2 to 4 mg, 40 to 80% yield).

(d) Purified examples were dissolved in an appropriate volume of DMSO to provide a 10 mM stock solution, for accurate protease inhibitory screening.

EXAMPLE 1

(2S, 3S) 2-Benzyloxy-3-cyclohexyl-N-(2-methyl-4-oxo-tetrahydro furan-3-yl)-propionamide

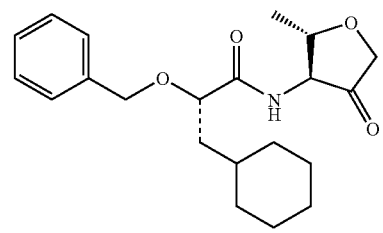

Following the general details from Scheme 1, the required bicycle building block (2S, 3S) (2-methyl-4-oxo-tetrahydrofuran-3-yl)-carbamic acid 9H-fluoren-9-ylmethyl ester (6a) was prepared as follows:

(1) Preparation of (1S, 1'S) [3-diazo-1-(1-tert-butoxyethyl)-2-oxo-propyl]-carbamic acid 9H-fluoren-9-ylmethyl ester.

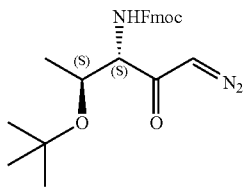

A solution of iso-butyl chloroformate (1.05 g, 7.7 mmol) in dichloromethane (14 ml) and a solution of 4-methylmorpholine (1.42 g, 14 mmol) in dichloromethane (14 ml) were simultaneously added to a stirred suspension of Fmoc-O-(tert-butyl ether)-L-allo-threonine (2.78 g, 7 mmol) in dichloromethane (70 ml) at −15° C. over 10 minutes under an atmosphere of nitrogen. Ethereal diazomethane [generated from diazald (7.14 g, ~21 mmol) addition in diethyl ether (115 ml) to sodium hydroxide (8.022 g) in water (11 ml)/ethanol (31 ml) at 60° C.] was then cautiously added and the resulting yellow solution was stirred at room temperature for 90 minutes. Acetic acid (~3 ml) was cautiously added (until effervescence had ceased) then the mixture was diluted with tert-butyl methyl ether (70 ml). The ethereal layer was washed with water (3×70 ml), dried ($Na_2SO_4$) and the solvent removed in vacuo to leave (1S, 1'S) [3-diazo-1-(1-tert-butoxyethyl)-2-oxo-propyl]-carbamic acid 9H-fluoren-9-ylmethyl ester as a yellow oil (5.47 g) which was used without further purification.

(2) Cyclisation to (2S, 3S) (2-methyl-4-oxo-tetrahydrofuran-3-yl)carbamic acid 9H-fluoren-9-ylmethyl ester.

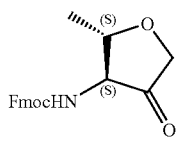

A solution of lithium chloride (2.97 g, 70 mmol) in 80% acetic acid in water (105 ml) was added to (1S, 1'S) [3-diazo-1-(1-tert-butoxyethyl)-2-oxo-propyl]carbamic acid 9H-fluoren-9-ylmethyl ester (5.7 g, ~7 mmol). The yellow oily suspension was stirred for 2 hours whereupon a pale yellow solution formed accompanied by the evolution of a gas. The solvents were removed in vacuo then the residue was dissolved in ethyl acetate (42 ml), washed with 10% aqueous sodium carbonate solution (2×42 ml) and saturated aqueous sodium chloride solution (42 ml). The combined aqueous layers were extracted with ethyl acetate (2×42 ml) then the combined ethyl acetate layers were dried ($Na_2SO_4$) and the solvents removed in vacuo to leave a yellow gum (4.28 g). The yellow gum was purified by chromatography over silica gel eluting with a gradient of n-heptane:ethyl acetate 9:1→7:3. Appropriate fractions were combined and the solvents removed in vacuo to leave (2S, 3S) (2-methyl-4-oxo-tetrahydrofuran-3-yl)carbamic acid 9H-fluoren-9-ylmethyl ester as a white crystalline solid (1.58 g, 67% from starting acid). TLC (single UV spot, Rf=0.27, n-heptane: ethyl acetate 2:1), analytical HPLC peak Rt=17.92 mins, HPLC-MS (single UV peak with Rt=8.47 mins, 360.0 [M+Na]$^+$, 361.0 [M+H+Na]$^+$).

$\delta$H (CDCl$_3$ at 298K); 1.28–1.50 (3H, C$\underline{H}_3$CHO, brs), 3.60–3.75 (1H, CH$_3$C$\underline{H}$O m), 3.78–4.00 (2H, Fmoc C$\underline{H}_2$, m), 4.04–4.24 (2H, Fmoc H-9 and NHC$\underline{H}$CO, m), 4.26–4.50 (2H, OC$\underline{H}_2$CO, dd), 4.92–5.14 (1H, N$\underline{H}$, brs), 7.17–7.36 (4H, ArH, Fmoc H-2, H-3, H-6 and H-7), 7.40–7.56 (2H, ArH, Fmoc H-1 and H-8), 7.60–7.75 (2H, ArH, Fmoc H-4 and H-5).

$\delta$C (CDCl$_3$ at 298K); 19.44 (u, $\underline{C}$H$_3$CHO), 47.52 (u, Fmoc C-9), 63.09 (u, NH$\underline{C}$HCO), 67.65 (d, Fmoc $\underline{C}$H$_2$), 71.20 (d, CO$\underline{C}$H$_2$), 77.82 (u, CH$_3$$\underline{C}$HO), 120.43 (u, Fmoc C-4 and C-5), 125.38 (u, Fmoc C-1 and C-8), 127.51 (u, Fmoc C-2 and C-7), 128.19 (u, Fmoc C-3 and C-6), 141.75 (q, Fmoc C4' and C-5'), 143.98/144.03 (q, Fmoc C-1' and C-8'), 156.42 (q, O$\underline{C}$ON), 212.18 (q, $\underline{C}$OCH$_2$).

Following the general details from Scheme 2, the required bicycle building (2S, 3S) (2-methyl-4oxo-tetrahydrofuran-3-yl)-carbamic acid 9H-fluoren-9-ylmethyl ester (6a) was converted to building block-linker construct (8a) as follows:

(2S, 3S) (2-methyl-4-oxo-tetrahydrofuran-3-yl)-carbamic acid 9H-fluoren-9-ylmethyl ester (6a) (354 mg, 1.05 mmol, 1 eq) was dissolved in a mixture of ethanol (9.6 mL) and water (1.4 mL) containing sodium acetate.trihydrate (218 mg, 1.6 mmol, 1.5 eq). 4-[[(hydrazinocarbonyl)amino] methyl]cyclohexanecarboxylic acid. trifluoroacetate (346 mg, 1.05 mmol, 1 eq, Murphy, A. M. et al., *J. Am. Chem. Soc.*, 114, 3156–3157, 1992) was added and the mixture refluxed for 2 hr. Chloroform (100 mL) was added and the organics washed with dilute aqueous hydrochloric acid (0.1 M, 1×100 mL). The acidic layer was backwashed with chloroform (3×100 mL) and the combined organics washed with brine (100 mL), dried ($Na_2SO_4$) and evaporated under reduced pressure to afford linker construct (8a) as a white solid (630 mg). Analytical HPLC indicated one main peak at $R_f$=17.17 min, HPLC-MS (main UV peak with $R_t$=7.91 min, 535.3 [M+H]$^+$. Crude (8a) was used directly for construct loading.

Following the general details from Scheme 2, the required building block-linker construct (8a) was attached to the solid phase providing loaded building block-linker construct (9a) as follows:

Building block-linker construct (8a) (1.0 mmole), 2-(1H-benzotriazole-1-yl)-1,1,3,3-tetramethyluroniumhexafluoro phosphate (HBTU, 379 mg, 1.0 mmole), 1-hydroxybenzotriazole.hydrate and (HOBT, 153 mg, 1.0 mmole) were dissolved in dimethylformamide (5 mL) and N-methylmorpholine (NMM, 220 μL, 2.0 mmole) added. After pre-activation for 5 minutes, free amine gears (250×1.2 μmole) were added, followed by dimethylformamide (30 mL) and left overnight. The spent coupling solution was then added to free amine crowns (25×10 μmole) and left overnight. Standard washing and analyses indicated loading at >95%.

The required ether carboxylic acid building block 2RS-Benzyloxy-3-cyclohexylpropionic acid (compound (12), Scheme 3) was prepared as follows:

(1) Preparation of 3-Cyclohexyl-2S-hydroxypropionic acid (Compound (11) Scheme 3)

A solution of sodium nitrite (12.1 g, 175 mmol) in water (40 ml) was added dropwise to a stirred suspension of (S)-α-aminocyclohexanepropionic acid hydrate (5 g, 26.5 mmol) in 0.5M sulphuric acid (120 ml, 60 mmol) at 0° C. over 1.5 hours. The mixture was allowed to warm to ambient temperature over 20 hours. The product was extracted into diethyl ether (2×25 ml) then the ethereal layers were washed with saturated aqueous sodium chloride solution (2×25 ml), dried (Na₂SO₄) and the solvents removed in vacuo. The residue (5.3 g) was recrystallized from diethyl ether (10 ml) and heptane (25 ml) to give 3-cyclohexyl-2S-hydroxypropionic acid as a white solid, yield 2.4 g, (53%).

$\delta$H (400 MHz, CDCl₃ at 298K), 0.89–1.35 (5H, m) and 1.51–1.86 (7H, m) (OCHC$\underline{H}_2$ and cyclohexyl), 4.32 (1H, OC$\underline{H}$CH₂, m)

(2) Preparation of 2RS-Benzyloxy-3-cyclohexylpropionic acid (Compound (12) Scheme 3)

Sodium hydride (265 mg of 60% dispersion in oil, 6.6 mmol) was added in two portions to a stirred mixture of 3-cyclohexyl-2S-hydroxypropionic acid (0.52 g, 3.0 mmol), dimethylformamide (5 ml) and dichloromethane (5 ml) at 0° C. over 5 minutes. The mixture was stirred at 0° C. for 5 minutes then at ambient temperature for 45 minutes. Benzyl bromide (0.45 ml, 3.8 mmol) was added then the mixture stirred for 1 hour before adding dimethylformamide (5 ml). After stirring for 4 hours potassium iodide (50 mg, 0.3 mmol) was added. The mixture was stirred for 20 hours then heated at 55° C. for 1 hour then allowed to cool to ambient temperature and poured into water (15 ml). A saturated aqueous sodium chloride solution (5 ml) was added then the mixture was extracted with dichloromethane (5 ml then 10 ml) that was discarded. The aqueous layer was acidified using 1M hydrochloric acid (10 ml) then extracted with dichloromethane (2×10 ml). The dichloromethane layer was dried (MgSO₄) and the solvent removed in vacuo. The residue (0.55 g) was dissolved in dimethylformamide (8 ml) then cooled to 0° C. before adding sodium hydride (190 mg of 60% dispersion in oil, 4.75 mmol). The mixture was stirred for 30 minutes then polymer bound isocyanate (380 mg, 2 mmolNg⁻¹) added. The mixture was stirred for 2 hours at ambient temperature then poured into water (15 ml). 1M Hydrochloric acid (10 ml) was added then the product was extracted into dichloromethane (2×10 ml), dried (Na₂SO₄) and the solvent removed in vacuo. The residue was purified by flash chromatography over silica gel eluting with a gradient of methanol:dichloromethane 0:1→1:20. Appropriate fractions were combined and the solvents removed in vacuo to give 2RS-benzyloxy-3-cyclohexylpropionic acid as a colourless oil, yield 41 mg (5.2%). HPLC-MS (single main UV peak with Rt=9.47 mins, 261.2 [M−H]⁻, 285.2[M+Na]⁺, 547.3[2M+Na]⁺).

$\delta$H (400 MHz, CDCl₃ at 298K), 0.72–1.03 (2H, cyclohexane, m), 1.08–1.38 (3H, cyclohexane, m), 1.45–1.93 (6H+2Hβ, cyclohexane, m), 3.93–4.18 (1Hα, OC$\underline{H}$CO), 4.35–4.53 (1H, C$\underline{H}_2$O, d, J=11.52 Hz), 4.68–4.88 (1H, C$\underline{H}_2$O, d, J=11.54 Hz), 7.20–7.47 (5H, ArH, m), 9.36 (1H, O$\underline{H}$, brs).

Compound (12) was coupled under standard conditions to loaded building block-linker construct (9a) (following standard removal of Fmoc), then cleaved to provide EXAMPLE 1. The crude example was analysed (see general techniques). HPLC Rt=20.74 mins (>90%), HPLC-MS 360.2 [M+H]⁺, 741.4 [2M+Na]⁺.

The following examples (2–10) were prepared as detailed for EXAMPLE 1, coupling with the required carboxylic acid building blocks to provide the full length molecule.

EXAMPLE 2

(2S, 3S) 2-Benzyloxy-N-(2-methyl-4-oxo-tetrahydrofuran-3-yl)-3-phenyl-propionamide

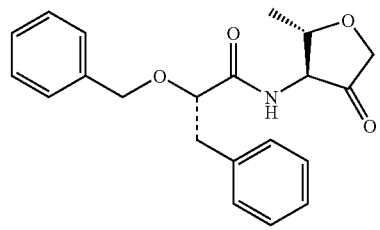

HPLC Rt=18.34 mins (>90%), HPLC-MS 354.2 [M+H]⁺, 729.3 [2M+Na]⁺.

The required carboxylic acid, 2RS-benzyloxy-3-phenylpropionic acid was prepared following the general method described for compound (12) as a colourless oil, yield 62 mg. HPLC-MS (single main UV peak with Rt=8.27 mins, 257.1 [M+H]⁺).

$\delta$H (CDCl₃ at 298K); 3.05–3.30 (2H, PhC$\underline{H}_2$, m), 4.15–4.30 (1H, OC$\underline{H}$CO, m), 4.36–4.50 (1H, C$\underline{H}_2$O, d, J=11.83 Hz), 4.66–4.83 (1H, C$\underline{H}_2$O, d, J=11.85 Hz), 7.13–7.45 (10H, ArH, m), 10.07 (1H, O$\underline{H}$, brs).

EXAMPLE 3

(2S, 3S) 3-Cyclohexyl-2-(furan-2-ylmethylsulfanyl)-N-(2-methyl-4-oxo-tetrahydrofuran-3-yl)-propionamide

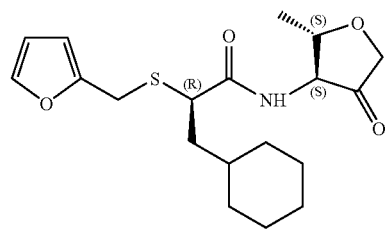

HPLC Rt=19.74 mins (>80%), HPLC-MS 366.1 [M+H]⁺, 753.2 [M+Na]⁺.

The required ether carboxylic acid building block 3-Cyclohexyl-2R-(furan-2-ylmethylsulfanyl)-propionic acid (compound (16), Scheme 4) was prepared as follows:

(1) Preparation of (S)-α-bromocyclohexanepropionic acid

A solution of sodium nitrite (2.26 g, 32.7 mmol) in water (6 ml) was added drop-wise at 0° C. over 4 hours to a stirred mixture of (s)-α-aminocyclohexanepropionic acid (5 g, 29.2 mmol), potassium bromide (11.40 g, 95.8 mmol) and concentrated sulphuric acid (3.3 ml) in water (35 ml). The mixture was stirred for 5 hours at 0° C. then at ambient temperature for 16 hours. The product was extracted into diethyl ether (4×50 ml) then the combined ethereal layers were washed with saturated aqueous sodium chloride solution (2×50 ml), dried (MgSO₄) and the solvent removed in vacuo. The residue was purified by chromatography over silica gel eluting with a gradient of methanol:dichloromethane 1:50→1:20. Appropriate fractions were combined and the solvents removed in vacuo to leave (S)-α-bromocyclohexanepropionic acid as a pale yellow oil (3.64 g, 53%). TLC (single spot, Rf=0.45, 10% methanol in dichloromethane), HPLC-MS (single main peak with Rt=8.85 mins, 234.1/236.1 [M+H]⁺).

$\delta$H (CDCl₃ at 298K); 0.83–1.88 (11H, C$\underline{H}$(cyclohexane), C$\underline{H}_2$(cyclohexane), m), 1.89–2.05 (2H, BrCHC$\underline{H}_2$, m), 4.32–4.44 (1H, BrC$\underline{H}$CH₂ (cyclohexane), m). $\delta$C (CDCl₃ at 298K); 26.19/26.29/26.48/26.58/26.79, 32.51 and 34.28 (cyclohexane $\underline{C}$H₂), 33.32 ($\underline{C}$HCH₂CHCO), 42.40 (BrCH$\underline{C}$H₂), 68.83 (Br$\underline{C}$H), 176.01 ($\underline{C}$O).

(2) Preparation of 3-Cyclohexyl-2R-(furan-2-ylmethylsulfanyl)-propionic acid (compound (16), Scheme 4)

(S)-α-bromocyclohexanepropionic acid (0.41 g, 1.75 mmol) and furan-2-ylmethylthiol (0.2 g, 1.75 mmol) were dissolved in dimethylformamide (10 ml) and purged with nitrogen for 10 minutes. The solution was cooled to 0° C. then triethylamine (0.244 ml, 1.75 mmol) was added dropwise over 1 minute. The mixture was stirred at 0° C. for 30 minutes then at ambient temperature for 16 hours. The solvent was removed in vacuo, and the residue purified by chromatography over gel silica using methanol:dichloromethane 1:100 as eluent. Appropriate fractions were combined and the solvents removed in vacuo to leave 3-Cyclohexyl-2R-(furan-2-ylmethylsulfanyl)-propionic acid (16) as a light brown oil (86 mg, 18%). Analytical HPLC peak Rt=18.68 mins. TLC (single spot, Rf=0.45, 10% methanol in dichloromethane), HPLC-MS (single main peak with Rt=9.43 mins, 291.1 [M+Na]⁺).

$\delta$H (CDCl₃ at 298K); 0.67–0.88 (2H, C$\underline{H}_2$(cyclohexane), m), 0.98–1.76 (11H, C$\underline{H}$(cyclohexane), C$\underline{H}_2$(cyclohexane), m), 3.20–3.32 (1H, SC$\underline{H}$CO, t, J=7.8 Hz), 3.69–3.79 (1H, C$\underline{H}_2$S, d, J=14.7 Hz), 3.85–3.95 (1H, C$\underline{H}_2$S, d, J=14.7 Hz), 6.14/6.28 (2H, furan H-3 and H-4, d), 7.30 (1H, furan H-5, s).

$\delta$C (CDCl₃ at 298K); 26.26/26.45/26.58/26.77/26.89, 28.66, 33.11 and 33.34 (each d, cyclohexane $\underline{C}$H₂ and SCH$\underline{C}$H₂), 35.52 (u, $\underline{C}$HCH₂CHS), 38.49 (d, S$\underline{C}$H₂), 43.84 (u, SCH), 108.64 (u, furan C-3), 110.78 (u, furan C-4), 142.65 (u, furan C-5), 150.02 (q, furan C-2), 177.63 (q, $\underline{C}$O).

EXAMPLE 4

(2S, 3S) 3-Cyclohexyl-2-(furan-2-ylmethylsulfanyl)-N-(2-methyl-4-oxo-tetrahydrofuran-3-yl)-propionamide

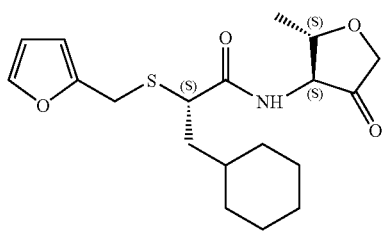

HPLC Rt=19.74 mins (>80%), HPLC-MS 366.1 [M+H]⁺, 753.2 [M+Na]⁺.

The required ether carboxylic acid building block 3-Cyclohexyl-2S-(furan-2-ylmethylsulfanyl)-propionic acid (inverted isomer of compound (16), Scheme 4) was prepared as follows:

(1) Preparation of (R)-α-bromocyclohexanepropionic acid

A solution of sodium nitrite (0.45 g, 6.5 mmol) in water (1.2 ml) was added dropwise at 0° C. over 4 hours to a stirred mixture of (R)-α-aminocyclohexanepropionic acid (1 g, 5.8 mmol), potassium bromide (2.3 g, 19.2 mmol) and concentrated sulphuric acid (0.66 ml) in water (7 ml). The mixture was stirred for 5 hours at 0° C. then at ambient temperature for 16 hours. The product was extracted into diethyl ether (4×20 ml) then the combined ethereal layers were washed with saturated aqueous sodium chloride solution (2×50 ml), dried (MgSO₄) and the solvent removed in vacuo. The residue was purified by chromatography over silica gel eluting with a gradient of methanol:dichloromethane 1:50→1:20. Appropriate fractions were combined and the solvents removed in vacuo to give (R)-α-bromocyclohexanepropionic acid as a pale yellow oil 0.374 g, (27%). TLC (single spot, Rf=0.45, 10% methanol in dichloromethane), HPLC-MS (single main peak with Rt=8.88 mins, 234.1/236.1 [M+H]⁺, 257.2/259.2 [M+Na]⁺).

$\delta$H (400 MHz, CDCl₃ at 298K), 0.83–1.88 (11H, C$\underline{H}$(cyclohexane), C$\underline{H}_2$ (cyclohexane), m), 1.89–2.05 (2Hβ, m), 4.32–4.44 (1Hα, m).

(2) Preparation of 3-Cyclohexyl-2S-(furan-2-ylmethylsulfanyl)-propionic acid (inverted isomer of compound (16), Scheme 4)

(R)-α-bromocyclohexanepropionic (0.37 g, 1.58 mmol) and furan-2-yl methanethiol (0.18 g, 1.58 mmol) were dissolved in dimethylformamide (10 ml) and purged with nitrogen for 10 minutes. The solution was cooled to 0° C. then triethylamine (0.22 ml, 1.58 mmol) was added dropwise over 1 minute. The mixture was stirred at 0° C. for 30 minutes then at ambient temperature for 16 hours. The solvent was removed in vacuo, and the residue purified by chromatography over gel silica using methanol dichloromethane 1:100 as eluent. Appropriate fractions were combined and the solvents removed in vacuo to give 3-Cyclohexyl-2S-(furan-2-ylmethylsulfanyl)-propionic acid as a light brown oil, yield 142 mg, (33%). Analytical HPLC peak Rt=18.68 mins. TLC (single spot, Rf=0.45, 10% methanol in dichloromethane), HPLC-MS (single main peak with Rt=9.53 mins, 291.0 [M+Na]⁺).

$\delta$H (400, CDCl₃ at 298K), 0.68–0.89 (2H, C$\underline{H}_2$(cyclohexane), m), 0.97–1.77 (11H, C$\underline{H}$(cyclohexane), C$\underline{H}_2$(cyclohexane), m), 3.21–3.32 (1Hα, t, J=7.8 Hz), 3.69–3.79 (1H, C$\underline{H}_2$S, d, J=14.8 Hz), 3.84–3.94 (1H, C$\underline{H}_2$S, d, J=14.8 Hz), 6.15/6.28 (2H, furan H-3 and H-4, d), 7.30 (1H, furan H-5, s).

EXAMPLE 5

(2S, 3S) 3-Cyclohexyl-2-(furan-2-ylmethanesulfonyl)-N-(2-methyl-4-oxo-tetrahydrofuran-3-yl)-propionamide

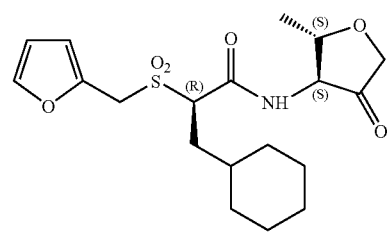

HPLC Rt=17.60 mins (>80%), HPLC-MS 398.1 [M+H]⁺, 817.1 [M+Na]⁺.

The intermediate loaded thioether (1.2 μmole gear) of EXAMPLE 3 was oxidised (Scheme 8) with m-chloroperbenzoic acid (5 eq, 65% reagent, 1.6 mg) in dichloromethane (200 μL) for 5 hrs, followed by standard washing and then cleaved to provide EXAMPLE 5.

EXAMPLE 6

(2S, 3S) 3-Cyclohexyl-2-(furan-2-ylmethanesulfonyl)-N-(2-methyl-4-oxo-tetrahydrofuran-3-yl)-propionamide

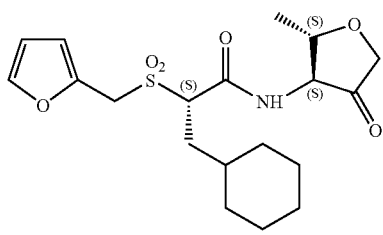

HPLC Rt=17.62 mins (>95%), HPLC-MS 398.1 [M+H]$^+$, 817.1 [M+Na]$^+$.

The intermediate loaded thioether (1.2 μmole gear) of EXAMPLE 4 was oxidised (Scheme 8) with m-chloroperbenzoic acid (5 eq, 65% reagent, 1.6 mg) in dichloromethane (200 μL) for 5 hrs, followed by standard washing and then cleaved to provide EXAMPLE 6.

EXAMPLE 7

(2S, 3S) 2-(4-tert-Butyl-phenylmethanesulfonyl)-4-methyl-pentanoic acid (2-methyl-4oxo-tetrahydrofuran-3-yl)-amide

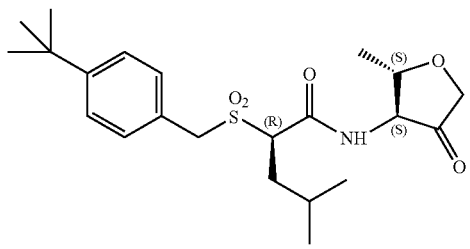

HPLC Rt=21.14 mins (>95%), HPLC-MS 424.2 [M+H]$^+$, 869.4 [2M+Na]$^+$.

The required carboxylic acid building block 2R-(4-tert-Butyl-benzylsulfanyl)-4-methyl-pentanoic acid (analogue of compound (16), Scheme 4) was prepared from (S)-2-bromo-4-methylpentanoic acid as follows:

(1) Preparation of (S)-2-bromo-4-methylpentanoic acid

A solution of sodium nitrite (5.1 g, 73 mmol) in water (15 ml) was added drop-wise at 0° C. over 5 hours to a stirred mixture of L-leucine (8.75 g, 67 mmol), potassium bromide (29.75 g, 0.25 mol) and concentrated sulphuric acid (8.6 ml) in water (100 ml). The mixture was stirred for 30 minutes at 0° C. then at ambient temperature for 20 hours. The product was extracted into diethyl ether (2×150 ml) then the combined ethereal layers were washed with saturated aqueous sodium chloride solution (2×100 ml), dried (MgSO$_4$) and the solvent removed in vacuo. The residue was purified by flash chromatography over silica gel eluting with a gradient of methanol:dichloromethane 1:50→1:20. Appropriate fractions were combined and the solvents removed in vacuo to leave (S)-2-bromomethylpentanoic acid as a colourless oil (2.22 g, 17%). TLC (single spot, Rf=0.2, methanol:dichloromethane 1:20).

$_δ$H (CDCl$_3$ at 298K); 0.95 and 0.99 (both 3H, CH$_3$CH, d, J=6.55 Hz), 1.77–1.89 (1H, CH$_3$CH, m), 1.93 (2H, CH$_2$H, m), 4.31 (1H, CHBr, t, J=7.7 Hz), 9.3 (1H, CO$_2$H, brs).

Additional (S)-2-bromo-4-methylpentanoic acid was obtained (6.55 g), however other components were observed by TLC analysis (methanol:dichloromethane 1:20).

(2) Preparation of 2R-(4-tert-butylbenzylsulfanyl)-4-methylpentanoic acid

A solution of (S)-2-bromo-4-methylpentanoic acid (1.1 g, 5.6 mmol) and [4-(tert-butyl)phenyl]methanethiol (1.0 g, 5.6 mmol) in dimethylformamide (15 ml) was purged with nitrogen for 5 minutes then cooled to 0° C. Triethylamine (0.79 ml, 5.7 mmol) was added drop-wise over 1 minute then the mixture was stirred for two days at ambient temperature. The solvents were removed in vacuo and residue purified by flash chromatography over silica gel eluting with a gradient of methanol:dichloromethane 0:1→1:20. Appropriate fractions were combined and the solvents removed in vacuo to leave a residue which was purified by flash chromatography over silica gel eluting with ethyl acetate:heptane 2:5. Appropriate fractions were combined and the solvents removed in vacuo to leave 2R-(4-tert-butylbenzylsulfanyl)-4-methylpentanoic acid as a colourless oil (200 mg, 12%). TLC (single spot, Rf=0.2, heptane: ethyl acetate 5:2), analytical HPLC with main peak Rt=22.117 mins, HPLC-MS (main UV peak with Rt=11.072 mins, 317.2 [M+Na]$^+$).

$_δ$H (CDCl$_3$ at 298K); 0.70 and 0.85 (both 3H, CH$_3$CH, d, J=6.3), 1.29 (9H, (CH$_3$)$_3$C, s), 1.44–1.51 (1H, CH$_3$CH, m), 1.62–1.75 (2H, CH$_2$CH, m), 3.15–3.20 (1H, SCH, m), 3.81 and 3.88 (both 1H, SCH$_2$, d, J=13.2 Hz), 7.25–7.35 (4H, aromatic).

The intermediate loaded thioether (1.2 μmole gear) was oxidised (Scheme 8) with m-chloroperbenzoic acid (5 eq, 65% reagent, 1.6 mg) in dichloromethane (200 μL) for 5 hrs, followed by standard washing and then cleaved to provide EXAMPLE 7.

EXAMPLE 8

(2S, 3S) Morpholine-4-carboxylic acid 2-cyclohexyl-1-(2-methyl-4-oxo-tetrahydro-furan-3-ylcarbamoyl)-ethyl ester

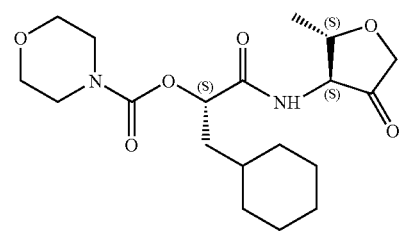

HPLC-MS 383.4 [M+H]$^+$.

The required carboxylic acid building block Morpholine-4carboxylic acid 1-carboxy-2-cyclohexyl-ethyl ester (compound (19), Scheme 5) was prepared as follows:

(1) Preparation of 3-cyclohexyl-2S-hydroxypropionic acid methyl ester. (Compound (18), Scheme 5)

Trimethylsilyl chloride (1.78 ml, 14.0 mmol) was added dropwise to a stirred solution of 3-cyclohexyl-2S-hydroxypropionic acid (compound (11) 1.31 g, 7.6 mmol) in methanol (35 ml). The mixture was stirred at room temperature for 20 hours then the solvents were removed in vacuo to leave a pale yellow oil (1.38 g). The crude oil was purified by chromatography over silica gel eluting with a gradient of n-heptane:ethyl acetate (4:1) Appropriate fractions were combined and the solvents removed in vacuo to give 3-cyclohexyl-2S-hydroxypropionic acid methyl ester as a colourless oil, yield 1.26 g, (89%). HPLC-MS (single main peak with Rt=7.43 mins, 187.14 [M+H]$^+$, 395.2 [2M+Na]$^+$).

$\delta$H (400 MHz, CDCl$_3$ at 298K), 0.84–1.04 (2H, CH$_2$(cyclohexane), m), 1.09–1.36 (3H, CH$_2$(cyclohexane), CH(cyclohexane), m), 1.45–1.77 (7H, CH$_2$(cyclohexane), CH(cyclohexane), m), 1.80–1.90 (1Hβ, m), 2.72 (1H, OH, d, J=5.99 Hz), 3.80 (3H, CH$_3$O, s), 4.20–4.31 (1Hα, m).

(2) Preparation of Morpholine-4-carboxylic acid 1-carboxy-2-cyclohexylethyl ester (Compound (18), Scheme 5)

A solution of phosgene (33.6 ml, 20% in toluene) was added to 3-cyclohexyl-2S-hydroxypropionic acid methyl ester (compound (11), 0.7 g, 4.03 mmol) followed by 6 drops of dimethylformamide. The mixture was stirred at ambient temperature for 16 hours then the solvents removed in vacuo. The residue was azeotroped with toluene (3×20 ml), and dissolved in anhydrous dichloromethane (11 ml). The solution was cooled to 0° C. then morpholine (0.86 g, 9.85 mmol) added. The mixture was stirred for 2 hours then partitioned between dichloromethane (30 ml) and 0.5M hydrochloric acid (30 ml). The dichloromethane layer was washed with saturated aqueous sodium hydrogen carbonate solution (30 ml), saturated aqueous sodium chloride solution (30 ml), dried (Na$_2$SO$_4$) and the solvent removed in vacuo. The residue was purified by chromatography over silica gel eluting with ethyl acetate:heptane 1:1. Appropriate fractions were combined and the solvents removed in vacuo to leave morpholine-4-carboxylic acid 2S-cyclohexyl-1-methoxycarbonylethyl ester (0.13 g, 10%) as an oil. A solution of lithium hydroxide monohydrate (17.5 mg, 0.418 mmol) in water (0.76 ml) was added to an iced-water chilled solution of morpholine-4-carboxylic acid 2-cyclohexyl-1-methoxycarbonylethyl ester (110 mg, 0.367 mmol) in dioxane (1.5 ml). The mixture was stirred at ambient temperature for 1 hour then diluted with water (10 ml). The aqueous layer was extracted with diethyl ether (2×110 ml) which was discarded, then acidified to pH=2 with 6M hydrochloric acid. The product was extracted into diethyl ether (2×10 ml), then the combined ethereal layers washed with saturated aqueous sodium chloride (10 ml), dried (MgSO$_4$) and the solvent removed in vacuo to give morpholine-4-carboxylic acid 1-carboxy-2-cyclohexylethyl ester as a white solid, yield 0.11 g, (100% from ester). TLC (single spot, Rf=0.20, methanol:dichloromethane 1:9), HPLC-MS (single main peak with Rt=7.614 mins, 286.2 [M+H]$^+$, 287.2 [M+2H]$^+$, 593.3 [2M+Na]$^+$).

$\delta$H (400 MHz, CDCl$_3$ at 298K), 0.75–1.00 (2H, CH$_2$(cyclohexane), m), 1.02–1.28 (4H, CH$_2$(cyclohexane), m), 1.33–1.46 (1H, CH(cyclohexane), m), 1.50–1.79 (6H, CH$_2$(cyclohexane), m), 3.28–3.73 (8H, CHOCH$_2$ and CH$_2$NCH$_2$, m), 4.92–5.02 (1Hα, m), 5.99 (1H, OH, brs).

EXAMPLE 9

(2S, 3S) 2-Cyclohexylmethyl-N-(2-methyl-4-oxo-tetrahydrofuran-3-yl)-4-morpholin-3 yl-4-oxo-butyramide

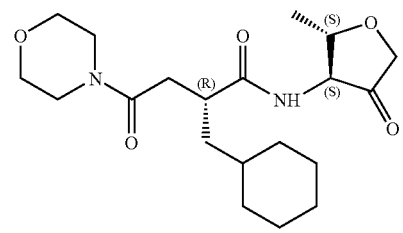

HPLC-MS 381.4 [M+H]$^+$.

The required carboxylic acid building 2R-cyclohexylmethyl-4-morpholin-4-yl-4-oxo-butyric acid (compound (22), Scheme 6) was prepared as follows:

(1) Preparation of 2R-cyclohexylmethyl-4-morpholin-4-yl-4-oxo-butyric acid methyl ester.

1-(3-dimethylaminopropyl)-3-ethylcarbodiimide.HCl (1.12 g, 5.69 mmol) then 1-hydroxybenzotriazole monohydrate (0.87 g, 5.69 mmol) were added to a stirred solution of 2R-(cyclohexylmethyl)succinic acid 1-methyl ester (compound (21), 1.0 g, 4.38 mmol) in dimethylformamide (10 ml) at 0° C. under argon. The mixture was stirred for 25 minutes then morpholine (0.7 ml, 8.76 mmol) was added drop-wise over 1 minute and stirring continued at ambient temperature for 16 hours. The product was extracted into ethyl acetate (200 ml) then washed with 1.0M hydrochloric acid (3×100 ml), saturated aqueous sodium hydrogen carbonate solution (3×100 ml), water (100 ml), then saturated aqueous sodium chloride solution (100 ml1), dried (MgSO4), and the solvent removed in vacuo to give 2R-cyclohexylmethyl-4-morpholin-4-yl-4-oxo-butyric acid methyl ester as an off-white solid, yield 1.22 g, (94%). HPLC-MS (single peak with Rt=7.91 mins, 298.1 [M+H]$^+$, 617.3 [2M+Na]$^+$).

(2) Preparation of 2R-cyclohexylmethyl-4-morpholinyl-4-oxo-butyric acid (Compound (22), Scheme 6).

A solution of lithium hydroxide monohydrate (0.51 g, 12.18 mmol) in water (27 ml) was added a stirred solution of 2R-cyclohexylmethyl-4-morpholin-4-yl-4-oxo-butyric acid methyl ester (1.21 g, 4.06 mmol) in tetrahydrofuran (55 ml) and methanol (27 ml) at 0° C. The mixture was stirred at ambient temperature for 1 hours then diluted with water (100 ml). The aqueous layer was extracted with diethyl ether (2×50 ml) which was discarded, then acidified to pH=1–2 with 1M hydrochloric acid. The product was extracted into dichloromethane (3×50 ml), then the combined ethereal layers washed with water (2×50 ml), saturated aqueous sodium chloride solution (2×50 ml), dried (MgSO$_4$) and the solvent removed in vacuo to leave a residue. The residue was purified by chromatography over silica gel eluting with a gradient of methanol:dichloromethane 1:100→3:100. Appropriate fractions were combined and the solvents removed in vacuo was to give 2R-cyclohexylmethyl-4-morpholin-4-yl-4-oxo-butyric acid (22) as a white solid, yield 0.82 g, (71%). HPLC-MS (single peak with Rt=6.769 mins, 284.2 [M+H]$^+$, 589.2 [2M+Na]$^+$).

$\delta$H (400 MHz, CDCl$_3$ at 298K), 0.77–0.90 (2H, CH$_2$(cyclohexane), m), 1.05–1.40 (4H, CH$_2$(cyclohexane), m), 1.50–1.90 (7H, CH(cyclohexane), CH₂(cyclohexane), m), 2.30–2.44 (2Hβ, m), 2.64–2.77 (1Hα, m), 2.96–3.10 (1H, OH, brs), 3.40–3.78 (8H, CH₂OCH₂ and CH₂NCH₂, m).

EXAMPLE 10

(2S, 3S) 2-Biphenyl-3-ylmethyl-pentanoic acid (2-methyl-4-oxo-tetrahydrofuran-3-yl)-amide

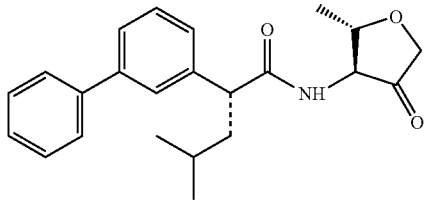

HPLC Rt=20.60 mins (>95%), HPLC-MS 366.1 [M+H]⁺, 753.2 [2M+Na]⁺.

The required carboxylic acid building block 2RS-Biphenyl-3-yl-4-methylpentanoic acid (compound (25), Scheme 7) was prepared as follows (1) Preparation of Biphenyl-3-yl-acetic acid methyl ester (Compound (24), Scheme 7)

Concentrated sulphuric acid (588 μL) was added to a solution of 3-bromophenyl acetic acid (10 g, 46.5 mmol) in methanol (100 mL). The mixture was refluxed for 1.5 h and then cooled to ambient temperature and evaporated under reduced pressure to afford a residue. The residue was redissolved in diethyl ether (500 mL), washed with water (2×100 mL), brine (100 mL), dried (MgSO₄) and then evaporated under reduced pressure to afford 3-bromophenyl acetic acid methyl ester (10.65 g). The 3-bromophenyl acetic acid methyl ester was dissolved in toluene (117 mL) then phenyl boronic acid (6.8 g, 55.69 mmol) added, followed by a aqueous solution of sodium carbonate (93 mL, 2M) and tetrakis(triphenylphosphine)palladium (1.6 g, 1.41 mmol). The mixture was stirred overnight then cooled to ambient temperature and an aqueous solution of saturated ammonium chloride (100 mL) added. The mixture was extracted with ethyl acetate (2×200 mL), died (Na₂SO₄) and evaporated under reduced pressure to afford a residue. Flash chromatography of the residue over silica (200 g) using ethyl acetate:heptane (3:48) as the eluent gave biphenyl-3-yl acetic acid methyl ester, yield 10.5 g, (99%), TLC (single UV spot, R$_f$=0.24, 10% ethyl acetate in heptane), analytical HPLC R$_t$=19.55 min, HPLC-MS (single main UV peak with R$_t$=9.35 min, 227.1 [M+H]⁺).

δH (400 MHz, CDCl₃ at 298K) 3.76 (2H, s, CH₂CO₂CH₃), 3.77 (3H, s, OCH₃), 7.34–7.66 (9H, m, biphenyl-3-yl).

(2) Preparation of Biphenyl-3-yl-acetic acid

Water (39 mL), followed by lithium hydroxide monohydrate (4.2 g, 101.5 mmol) were added to a solution of biphenyl-3-yl acetic acid methyl ester (11.43 g, 50.57 mmol) in methanol (265 mL). The mixture was stirred at ambient temperature for 2h then the organics were removed under reduced pressure. The mixture was acidified with dilute hydrochloric acid (1M, 80 mL), extracted with chloroform (2×100 mL), dried (MgSO₄) and evaporated under reduced pressure to afford biphenyl-3-yl acetic acid as a white solid, yield 10.6 g, (99%), analytical HPLC R$_t$=16.565 min, HPLC-MS (single main UV peak with R$_t$=7.91 min, 213.1 [M+H]⁺).

δH (400 MHz, CDCl₃ at 298K) 3.77 (2H, s, CH₂CO₂CH₃), 7.28–7.52 (9H, m, biphenyl-3-yl).

(3) Preparation of 2RS-Biphenyl-3-yl-4-methylpent-4-enoic acid

A solution of biphenyl-3-yl acetic acid (7.0 g, 33 mmol) in anhydrous tetrahydrofuran (84 mL) was added dropwise to a solution of lithium diisopropyl amide (36.4 mL, 2M solution in hexanes) in anhydrous tetrahydrofuran (84 mL) at –78° C. The mixture was allowed to warm to 0° C. and stirred for 40 min. The mixture was then cooled to –78° C. and 3-bromo-2-methylpropene (4.97 mL) rapidly added. The mixture was stirred for 1 h at –78° C. then water (28 mL) added and the organics removed under reduced pressure. The mixture was then acidified with hydrochloric acid (6M, 14 ml), extracted with ethyl acetate (3×100 ml), dried (MgSO4) and evaporated under reduced pressure to afford a residue. Flash chromatography of the residue over silica (400 g) using methanol:dichloromethane (3:97) as the eluent afforded impure 2-biphenyl-3-yl-4-methylpent-4-enoic acid (8.3 g). Flash chromatography over silica (400 g) using methanol:dichloromethane (1.5:98.5) afforded pure 2-biphenyl-3-yl-4-methylpent-4-enoic acid, yield 5.27 g, (60%), TLC (single UV spot, R$_f$=0.28, 5% methanol in dichloromethane), analytical HPLC R$_t$=19.99 min, HPLC-MS (single main UV peak with R$_t$=9.57 min, 267.1 [M+H]⁺).

δH (400 MHz, CDCl₃ at 298K), 1.765 (3H, s, CH₃), 2.53 (1H, dd, J=6.6 and 14.7 Hz, 3-H₁), 2.91 (1H, dd, J=8.9 and 14.7 Hz, 3-H₁), 3.92 (1H, dd, J=6.6 and 8.9 Hz, 2H), 4.79 (2H, d, J=10.7 Hz, 5-H₂), 7.30–7.62 (9H, m, biphenyl-3-yl).

(4) Preparation of 2RS-Biphenyl-3-yl-4-methylpentanoic acid (Compound (25), Scheme 7)

Palladium on carbon (10%, 300 mg) was added portionwise to a solution of 2RS-biphenyl-3-ylmethylpent-4-enoic acid (1 g, 3.76 mmol) in ethanol (40 mL) at 0° C. A hydrogen atmosphere was then introduced and the mixture allowed to warm to ambient temperature. The mixture was stirred for 18h, then the hydrogen atmosphere removed and the mixture filtered over Celite and the catalyst washed with ethanol (40 mL). The combined organic filtrate was concentrated under reduced pressure to afford a residue, which was flash chromatographed over silica (150 g) using methanol:dichloromethane (1:99) as the eluent to afford 2RS-biphenyl-3-yl-4-methylpentanoic acid, (25) yield 980 mg, (98%), TLC (single UV spot, R$_f$=0.45, 5% methanol in dichloromethane), analytical HPLC R$_t$=20.92 min, HPLC-MS (single main UV peak with R$_t$=10.15 min, 269.1 [M+H]⁺, 291.1 [M+Na]⁺). δH (400 MHz, CDCl₃ at 298K), 0.93 (6H, d, J=6.6 Hz, 2×CH₃), 1.52–1.57 (1H, m, 4-H₁), 1.71–1.76 (1H, m, 3-H₁), 1.97–2.05 (1H, m, 3-H₁), 3.66 (1H, t, J=7.8 Hz, 2-H₁), 7.32–7.60 (9H, m, biphenyl-3-yl).

EXAMPLE 11

(2R, 3s) 2-Benzyloxy-N-(2-methyl-4-oxo-tetrahydrofuran-3-yl)-3-phenyl-propionamide

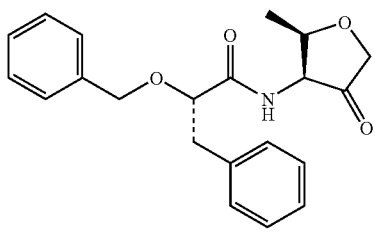

HPLC Rt=18.35 mins (>90%), HPLC-MS 354.2 [M+H]⁺, 729.3 [2M+Na]⁺.

Following the general details from Scheme 1, the required bicycle building block (2R, 3S) (2-methyl-4-oxo-tetrahydrofuran-3-yl)-carbamic acid 9H-fluoren-9-ylmethyl ester (6b) was prepared as follows:

(1) Preparation of (1S, 1'R) [3-diazo-1-(1-tert-butoxyethyl)-2-oxo-propyl]carbamic acid 9H-fluoren-9-ylmethyl ester.

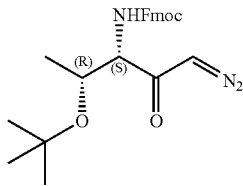

A solution of iso-butyl chloroformate (1.05 g, 7.7 mmol) in dichloromethane (14 ml) and a solution of 4-methylmorpholine (1.42 g, 14 mmol) in dichloromethane (14 ml) were simultaneously added to a stirred suspension of Fmoc-O-(tert-butyl ether)-L-threonine (2.78 g, 7 mmol) in dichloromethane (70 ml) at −15° C. over 10 minutes under an atmosphere of nitrogen. Ethereal diazomethane [generated from diazald (7.14 g, ~21 mmol) addition in diethyl ether (115 ml) to sodium hydroxide (8.022 g) in water (11 ml)/ethanol (31 ml) at 60° C.] was then cautiously added and the resulting yellow solution was stirred at room temperature for 90 minutes. Acetic acid (~3 ml) was cautiously added (until effervescence had ceased) then the mixture was diluted with tert-butyl methyl ether (70 ml). The ethereal layer was washed with water (3×70 ml), dried (Na₂SO₄) and the solvent removed in vacuo to leave (1S, 1'R) [3-diazo-1-(1-tert-butoxyethyl)-2-oxo-propyl]carbamic acid 9H-fluoren-9-ylmethyl ester as a yellow solid (4.28 g) which was used without further purification.

(2) Cyclisation to (ZR, 3S) (2-methyl-4-oxo-tetrahydrofuran-3-yl)-carbamic acid 9H-fluoren-9-ylmethyl ester.

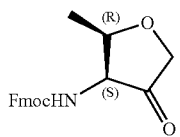

A solution of lithium chloride (2.97 g, 70 mmol) in 80% acetic acid in water (105 ml) was added to (1S, 1'R) [3-diazo-1-(1-tert-butoxyethyl)-2-oxo-propyl]carbamic acid 9H-fluoren-9-ylmethyl ester (4.28 g, ~7 mmol). The yellow oily suspension was stirred for 2 hours whereupon a pale yellow solution formed accompanied by the evolution of a gas. The solvents were removed in vacuo then the residue was dissolved in ethyl acetate (42 ml), washed with 10% aqueous sodium carbonate solution (2×42 ml) and saturated aqueous sodium chloride solution (42 ml). The combined aqueous layers were extracted with ethyl acetate (2×42 ml) then the combined ethyl acetate layers were dried (Na₂SO₄) and the solvents removed in vacuo to leave a yellow gum (3.44 g). The yellow gum was purified by chromatography over silica gel eluting with a gradient of n-heptane:ethyl acetate 9:1→7:3. Appropriate fractions were combined and the solvents removed in vacuo to leave (2R, 3S) (2-methyl-4-oxo-tetrahydrofuran-3-yl)-carbamic acid 9H-fluoren-9-ylmethyl ester as a white crystalline solid (2.92 g, 62% from starting acid). TLC (single UV spot, Rf=0.27, n-heptane:ethyl acetate 2:1), analytical HPLC peak Rt=17.96 mins, HPLC-MS (single UV peak with Rt=8.48 mins, 360.0 [M+Na]⁺, 361.0 [M+H+Na]⁺).

$\delta$H (CDCl₃ at 298K); 1.37–1.60 (3H, C$\underline{H}$₃CHO, brs), 3.68–3.86 (1H, CH₃C$\underline{H}$O m), 3.89–4.09 (2H, Fmoc C$\underline{H}$₂, m), 4.16–4.34 (2H, Fmoc H-9 and NHC$\underline{H}$CO, m), 4.36–4.57 (2H, OC$\underline{H}$₂CO, dd), 5.05–5.25 (1H, NH, brs), 7.28–7.47 (4H, ArH, Fmoc H-2 and H-7, ArH, Fmoc H-3 and H-6), 7.50–7.66 (2H, ArH, Fmoc H-1 and H-8), 7.73–7.85 (2H, ArH, Fmoc H-4 and H-5).

$\delta$C (CDCl₃ at 298K); 18.61 (u, $\underline{C}$H₃CHO), 46.69 (u, Fmoc C-9), 62.26 (u, NH$\underline{C}$HCO), 66.82 (d, Fmoc $\underline{C}$H₂), 70.38 (d, CO$\underline{C}$H₂), 76.93 (u, CH₃$\underline{C}$HO), 119.60 (u, Fmoc C-4 and C-5), 124.55 (u, Fmoc C-1 and C-8), 126.69 (u, Fmoc C-2 and C-7), 127.37 (u, Fmoc C-3 and C-6), 140.92 (q, Fmoc C-4' and C-5'), 143.15/143.20 (q, Fmoc C-1' and C-8'), 155.61 (q, O$\underline{C}$ON), 211.38 (q, $\underline{C}$OCH₂).

Following the general details from Scheme 2, the required bicycle building (2R, 3S) (2-methyl-4-oxo-tetrahydrofuran-3-yl)-carbamic acid 9H-fluoren-9-ylmethyl ester (6b) was converted to building block-linker construct (8b) as follows:

(2R, 3S) (2-methyl-4-oxo-tetrahydrofuran-3-yl)-carbamic acid 9H-fluoren-9-ylmethyl ester (6b) (354 mg, 1.05 mmol, 1 eq) was dissolved in a mixture of ethanol (9.6 mL) and water (1.4 mL) containing sodium acetate.trihydrate (218 mg, 1.6 mmol, 1.5 eq). 4-[[(hydrazinocarbonyl)amino]methyl]cyclohexanecarboxylic acid. trifluoroacetate (346 mg, 1.05 mmol, 1 eq, Murphy, A. M. et al, *J. Am. Chem. Soc.*, 114, 3156–3157, 1992) was added and the mixture refluxed for 2 hr. Chloroform (100 mL) was added and the organics washed with dilute aqueous hydrochloric acid (0.1 M, 1×100 mL). The acidic layer was backwashed with chloroform (3×100 mL) and the combined organics washed with brine (100 mL), dried (Na₂SO₄) and evaporated under reduced pressure to afford linker construct (8b) as a white solid (660 mg). Analytical HPLC indicated one main peak at $R_t$=17.011 min, HPLC-MS (main UV peak with $R_t$=7.96 min, 535.3 [M+H]⁺. Crude (8b) was used directly for construct loading.

Following the general details from Scheme 2, the required building block-linker construct (8b) was attached to the solid phase providing loaded building block-linker construct (9b) as follows:

Building block-linker construct (8b) (1.0 mmole), 2-(1H-benzotriazole-1-yl)-1,1,3,3-tetramethyluroniumhexafluoro phosphate (HBTU, 379 mg, 1.0 mmole), 1-hydroxybenzotriazole.hydrate and (HOBT, 153 mg, 1.0 mmole) were dissolved in dimethylformamide (5 mL) and N-methylmorpholine (NMM, 220 μL, 2.0 mmole) added. After pre-activation for 5 minutes, free amine gears (250×1.2 μmole) were added, followed by dimethylformamide (30 mL) and left overnight. The spent coupling solution was then added to free amine crowns (25×10 μmole) and left overnight. Standard washing and analyses indicated loading at >95%.

2RS-benzyloxy-3-phenylpropionic acid was coupled under standard conditions to loaded building block-linker construct (9b) (following standard removal of Fmoc), then cleaved to provide EXAMPLE 11. The crude example was analysed (see general techniques). HPLC Rt=18.35 mins (>90%), HPLC-MS 354.2 [M+H]$^+$, 729.3 [2M+Na]$^+$.

The following examples (12–23) were prepared as detailed for EXAMPLE 11, coupling with the required reagents to provide the full length molecule.

EXAMPLE 12

(2R, 3s) 4-Methyl-2-(4trifluoromethylbenzyloxy)-pentanoic acid (2-methyl-4-oxo-tetrahydrofuran-3-yl)-amide

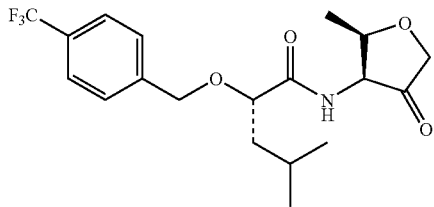

HPLC Rt=20.83 mins (>90%), HPLC-MS 388.2 [M+H]$^+$, 797.3 [2M+Na]$^+$.

The required carboxylic acid building block 2RS-4-methyl-2-(4-trifluoromethyl-benzyloxy)-pentanoic acid was prepared as follows (1) Preparation of 2RS-4-methyl-2-(4-trifluoromethyl-benzyloxy)-pentanoic acid Sodium hydride (333 mg of 60% dispersion in oil, 8.3 mmol) was added in two portions to a stirred mixture of (S)-2-hydroxy-4-methylpentanoic acid (0.5 g, 3.8 mmol), dimethylformamide (5 ml) and dichloromethane (5 ml) at 0° C. over 5 minutes. The mixture was stirred at 0° C. for 5 minutes then at ambient temperature for 45 minutes. 4-(trifluoromethyl)benzyl bromide (0.73 ml, 4.7 mmol) was added then the mixture stirred for 5 hours before adding potassium iodide (50 mg, 0.3 mmol) and dimethylformamide (5 ml). The mixture was stirred for 20 hours then heated at 55° C. for 1 hour then allowed to cool to ambient temperature and poured into water (15 ml). A saturated aqueous sodium chloride (5 ml) was added then the mixture was extracted with dichloromethane (5 ml then 10 ml) that was discarded. The aqueous layer was acidified using 1M hydrochloric acid (10 ml) then extracted with dichloromethane (2×10 ml). The dichloromethane layer was dried (MgSO$_4$) and the solvent removed in vacuo. The residue (0.52 g) was dissolved in dimethylformamide (5 ml) then cooled to 0° C. before adding sodium hydride (160 mg of 60% dispersion in oil, 4 mmol). The mixture was stirred for 30 minutes then polymer bound isocyanate (320 mg, 2 mmol Ng$^{-1}$) added. The mixture was stirred for 2 hours at ambient temperature then poured into water (15 ml). 1M Hydrochloric acid (10 ml) was added then the product was extracted into dichloromethane (2×10 ml), dried (Na$_2$SO$_4$) and the solvent removed in vacuo. The residue was purified by flash chromatography over silica gel eluting with a gradient of methanol:dichloromethane 0:1→1:20. Appropriate fractions were combined and the solvents removed in vacuo to leave 2RS-4-Methyl-2-(4-trifluoromethylbenzyloxy)-pentanoic acid, yield 121 mg (11%) as a colourless oil. HPLC-MS (single peak with Rt=9.66 mins, 291.1 [M+H]$^+$, 313.1 [M+Na]$^+$).

EXAMPLE 13

(2R, 3S) 3-Cyclohexyl-2-(furan-2-ylmethylsulfanyl)-N-(2-methyl-4-oxo-tetrahydrofuran-3-yl)-propionamide

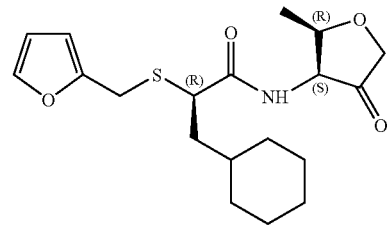

HPLC Rt=19.73 mins (>80%), HPLC-MS 366.1 [M+H]$^+$, 753.2 [M+Na]$^+$.

Prepared as detailed for EXAMPLE 3, but using loaded building block-linker construct (9b)

EXAMPLE 14

(2R, 3S) 3-Cyclohexyl-2-(furan-2-ylmethylsulfanyl)-N-(2-methyl-4-oxo-tetrahydrofuran-3-yl)-propionamide

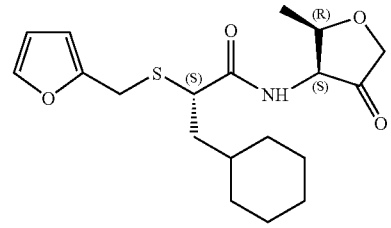

HPLC Rt=19.73 mins (>80%), HPLC-MS 366.1 [M+H]$^+$, 753.2 [M+Na]$^+$.

Prepared as detailed for EXAMPLE 4, but using loaded building block-linker construct (9b)

EXAMPLE 15

(2R, 3S) 2-(4-tert-Butyl-benzylsulfanyl)-4-methyl-pentanoic acid (2-methyl-4-oxo-tetrahydro-furan-3-yl)-amide

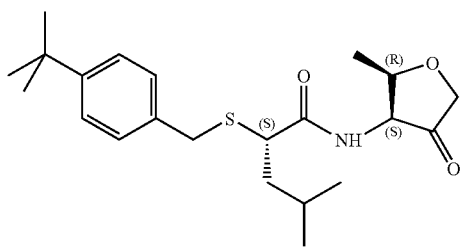

HPLC Rt=23.21 mins (>95%), HPLC-MS 392.2 [M+H]+, 805.4 [2M+Na]+.

The required carboxylic acid building block 2S-(4-tert-Butyl-benzylsulfanyl)-4-methyl-pentanoic acid (analogue of compound (16), Scheme 4) was prepared from (R)-2-bromo-4-methylpentanoic acid as follows:

(1) Preparation of 2R-Bromo-4-methylpentanoic acid

A solution of sodium nitrite (5.1 g, 73 mmol) in water (15 ml) was added drop-wise at 0° C. over 5 hours to a stirred mixture of D-leucine (8.75 g, 67 mmol), potassium bromide (29.75 g, 0.25 mol) and concentrated sulphuric acid (8.6 ml) in water (100 ml). The mixture was stirred for 30 minutes at 0° C. then at ambient temperature for 20 hours. The product was extracted into diethyl ether (2×150 ml) then the combined ethereal layers were washed with saturated aqueous sodium chloride solution (2×100 ml), dried (MgSO4) and the solvent removed in vacuo. The residue was purified by flash chromatography over silica gel eluting with a gradient of methanol: dichloromethane 1:50→1:20. Appropriate fractions were combined and the solvents removed in vacuo to leave 2R-bromo-4-methylpentanoic acid as a colourless oil, yield 1.60 g, (12.3%). TLC (single spot, Rf=0.2, methanol: dichloromethane 1:20). Additionally, a second crop (5.2 g, 40%) of slightly impure product was obtained $\delta_H$ (400 MHz, CDCl3 at 298K), 0.95 and 0.99 (both 3H, C$\underline{H}_3$CH, d, J=6.55 Hz), 1.77–1.89 (1H, CH3C$\underline{H}$, m), 1.93 (2Hβ, m), 4.31 (1Hα, t, J=7.7 Hz), 9.3 (1H, CO2$\underline{H}$, brs).

(2) Preparation of 2S-(4tert-butylbenzylsulfanyl)-4-methyl-pentanoic acid (analogue of compound (16), Scheme 4)

A solution of 2R-bromo-4-methylpentanoic acid (1.1 g, 5.6 mmol) and (4-(tert-butyl)phenyl)methanethiol (1.0 g, 5.6 mmol) in dimethylformamide (15 ml) was purged with nitrogen for 5 minutes then cooled to 0° C. Triethylamine (0.79 ml, 5.7 mmol) was added drop-wise over 1 minute then the mixture was stirred for two days at ambient temperature. The solvents were removed in vacuo and residue purified by flash chromatography over silica gel eluting with a gradient of methanol: dichloromethane 0:1→1:20. Appropriate fractions were combined and the solvents removed in vacuo to leave a residue which was purified by flash chromatography over silica gel eluting with ethyl acetate:heptane 2:5. Appropriate fractions were combined and the solvents removed in vacuo to give 2S-(4-tert-butylbenzylsulfanyl)-4-methylpentanoic acid as a colourless oil, yield 150 mg, (9%). TLC (single spot, Rf=0.2, heptane: ethyl acetate 5:2), analytical HPLC with main peak Rt=22.117 mins, HPLC-MS (main V peak with Rt=11.072 mins, 317.2 [M+Na]+).

$\delta_H$ (400 MHz, CDCl3 at 298K), 0.70 and 0.85 (both 3H, C$\underline{H}_3$CH, d, J=6.3), 1.29 (9H, (C$\underline{H}_3$)3C, s), 1.44–1.51 (1H, CH3C$\underline{H}$, m), 1.62–1.75 (2Hβ, m), 3.15–3.20 (1Hα, m), 3.81 and 3.88 (both 1H, SC$\underline{H}_2$, d, J=13.2 Hz), 7.25–7.35 (4H, aromatic).

EXAMPLE 16

(2R, 3S) 3-Cyclohexyl-2-(furan-2-ylmethanesulfonyl)-N-(2-methyl-4oxo-tetrahydrofuran-3-yl)-propionamide

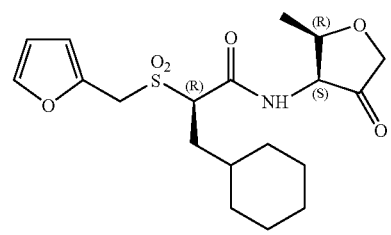

HPLC Rt=17.65 mins (>80%), HPLC-MS 398.1 [M+H]+, 817.1 [M+Na]+.

Prepared as detailed for EXAMPLE 5, but using loaded building block-linker construct (9b)

EXAMPLE 17

(2R, 3S) 3-Cyclohexyl-2-(furan-2-ylmethanesulfonyl)-N-(2-methyl-4-oxo-tetrahydrofuran-3-yl)-propionamide

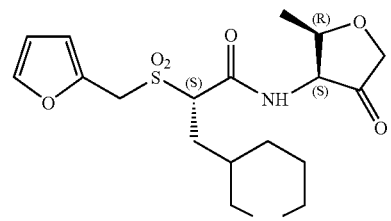

HPLC Rt=17.61 mins (>95%), HPLC-MS 398.1 [M+H]+, 817.1 [M+Na]+.

Prepared as detailed for EXAMPLE 6, but using loaded building block-linker construct (9b)

EXAMPLE 18

(2R, 3S) 2-(4-tert-Butyl-phenylmethanesulfonyl)-4-methyl-pentanoic acid (2-methyl-4-oxo-tetrahydro-furan-3-yl)-amide

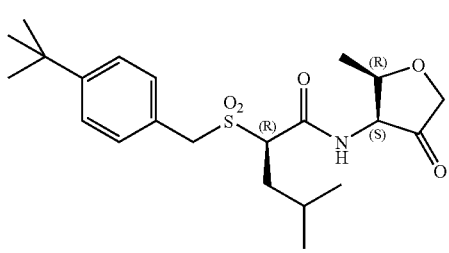

HPLC Rt=21.19 mins (>95%), HPLC-MS 424.2 [M+H]$^+$, 869.4 [2M+Na]$^+$.

Prepared as detailed for EXAMPLE 7, but using loaded building block-linker construct (9b)

EXAMPLE 19

(2R, 3S) Morpholin-4-carboxylic acid 2-cyclohexyl-1-(2-methyl-4-oxo-tetrahydro-furan-3-ylcarbamoyl)-ethyl ester

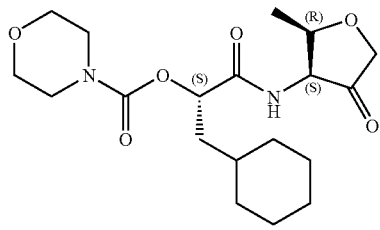

HPLC-MS 383.4 [M+H]$^+$.

Prepared as detailed for EXAMPLE 8, but using loaded building block-linker construct (9b)

EXAMPLE 20

(2R, 3S) 2-Cyclohexylmethyl-N-(2-methyl-4-oxo-tetrahydrofuran-3-yl)-4-morpholin-4-yl-4-oxo-butyramide

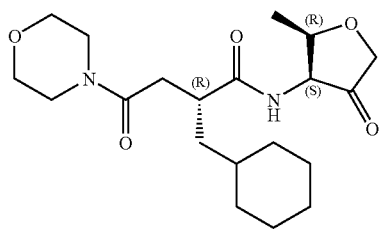

HPLC-MS 381.4 [M+H]$^+$.

Prepared as detailed for EXAMPLE 9, but using loaded building block-linker construct (9b)

EXAMPLE 21

(2R, 3S) 2-Biphenyl-3-yl-4-methyl-pentanoic acid (2-methyl-4-oxo-tetrahydrofuran-3-yl)-amide

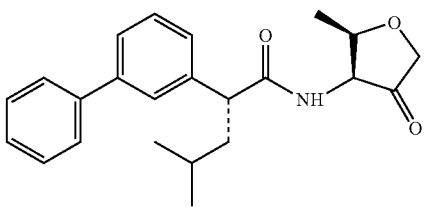

HPLC Rt=20.62 mins (>95%), HPLC-MS 366.1 [M+H]$^+$, 753.2 [2M+Na]$^+$.

Prepared as detailed for EXAMPLE 10, but using loaded building block-linker construct (9b)

EXAMPLE 22

(2R, 3S) 4-Methyl-2-[2-oxo-2-(3-phenyl-pyrrol-1-yl)-ethyl]-pentanoic acid (2-methyl-4-oxo-tetrahydrofuran-3-yl)-amide

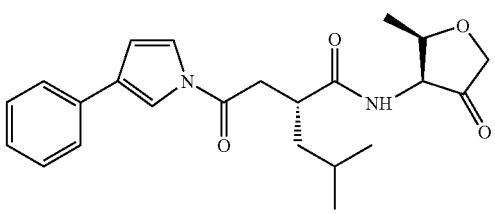

HPLC Rt=19.80 & 20.16 mins (19.9 & 80.1%), HPLC-MS 397.2 [M+H]$^+$, 815.4 [2M+Na]$^+$.

The required carboxylic acid building block (2R) 4-Methyl-2-[2-oxo-2-(3-phenyl-pyrrol-1-yl)-ethyl]-pentanoic acid (analogue of compound (22), Scheme 6) was as follows:

(1) Preparation of 4-Phenyl-1H-pyrrole-3-carboxylic acid methyl ester

A solution of 4-toluenesulphonylmethyl isocyanide (4.9 g, 25.2 mmol) and methyl trans-cinnamate (4.0 g, 24.7 mmol) in diethyl ether (40 ml) and dimethyl sulphoxide (20 ml) was added drop-wise over 30 minutes to a stirred suspension of sodium hydride (60% dispersion, 1.25 g, 31.3 mmol) in diethyl ether (100 ml) under nitrogen. After 20 minutes a further portion of dimethyl sulphoxide (25 ml) was added to the reaction vessel. The mixture was stirred for 1 hour then water (200 ml) was cautiously added. The product was extracted into dichloromethane (1×400 ml and 1×250 ml) then the combined dichloromethane layers were dried (Na$_2$SO$_4$) and the solvent removed in vacuo. The residue was purified by flash chromatography over silica gel eluting with a gradient of heptane:ethyl acetate:dichloromethane 2:1:0→1:1:1. Appropriate fractions were combined and the solvents removed in vacuo to leave 4-phenyl-1H-pyrrole-3-carboxylic acid methyl ester as a white solid (1.55 g, 31%). TLC (single spot, Rf=0.25, heptane:ethyl acetate 2:1), HPLC-MS (main UV peak with Rt=7.849 mins, 202.1 [M+H]$^+$, 425.1 [2M+Na]$^+$).

(2) Preparation of 3-Phenyl-1H-pyrrole

A solution of potassium hydroxide (4.3 g, 77 mmol) in water (40 ml) was added to a suspension of 4-phenyl-1H-pyrrole-3-carboxylic acid methyl ester (1.55 g, 7.7 mmol) in methanol (40 ml). The mixture was heated at reflux for 2.5 hours then the majority of solvents removed from the resulting solution by distillation in vacuo. The residue was diluted with water (100 ml) and ice (30 ml) added then the mixture was acidified with hydrochloric acid (1M) to pH=1. The precipitate was collected by filtration in vacuo then washed with water (75 ml), dichloromethane (75 ml), water (20 ml) then dichlororomethane (75 ml). The white solid was dried in vacuo then heated with ethanolamine (10 ml) at 190° C. under an atmosphere of nitrogen for 2.25 hours. The mixture was allowed to cool to ambient temperature then poured onto ice (150 ml). Water (50 ml) was added then the product was extracted into dichloromethane (3×50 ml). The dichloromethane layers were combined then dried (Na$_2$SO$_4$) and the solvent removed in vacuo to leave an oil (900 mg) which was purified by flash chromatography over silica gel eluting with ethyl acetate:heptane 1:5. Appropriate fractions were combined and the solvents removed in vacuo to leave 3-phenyl-1H-pyrrole as a yellow-green oil which solidified after storage at −80° C. for 20 hours (810 mg, 74%). TLC (single spot, Rf=0.25, heptane:ethyl acetate 5:1), HPLC-MS (single UV peak with Rt=8.493 mins, 144.1 [M+H]$^+$).

$\delta_H$ (CDCl$_3$ at 298K); 6.54, 6.80 and 7.06 (each 1H, pyrrole, m), 7.15–7.51 (5H, aromatic), 8.22 (1H, NH, brs)

(3) Preparation of (2R) Isobutyl-succinic acid

A solution of lithium hydroxide monohydrate (26 mg, 0.61 mmol) in water (250 μl) was added to a stirred solution of (2R) 2-isobutylsuccinic acid 1-methyl ester (100 mg, 0.53 mmol) in 1,4-dioxane (500 μl). The mixture was stirred for 2 hours then lithium hydroxide monohydrate (26 mg, 0.61 mmol) was added and stirring continued for 24 hours. The majority of solvents were removed by distillation in vacuo then the residue was dissolved in water (5 ml) and acidified using hydrochloric acid (1M) to pH=1. The product was extracted into dichloromethane (5×5 ml), dried (Na$_2$SO$_4$) and the solvent removed in vacuo to obtain (2R) 2-isobutylsuccinic acid (49 mg, 53%) as a solid. HPLC-MS (single UV peak with Rt=6.223 mins, 197.1 [M+Na]$^+$).

(4) Preparation of (2R) 4-Methyl-2-[2-oxo-2-(3-phenyl-pyrrol-1-yl)-ethyl]-pentanoic acid A solution of (2R)-2-isobutylsuccinic acid (35 mg, 0.2 mmol) in acetyl chloride (1.2 ml) was heated at reflux under nitrogen for 2.2 hours then volatile components removed by distillation in vacuo to leave (3R)-3-isobutyldihydrofuran-2,5-dione as an oily residue which was used without further purification.

Sodium hydride (12 mg of 60% dispersion in oil, 0.3 mmol) was added to a stirred solution of 3-phenylpyrrole (43 mg, 0.30 mmol) in tetrahydrofuran (1.0 ml) under nitrogen. The mixture was stirred for 15 minutes then added via cannula to a stirred solution of the (3R)-3-isobutyldihydrofuran-2,5-dione (0.2 mmol) in tetrahydrofuran (1.0 ml) at 0° C., then stirred for 5 hours. The majority of solvents were removed in vacuo then water (10 ml) added. The aqueous layer was extracted with ethyl acetate (5 ml) then saturated aqueous sodium chloride solution (5 ml) added and the aqueous layer extracted with an additional portion of ethyl acetate (5 ml). The aqueous layer was acidified using hydrochloric acid (1M) to pH=1 then the product extracted into ethyl acetate (2×5 ml), dried (MgSO$_4$) and the solvent removed in vacuo. The residue was purified by flash chromatography over silica gel eluting with a gradient of methanol:dichloromethane 1:99→3:17. Appropriate fractions were combined and the solvents removed in vacuo to leave a mixture (approximately 1:1) of (2R)-4-methyl-2-[oxo-2-(3-phenylpyrrol-1-yl)ethyl]pentanoic acid and (3S)-5-Methyl-3-(3-phenyl-pyrrole-1-carbonyl)-hexanoic acid (1.6 mg, 2%) as an oil. TLC (two spots, Rf=0.8 and Rf=0.75, methanol:dichloromethane 1:9), analytical HPLC two unresolved UV peaks with Rt=19.020 and 19.127 mins, HPLC-MS (two unresolved UV peaks with Rt=9.724 and 9.861 mins, 300.2 [M+H]$^+$, 621.3 [2M+Na]$^+$).

This mixture was used directly for the preparation of EXAMPLE 22.

EXAMPLE 23

(2R, 3S) 2-[2-(3,4-Dihydro-1H-isoquinolin-2-yl)-2-oxo-ethyl]4-methyl-pentanoic acid (2-methyl-4-oxo-tetrahydrofuran-3-yl)-amide

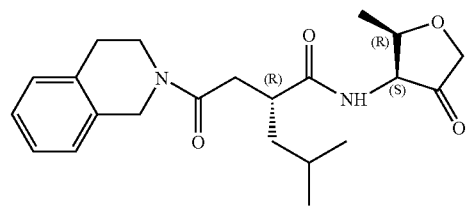

HPLC Rt=16.03 & 16.53 mins (>80%), HPLC-MS 387.2 [M+H]$^+$, 795.4 [2M+Na]$^+$.

The required carboxylic acid building block (2R) 2-[2-(3,4-Dihydro-1H-isoquinolin-2-yl)-2-oxo-ethyl]-4-methyl-pentanoic acid (analogue of compound (22), Scheme 6) was as follows:

(1) Preparation of 2-[2-(3,4-Dihydro-1H-isoquinolin-2-yl)-2-oxo-ethyl]-4-methyl-pentanoic acid methyl ester.

iso-Butyl chloroformate (33.64 mg, 0.2463 mmol) in dichloromethane (2 ml) and N-methyl morpholine (49.83 mg, 0.4927 mmol) in dichloromethane (2 ml) were simultaneously added to a stirred solution of (R)-2-isobutyl succinic acid 1-methyl ester (42.15 mg, 0.2239 mmol) in dichloromethane (2 ml) at −15° C. under argon over 5 minutes. The mixture was stirred at −15° C. for 15 minutes. A freshly prepared solution of 1,2,3,4-tetrahydro-isoquinoline (29.83 mg, 0.2239 mmol) in dichloromethane (2 ml) and N-methylmorpholine (24.92 mg, 0.2463 mmol) was then added dropwise. The mixture was then stirred at ambient temperature for 16 hours. The reaction mixture was poured into saturated aqueous sodium chloride solution (1 ml). The aqueous layer was extracted with diethyl ether (2×5 ml) which was discarded. The aqueous layer was acidified with 1M hydrochloric acid to pH (12), then the product was extracted into dichloromethane (3×5 ml). The combined dichloromethane layers were washed with water (2×5 ml), saturated aqueous sodium chloride solution (2×5 ml) then dried (Na$_2$SO$_4$). The solvent was removed in vacuo to give a residue which was purified over silica gel eluting with a gradient of n-heptane:ethyl acetate 4:1. Desired fractions were combined and reduced in vacuo to leave 2-[2-(3,4-Dihydro-1H-isoquinolin-2-yl)-2-oxo-ethyl]-4-methyl-pentanoic acid methyl ester as a colourless oil (35 mg, 51.5% from starting acid). TLC (single UV spot, Rf=0.6, n-heptane:ethyl acetate 1:1), HPLC-MS (single UV peak with Rt=9.544 mins, 304.2 [M+H]$^+$, 305.2 [M+2]$^+$, 306.2 [M+3]$^+$, 629.3 [2M+Na]$^+$.

(2) Preparation of 2-[2-(3,4-dihydro-1H-isoquinolin-2-yl)-2-oxo-ethyl]-4-methyl-pentanoic acid.

A solution of lithium hydroxide monohydrate (0.01452 g, 0.3461 mmol) in water (1.5 ml) was added drop-wise over 1 minute to a solution of 2-[2-(3,4-dihydro-1H-isoquinolin-2-yl)-2-oxo-ethyl]-4-methyl-pentanoic acid methyl ester (0.035 g, 0.1154 mmol) in tetrahydrofuran:methanol 2:1 (9 ml) at 0° C. The mixture was stirred at ambient temperature for 16 hours then poured into saturated aqueous sodium chloride solution (10 ml). The aqueous layer was extracted with diethyl ether (2×10 ml) which was discarded. The aqueous layer was acidified with 1M hydrochloric acid to pH (1~2), then the product was extracted into dichloromethane (3×10 ml). The combined dichloromethane layers were washed with water (2×10 ml), saturated aqueous sodium chloride solution (2×10 ml) then dried ($Na_2SO_4$) and the solvents removed in vacuo to leave 2-[2-(3,4-dihydro-1H-isoquinolin-2-yl)-2-oxo-ethyl]-4-methyl-pentanoic acid as a colourless oil (4.0 mg, 12%). TLC (main spot, Rf=0.2, methanol:dichloromethane 1:10), analytical HPLC Rt=13.297 min. HPLC-MS (290.2 [M+1]+, 312.2 [M+Na]+, 601.3 [2M+Na]+).

EXAMPLE 24

(2S, 3R) 2-Benzyloxy-N-(2-methyl-4-oxo-tetrahydrofuran-3-yl)-3-phenyl-propionamide

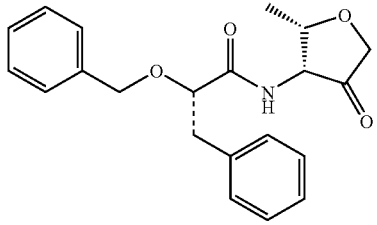

HPLC Rt=18.34 mins (>90%), HPLC-MS 354.2 [M+H]+.

Following the general details from Scheme 1, the required bicycle building block (2S, 3R) (2-methyl-4-oxo-tetrahydrofuran-3-yl)-carbamic acid 9H-fluoren-9-ylmethyl ester (6c) was prepared as follows:

(1) Preparation of (1R, 1'S) [3-diazo-1-(1-hydroxyethyl)-2-oxo-propyl]carbamic acid 9H-fluoren-9-ylmethyl ester.

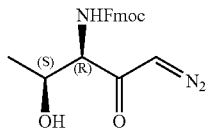

A solution of iso-butyl chloroformate (1.05 g, 7.7 mmol) in dichloromethane (7 ml) and a solution of 4-methylmorpholine (1.42 g, 14 mmol) in dichloromethane (7 ml) were simultaneously added to a stirred suspension of Fmoc-D-threonine (2.39 g, 7 mmol) in dichloromethane (70 ml) at −15° C. over 10 minutes under an atmosphere of nitrogen. Ethereal diazomethane [generated from diazald (7.14 g, ~21 mmol) addition in diethyl ether (115 ml) to sodium hydroxide (8.022 g) in water (11 ml)/ethanol (31 ml) at 60° C.] was then cautiously added and the resulting yellow solution was stirred at room temperature for 90 minutes. Acetic acid (~3 ml) was cautiously added (until effervescence had ceased) then the mixture was diluted with tert-butyl methyl ether (70 ml). The ethereal layer was washed with water (3×70 ml), dried ($Na_2SO_4$) and the solvent removed in vacuo to leave (1R, 1'S) [3-diazo-1-(1-hydroxyethyl)-2-oxo-propyl]carbamic acid 9H-fluoren-9-ylmethyl ester as a yellow solid (3.43 g) which was used without further purification.

(2) Cyclisation to (2S, 3R) (2-methyl-4-oxo-tetrahydrofuran-3-yl)carbamic acid 9H-fluoren-9-ylmethyl ester.

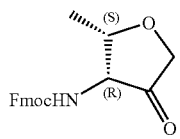

A solution of lithium chloride (2.97 g, 70 mmol) in 80% acetic acid in water (105 ml) was added to (1R, 1'S) [3-diazo-1-(1-hydroxyethyl)-2-oxo-propyl]carbamic acid 9H-fluoren-9-ylmethyl ester (3.43 g, ~7 mmol). The yellow oily suspension was stirred for 2 hours whereupon a pale yellow solution formed accompanied by the evolution of a gas. The solvents were removed in vacuo then the residue was dissolved in ethyl acetate (42 ml), washed with 10% aqueous sodium carbonate solution (2×42 ml) and saturated aqueous sodium chloride solution (42 ml). The combined aqueous layers were extracted with ethyl acetate (2×42 ml) then the combined ethyl acetate layers were dried ($Na_2SO_4$) and the solvents removed in vacuo to leave a yellow gum (2.26 g). The yellow gum was purified by chromatography over silica gel eluting with a gradient of n-heptane:ethyl acetate 9:1→7:3. Appropriate fractions were combined and the solvents removed in vacuo to leave (2S, 3R) (2-methyl-4-oxo-tetrahydrofuran-3-yl)carbamic acid 9H-fluoren-9-ylmethyl ester as a white crystalline solid (659 mg, 28% from starting acid). TLC (single UV spot, Rf=0.27, n-heptane:ethyl acetate 2:1), analytical HPLC peak Rt=18.02 mins, HPLC-MS (single UV peak with Rt=8.47 mins, 338.1 [M+H]+, 360.1 [M+Na]+, 361.0 [M+H+Na]+.

$\delta_H$ (CDCl$_3$ at 298K); 1.39–1.60 (3H, C$\underline{H}_3$CHO, brs), 3.72–3.85 (1H, CH$_3$C$\underline{H}$O m), 3.88–4.09 (2H, Fmoc C$\underline{H}_2$, m), 4.15–4.33 (2H, Fmoc H-9 and NHC$\underline{H}$CO, m), 4.39–4.58 (2H, OC$\underline{H}_2$CO, dd), 5.07–5.25 (1H, NH, brs), 7.28–7.38 (2H, ArH, Fmoc H-2 and H-7), 7.39–7.47 (2H, ArH, Fmoc H-3 and H-6), 7.52–7.66 (2H, ArH, Fmoc H-1 and H-8), 7.72–7.86 (2H, ArH, Fmoc H-4 and H-5).

$\delta_C$ (CDCl$_3$ at 298K); 19.45 (u, $\underline{C}$H$_3$CHO), 47.52 (u, Fmoc C-9), 63.09 (u, NH$\underline{C}$HCO), 67.65 (d, Fmoc $\underline{C}$H$_2$), 71.21 (d, CO$\underline{C}$H$_2$), 77.80 (u, CH$_3$$\underline{C}$HO), 120.43 (u, Fmoc C-4 and C-5), 125.38 (u, Fmoc C-1 and C-8), 127.51 (u, Fmoc C-2 and C-7), 128.20 (u, Fmoc C-3 and C-6), 141.75 (q, Fmoc C-4' and C-5'), 143.98/144.03 (q, Fmoc C-1' and C-8'), 156.45 (O$\underline{C}$ON), 212.21($\underline{C}$OCH$_2$).

Following the general details from Scheme 2, the required bicycle building (2S, 3R) (2-methyl-4-oxo-tetrahydrofuran-3-yl)-carbamic acid 9H-fluoren-9-ylmethyl ester (6c) was converted to building block-linker construct (8c) as follows:

(2S, 3R) (2-methyl-4-oxo-tetrahydrofuran-3-yl)-carbamic acid 9H-fluoren-9-ylmethyl ester (6c) (354 mg, 1.05 mmol, 1 eq) was dissolved in a mixture of ethanol (9.6 mL) and water (1.4 mL) containing sodium acetate.trihydrate (218 mg, 1.6 mmol, 1.5 eq). 4-[[(hydrazinocarbonyl)amino]methyl]cyclohexanecarboxylic acid. trifluoroacetate (346 mg, 1.05 mmol, 1 eq, Murphy, A. M. et al, *J. Am. Chem. Soc.*, 114, 3156–3157, 1992) was added and the mixture refluxed for 2 hr. Chloroform (100 mL) was added and the organics washed with dilute aqueous hydrochloric acid (0.1 M, 1×100 mL). The acidic layer was backwashed with chloroform (3×100 mL) and the combined organics washed with brine (100 mL), dried (Na$_2$SO$_4$) and evaporated under reduced pressure to afford linker construct (8c) as a white solid (660 mg). Analytical HPLC indicated one main peak at R$_t$=17.14 min, HPLC-MS (main UV peak with R$_t$=7.91 min, 535.3 [M+H]$^+$. Crude (8c) was used directly for construct loading.

Following the general details from Scheme 2, the required building block-linker construct (8c) was attached to the solid phase providing loaded building block-linker construct (9c) as follows:

Building block-linker construct (8c) (1.0 mmole), 2-(1H-benzotriazole-1-yl)-1,1,3,3-tetramethyluroniumhexafluoro phosphate (HBTU, 379 mg, 1.0 mmole), 1-hydroxybenzotriazole.hydrate and HOBT, 153 mg, 1.0 mmole) were dissolved in dimethylformamide (5 mL) and N-methylmorpholine (NMM, 220 µL, 2.0 mmole) added. After pre-activation for 5 minutes, free amine gears (250×1.2 µmole) were added, followed by dimethylformamide (30 mL) and left overnight. The spent coupling solution was then added to free amine crowns (25×10 µmole) and left overnight. Standard washing and analyses indicated loading at >95%.

Following the general details from Scheme 2, the required loaded building block-linker construct (9c) was elaborated on the solid phase as follows:

2RS-benzyloxy-3-phenylpropionic acid was coupled under standard conditions to loaded building block-linker construct (9c) (following standard removal of Fmoc), then cleaved to provide EXAMPLE 24. The crude example was analysed (see general techniques). HPLC Rt=18.34 mins (>90%), HPLC-MS 354.2 [M+H]$^+$.

The following examples (25–34) were prepared as detailed for EXAMPLE 24, coupling with the required reagents to provide the full length molecule.

EXAMPLE 25

(2S, 3R) N-(2-Methyl-4-oxo-tetrahydrofuran-3-yl)-3-phenyl-2-(4-trifluoromethylbenzyloxy)-propionamide

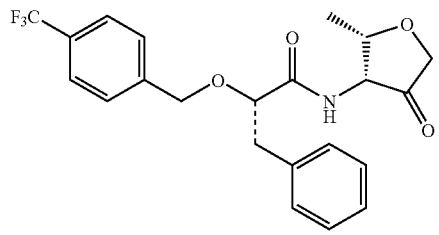

HPLC Rt=20.73 mins (>90%), HPLC-MS 422.1 [M+H]$^+$, 444.1 [M+Na]$^+$.

The required carboxylic acid, 2RS-3-Phenyl-2-(4-trifluoromethylbenzyloxy)-propionic acid was prepared following the general method described for compound (12) as a colourless oil, yield 12.7 mg. HPLC-MS (single main UV peak with Rt=9.59 mins, 325.1 [M+H]$^+$).

δ$_H$ (CDCl$_3$ at 298K); 2.80–3.17 (2H, PhCH$_2$, m), 3.90–4.14 (1H, OCHCO, m), 4.19–4.37 (1H CH$_2$O, d, J=12.57 Hz), 4.45–4.72 (1H, CH$_2$O, d, J=12.53 Hz), 6.85–7.46 (9H, ArH, m).

EXAMPLE 26

(2S, 3R) 2-Benzyloxy-3-cyclohexyl-N-(2-methyl-4-oxo-tetrahydro-furan-3-yl)-propionamide

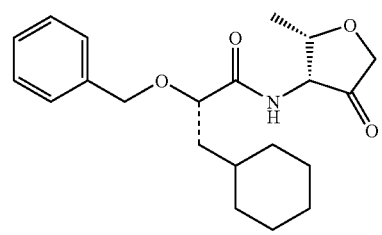

HPLC Rt=20.73 mins (>90%), HPLC-MS 360.2 [M+H]$^+$, 741.4 [2M+Na]$^+$.

Prepared as detailed for EXAMPLE 1, but using loaded building block-linker construct (9c)

EXAMPLE 27

(2S, 3R) 3-Cyclohexyl-2-(furan-2-ylmethylsulfanyl)-N-(2-methyl-4-oxo-tetrahydrofuran-3-yl)-propionamide

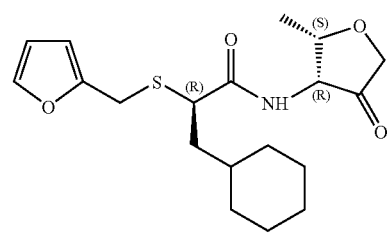

HPLC Rt=19.71 mins (>80%), HPLC-MS 366.1 [M+H]$^+$, 753.2 [M+Na]$^+$.

Prepared as detailed for EXAMPLE 3, but using loaded building block-linker construct (9c)

EXAMPLE 28

(2S, 3R) 3-Cyclohexyl-2-(furan-2-ylmethylsulfanyl)-N-(2-methyl-4-oxo-tetrahydrofuran-3-yl)-propionamide

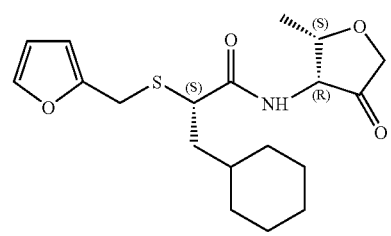

HPLC Rt=19.71 mins (>80%), HPLC-MS 366.1 [M+H]$^+$, 753.2 [M+Na]$^+$.

Prepared as detailed for EXAMPLE 4, but using loaded building block-linker construct (9c)

EXAMPLE 29

(2S, 3R) 3-Cyclohexyl-2-(furan-2-ylmethanesulfonyl)-N-(2-methyl-4-oxo-tetrahydrofuran-3-yl)-propionamide

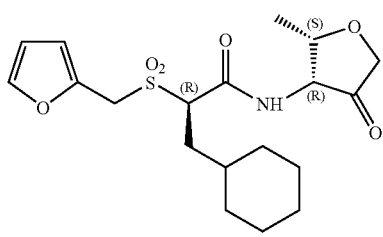

HPLC Rt=17.63 mins (>80%), HPLC-MS 398.1 [M+H]+, 817.1 [M+Na]+.
Prepared as detailed for EXAMPLE 5, but using loaded building block-linker construct (9c)

EXAMPLE 30

(2S, 3R) 3-Cyclohexyl-2-(furan-2-ylmethanesulfonyl)-N-(2-methyl-4-oxo-tetrahydrofuran-3-yl)-propionamide

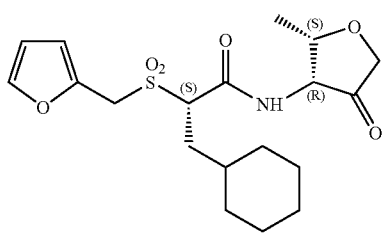

HPLC Rt=17.93 mins (>95%), HPLC-MS 398.1 [M+H]+, 817.1 [M+Na]+.
Prepared as detailed for EXAMPLE 6, but using loaded building block-linker construct (9c)

EXAMPLE 31

(2S, 3R) 2-(4-tert-Butyl-phenylmethanesulfonyl)-4-methyl-pentanoic acid (2-methyl-4-oxo-tetrahydrofuran-3-yl)-amide

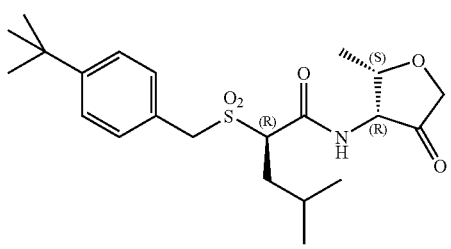

HPLC Rt=21.13 mins (>95%), HPLC-MS 424.2 [M+H]+, 869.4 [2M+Na]+.
Prepared as detailed for EXAMPLE 7, but using loaded building block-linker construct (9c)

EXAMPLE 32

(2S, 3R) Morpholine-4-carboxylic acid 2-cyclohexyl-1-(2-methyl-4-oxo-tetrahydro-furan-3-ylcarbamoyl)-ethyl ester

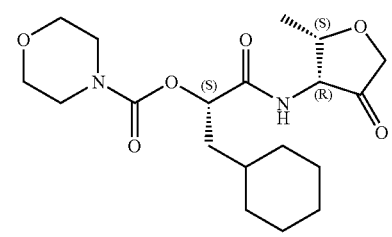

HPLC-MS 383.4 [M+H]+.
Prepared as detailed for EXAMPLE 8, but using loaded building block-linker construct (9c)

EXAMPLE 33

(2S, 3R) 2-Cyclohexylmethyl-N-(2-methyl-4-oxo-tetrahydrofuran-3-yl)-4-morpholin-4-yl-4-oxo-butyramide

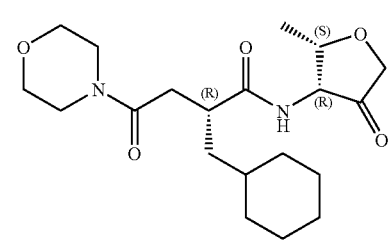

HPLC-MS 381.4 [M+H]+.
Prepared as detailed for EXAMPLE 9, but using loaded building block-linker construct (9c)

EXAMPLE 34

(2S, 3R) 2-Biphenyl-3-yl-4-methyl-pentanoic acid (2-methyl-1 oxo-tetrahydrofuran-3-yl)-amide

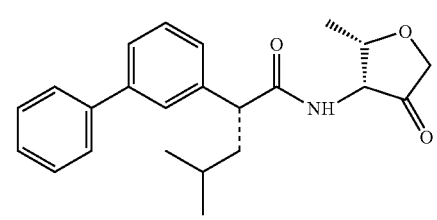

HPLC Rt=20.66 mins (>95%), HPLC-MS 366.1 [M+H]+, 753.2 [2M+Na]+.
Prepared as detailed for EXAMPLE 10, but using loaded building block-linker construct (9c)

EXAMPLE 35

(2R, 3R) 2-Benzyloxy-N-(2-methyl-4-oxo-tetrahydrofuran-3-yl)-3-phenyl-propionamide

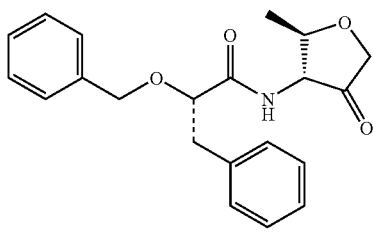

HPLC Rt=18.35 mins (>90%), HPLC-MS 354.2 [M+H]+, 376.1 [M+Na]+, 729.3 [2M+Na]+.

Following the general details from Scheme 1, the required bicycle building block (2R, 3R) (2-methyl-4-oxo-tetrahydrofuran-3-yl)-carbamic acid 9H-fluoren-9-ylmethyl ester (6d) was prepared as follows:

(1) Preparation of (1R, 1'R) [3-diazo-1-(1-hydroxyethyl)-2-oxopropyl]carbamic acid 9H-fluoren-9-ylmethyl ester.

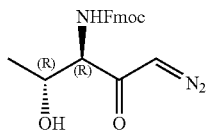

A solution of iso-butyl chloroformate (0.751 g, 5.5 mmol) in dichloromethane (10 ml) and a solution of 4-methylmorpholine (1.01 g, 10 mmol) in dichloromethane (10 ml) were simultaneously added in four portions to a stirred suspension of Fmoc-D-allo-threonine (1.71 g, 5 mmol) in dichloromethane (50 ml) at −15° C. over 10 minutes under an atmosphere of nitrogen. Ethereal diazomethane [generated from diazald (5.1 g, ~15 mmol) addition in diethyl ether (82 ml) to sodium hydroxide (5.73 g) in water (10 ml)/ethanol (20 ml) at 60° C.] was then cautiously added and the resulting yellow solution was stirred at room temperature for 90 minutes. Acetic acid (~2 ml) was cautiously added (until effervescence had ceased), then the mixture was diluted with tert-butyl methyl ether (50 ml). The ethereal layer was washed with water (3×50 ml), dried (Na$_2$SO$_4$) and the solvent removed in vacuo to leave (1R, 1'R) [3-diazo-1-(1-hydroxyethyl)-2-oxopropyl]carbamic acid 9H-fluoren-9-ylmethyl ester as a yellow solid (2.43 g) which was used without further purification.

(2) Cyclisation to (2R, 3R) (2-methyl-4-oxo-tetrahydrofuran-3-yl)carbamic acid 9H-fluoren-9-ylmethyl ester.

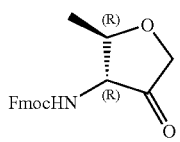

A solution of lithium chloride (2.12 g, 50 mmol) in 80% acetic acid in water (75 ml) was added to (1R, 1'R) [3-diazo-1-(1-hydroxyethyl)-2-oxopropyl]carbamic acid 9H-fluoren-9-ylmethyl ester (2.43 g, ~5 mmol). The yellow oily suspension was stirred for 2 hours whereupon a pale yellow solution formed accompanied by the evolution of a gas. The solvents were removed in vacuo then the residue was dissolved in ethyl acetate (30 ml), washed with 10% aqueous sodium carbonate solution (2×30 ml) and saturated aqueous sodium chloride solution (30 ml). The combined aqueous layers were extracted with ethyl acetate (2×30 ml) then the combined ethyl acetate layers were dried (Na$_2$SO$_4$) and the solvents removed in vacuo to leave a yellow gum (1.59 g). The yellow gum was purified by chromatography over silica gel eluting with a gradient of n-heptane:ethyl acetate 9:1→7:3. Appropriate fractions were combined and the solvents removed in vacuo to leave (2R, 3R) (2-methyl-4-oxo-tetrahydrofuran-3-yl)carbamic acid 9H-fluoren-9-ylmethyl ester as a white crystalline solid (796 mg, 47% from starting acid). TLC (single UV spot, Rf=0.27, n-heptane:ethyl acetate 2:1), analytical HPLC peak Rt=18.04 mins, HPLC-MS (single UV peak with Rt=8.47 mins, 338.1 [M+H]+, 360.0 [M+Na]+, 361.1 [M+H+Na]+).

δ$_H$ (CDCl$_3$ at 298K); 1.51–1.52 (3H, CH$_3$CHO, brs), 3.81–3.83 (1H, CH$_3$CHO m), 3.98–4.03 (2H, Fmoc CH$_2$, m), 4.14–4.17 (2H, Fmoc H-9 and NHCHCO, m), 4.29–4.53 (2H, OCH$_2$CO, dd), 5.18–5.19 (1H, NH, bs), 7.28–7.32 (2H, ArH, Fmoc H-2 and H-7), 7.34–7.36 (2H, ArH, Fmoc H-3 and H-6), 7.41–7.54 (2H, ArH, Fmoc H-1 and H-8), 7.59–7.80 (2H, ArH, Fmoc H-4 and H-5).

δ$_C$ (CDCl$_3$ at 298K); 18.27 (u, CH$_3$CHO), 46.35 (u, Fmoc C-9), 61.91 (u, NHCHCO), 66.46 (d, Fmoc CH$_2$), 70.03 (d, COCH$_2$), 76.60 (u, CH$_3$CHO), 119.26 (u, Fmoc C4 and C-5), 124.21 (u, Fmoc C-1 and C-8), 126.35 (u, Fmoc C-2 and C-7), 127.03 (u, Fmoc C-3 and C-6), 140.57 (q, Fmoc C4' and C-5'), 142.81/142.86 (q, Fmoc C-1' and C-8'), 155.27 (OCON), 211.05 (COCH$_2$).

Following the general details from Scheme 2, the required bicycle building (2R, 3R) (2-methyl-4-oxo-tetrahydrofuran-3-yl)-carbamic acid 9H-fluoren-9-ylmethyl ester (6d) was converted to building block-linker construct (8d) as follows:

(2R, 3R) (2-methyl-4-oxo-tetrahydrofuran-3-yl)-carbamic acid 9H-fluoren-9-ylmethyl ester (6d) (354 mg, 1.05 mmol, 1 eq) was dissolved in a mixture of ethanol (9.6 mL) and water (1.4 mL) containing sodium acetate.trihydrate (218 mg, 1.6 mmol, 1.5 eq). 4-[[(hydrazinocarbonyl)amino]methyl]cyclohexanecarboxylic acid. trifluoroacetate (346 mg, 1.05 mmol, 1 eq, Murphy, A. M. et al, *J. Am. Chem. Soc.*, 114, 3156–3157, 1992) was added and the mixture refluxed for 2 hr. Chloroform (100 mL) was added and the organics washed with dilute aqueous hydrochloric acid (0.1 M, 1×100 mL). The acidic layer was backwashed with chloroform (3×100 mL) and the combined organics washed with brine (100 mL), dried (Na$_2$SO$_4$) and evaporated under reduced pressure to afford linker construct (8d) as a white solid (620 mg). Analytical HPLC indicated one main peak at R$_t$=17.20 min, HPLC-MS (main UV peak with R$_t$=7.91 min, 535.3 [M+H]+. Crude (8d) was used directly for construct loading.

Following the general details from Scheme 2, the required building block-linker construct (8d) was attached to the solid phase providing loaded building block-linker construct (9d) as follows:

Building block-linker construct (8d) (1.0 mmole), 2-(1H-benzotriazole-1-yl)-1,1,3,3-tetramethyluroniumhexafluoro phosphate (HBTU, 379 mg, 1.0 mmole), 1-hydroxybenzotriazole.hydrate and (HOBT, 153 mg, 11.0 mmole) were dissolved in dimethylformamide (5 mL) and N-methylmorpholine (NMM, 220 µL, 2.0 mmole) added. After pre-activation for 5 minutes, free amine gears (250×1.21 mole)

were added, followed by dimethylformamide (30 mL) and left overnight. The spent coupling solution was then added to free amine crowns (25×10 μmole) and left overnight. Standard washing and analyses indicated loading at >95%.

Following the general details from Scheme 2, the required loaded building block-linker construct (9d) was elaborated on the solid phase as follows:

2RS-benzyloxy-3-phenylpropionic acid was coupled under standard conditions to loaded building block-linker construct (9d) (following standard removal of Fmoc), then cleaved to provide EXAMPLE 35. The crude example was analysed (see general techniques). HPLC Rt=18.35 mins (>90%), HPLC-MS 354.2 [M+H]$^+$, 376.1 [M+Na]$^+$, 729.3 [2M+Na]$^+$.

The following examples (36–47) were prepared as detailed for EXAMPLE 35, coupling with the required reagents to provide the fill length molecule.

EXAMPLE 36

(2R, 3R) 4-Methyl-2-(4-trifluoromethylbenzyloxy)-pentanoic acid (2-methyl-4-oxo-tetrahydrofuran-3-yl)-amide

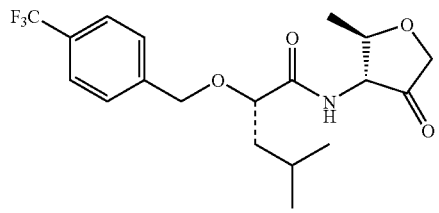

HPLC Rt=20.69 mins (>90%), HPLC-MS 388.2 [M+H]$^+$, 797.2 [2M+Na]$^+$.

Prepared as detailed for EXAMPLE 12, but using loaded building block-linker construct (9d)

EXAMPLE 37

(2R, 3R) 2-Benzyloxy-3-cyclohexyl-N-(2-methyl-4-oxo-tetrahydro furan-3-yl)-propionamide

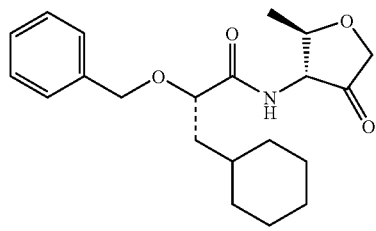

HPLC Rt=20.70 mins (>90%), HPLC-MS 360.2 [M+H]$^+$, 741.4 [2M+Na]$^+$.

Prepared as detailed for EXAMPLE 1, but using loaded building block-linker construct (9d)

EXAMPLE 38

(2R, 3R) 3-Cyclohexyl-2-(furan-2-ylmethylsulfanyl)-N-(2-methyl-4-oxo-tetrahydrofuran-3-yl)-propionamide

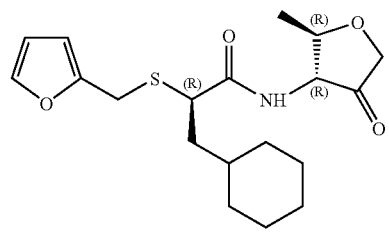

HPLC Rt=19.71 mins (>80%), HPLC-MS 366.1 [M+H]$^+$, 753.2 [M+Na]$^+$.

Prepared as detailed for EXAMPLE 3, but using loaded building block-linker construct (9d)

EXAMPLE 39

(2R, 3R) 3-Cyclohexyl-2-(furan-2-ylmethylsulfanyl)-N-(2-methyl-4-oxo-tetrahydrofuran-3-yl)-propionamide

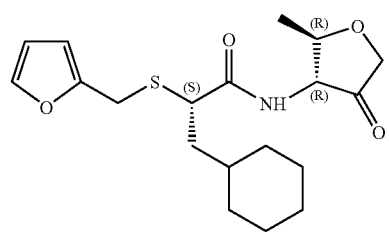

HPLC Rt=19.71 mins (>80%), HPLC-MS 366.1 [M+H]$^+$, 753.2 [M+Na]$^+$.

Prepared as detailed for EXAMPLE 4, but using loaded building block-linker construct (9d)

EXAMPLE 40

(2R, 3R) 2-(4-tert-Butyl-benzylsulfanyl)-4-methyl-pentanoic acid (2-methyl-4-oxo-tetrahydrofuran-3-yl)-amide

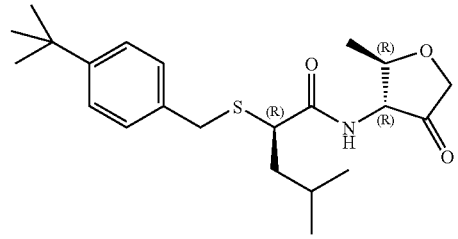

HPLC Rt=23.23 mins (>95%), HPLC-MS 392.2 [M+H]$^+$, 805.4 [2M+Na]$^+$.

Prepared as detailed for EXAMPLE 7, but using loaded building block-Linker construct (9d) and no oxidation of the intermediate thioether.

EXAMPLE 41

(2R, 3R) 3-Cyclohexyl-2-(furan-2-ylmethanesulfonyl)-N-(2-methyl-4-oxo-tetrahydrofuran-3-yl)-propionamide

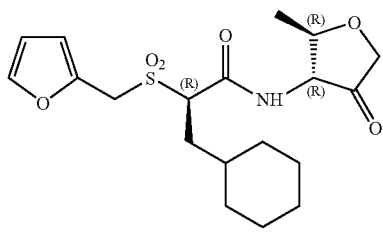

HPLC Rt=17.67 mins (>80%), HPLC-MS 398.1 [M+H]+, 817.1 [M+Na]+.

Prepared as detailed for EXAMPLE 5, but using loaded building block-linker construct (9d)

EXAMPLE 42

(2R, 3R) 3-Cyclohexyl-2-(furan-2-ylmethanesulfonyl)-N-(2-methyl-4-oxo-tetrahydrofuran-3-yl)-propionamide

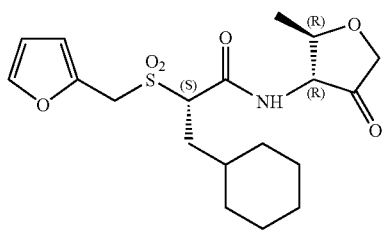

HPLC Rt=17.93 mins (>95%), HPLC-MS 398.1 [M+H]+, 817.1 [M+Na]+.

Prepared as detailed for EXAMPLE 6, but using loaded building block-linker construct (9d)

EXAMPLE 43

(2R, 3R) 2-(4-tert-Butyl-phenylmethanesulfonyl)-4-methyl-pentanoic acid (2-methyl-4-oxo-tetrahydrofuran-3-yl)-amide

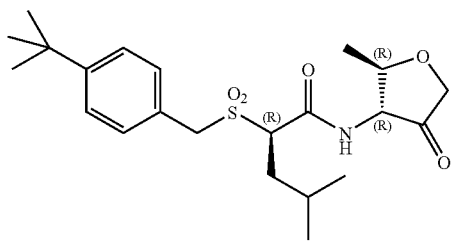

HPLC Rt=21.19 mins (>95%), HPLC-MS 424.2 [M+H]+, 869.4 [2M+Na]+.

Prepared as detailed for EXAMPLE 7, but using loaded building block-linker construct (9d)

EXAMPLE 44

(2R, 3R) Morpholine-4-carboxylic acid 2-cyclohexyl-1-(2-methyl-4-oxo-tetrahydro-furan-3-ylcarbamoyl)-ethyl ester

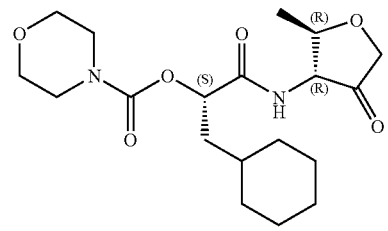

HPLC-MS 383.4 [M+H]+.

Prepared as detailed for EXAMPLE 8, but using loaded building block-linker construct (9d)

EXAMPLE 45

(2R, 3R) 2-Cyclohexylmethyl-N-(2-methyl-4-oxo-tetrahydrofuran-3-yl)-4-morpholin-4-yl-4-oxo-butyramide

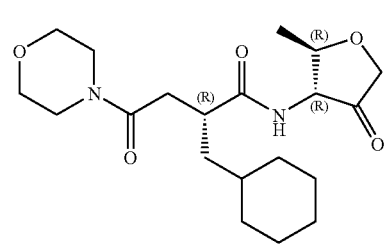

HPLC-MS 381.4 [M+H]+.

Prepared as detailed for EXAMPLE 9, but using loaded building block-linker construct (9d)

EXAMPLE 46

(2R, 3R) 2-Biphenyl-3-yl-4-methyl-pentanoic acid (2-methyl-4-oxo-tetrahydrofuran-3-yl)-amide

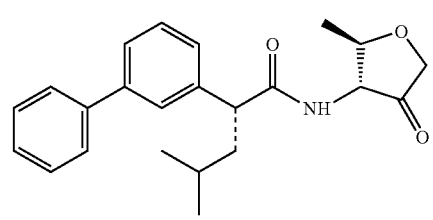

HPLC Rt=20.62 mins (>95%), HPLC-MS 366.1 [M+H]+, 753.2 [2M+Na]+.

Prepared as detailed for EXAMPLE 10, but using loaded building block-linker construct (9d)

EXAMPLE 47

(2R, 3S) 2-[2-(3,4-Dihydro-1H-isoquinolin-2-yl)-2oxo-ethyl]-4-methyl-pentanoic acid (2-methyl-4-oxo-tetrahydrofuran-3-yl)-amide

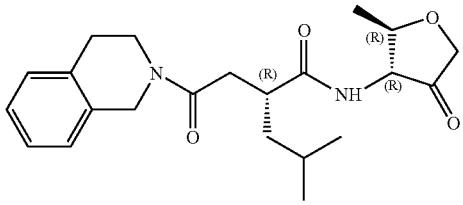

HPLC Rt=16.04 & 16.54 mins (>80%), HPLC-MS 387.2 [M+H]$^+$, 795.4 [2M+Na]$^+$.

Prepared as detailed for EXAMPLE 23, but using loaded building block-linker construct (9d)

Solution Phase Syntheses

EXAMPLES (48–51) were prepared by standard solution phase chemistries, coupling with the required reagents to provide the full length molecule. The core building block (4S, 5R) 4-amino-5-methyl-dihydro-furan-3-one hydrochloride (Compound (31), Schemes 9 and 10) was prepared as follows:

(1) Preparation of (1S, 1'R) [1-(1-tert-butoxyethyl)-3-diazo-2-oxopropyl]carbamic acid tert-butyl ester

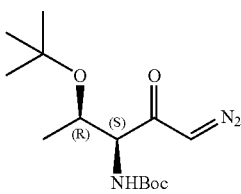

A solution of iso-butyl chloroformate (0.998 ml, 7.7 mmol) in dichloromethane (14 ml) and a solution of 4-methylmorpholine (1.54 ml, 14 mmol) in dichloromethane (14 ml) were simultaneously added to a stirred suspension of Boc-O-(tert-butyl)-L-threonine (1.93 g, 7 mmol) in dichloromethane (70 ml) at −15° C. over 10 minutes under an atmosphere of argon. Ethereal diazomethane [generated from diazald (7.14 g, ~21 mmol) addition in diethyl ether (115 ml) to sodium hydroxide (8.02 g) in water (11 ml)/ethanol (31 ml) at 60° C.] was then cautiously added and the resulting yellow solution was stirred at room temperature for 90 minutes. Acetic acid (~2 ml) was cautiously added (until effervescence had ceased) then the mixture was diluted with tert-butyl methyl ether (50 ml). The ethereal layer was washed with water (3×50 ml), dried (Na$_2$SO$_4$) and the solvent removed in vacuo to leave (1S, 1'R) [1-(1-tert-butoxyethyl)-3-diazo-2-oxopropyl]carbamic acid tert-butyl ester as a yellow solid (2.81 g) which was used without further purification.

(2) Cyclisation to (2R, 3S) (2-methyl-4-oxo-tetrahydrofuran-3-yl)carbamic acid tert-butyl ester

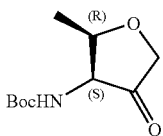

A solution of lithium chloride (2.97 g, 70 mmol) in 80% acetic acid in water (105 ml) was added to (1S, 1'R)[1-(1-tert-butoxyethyl)-3-diazo-2-oxopropyl]carbamic acid tert-butyl ester (2.81 g, ~7 mmol). The yellow oily suspension was stirred for 2 hours whereupon a pale yellow solution formed accompanied by the evolution of a gas. The solvents were removed in vacuo then the residue was dissolved in ethyl acetate (42 ml), washed with 10% aqueous sodium carbonate solution (2×42 ml) and saturated aqueous sodium chloride solution (42 ml). The combined aqueous layers were extracted with ethyl acetate (2×42 ml) then the combined ethyl acetate layers were dried (Na$_2$SO$_4$) and the solvents removed in vacuo to leave a yellow gum (1.1 g). The yellow gum was purified by chromatography over silica gel eluting with n-heptane:ethyl acetate 3:1 Appropriate fractions were combined and the solvents removed in vacuo to leave (2R, 3S) (2-methyl-4-oxo-tetrahydrofuran-3-yl)carbamic acid tert-butyl ester as a white crystalline solid (393 mg, 26% from starting acid). TLC (single UV spot, Rf=0.31, n-heptane:ethyl acetate 2:1), HPLC-MS (single UV peak with Rt=6.448 mins, 238.1 [M+Na]$^+$, 453.3 [2M+Na]$^+$).

$\delta_H$ (CDCl$_3$ at 298K); 1.47 (9H, G(CH$_3$)$_3$, s), 1.53 (3H, CH$_3$CHO, d, J=6.02 Hz), 3.68–3.81 (1H, CH$_3$CHO, m), 3.90–4.05 (2H, COCH$_2$O and NHCHCO, m), 4.20–4.31 (1H, OCH$_2$CO, d, J=17.36 Hz), 4.84–4.97 (1H, NH, brs).

$\delta_C$ (CDCl$_3$ at 298K); 19.50 (u, CH$_3$CHO), 28.61 (u, C(CH$_3$)$_3$), 62.91 (u, Cα), 71.23 (d, COCH$_2$), 78.06 (u, CH$_3$CHO), 81.03 (q, C(CH$_3$)$_3$), 155.73 (q, OCON), 212.85(q, COCH$_2$).

(3) Preparation of (4S, 5R) 4-amino-5-methyl-dihydrofuran-3-one Hydrochloride.

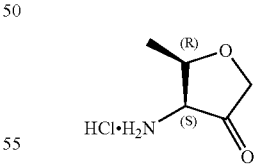

HCl in dioxane (4.0M, 9 ml) was added drop-wise with stirring over 1 minute to (2R, 3S) (2-methyl-4-oxo-tetrahydrofuran-3-yl)carbamic acid tert-butyl ester (0.372 g, 1.73 mmol). The mixture was stirred for 20 minutes then the solvents evaporated in vacuo to leave a residue which was azeotroped with toluene (2×20 ml) to leave (4S, 5R) 4amino-5-methyl-dihydro-furan-3-one hydrochloride as a white solid (266 mg, 100%). HPLC-MS, Rt=0.419 mins, 116.1 [M+H]$^+$).

EXAMPLE 48

(2R, 3S) 2-(4tert-Butylbenzyloxy)-4-methyl-pentanoic acid (2-methyl-4-oxo-tetrahydrofuran-3-yl)-amide

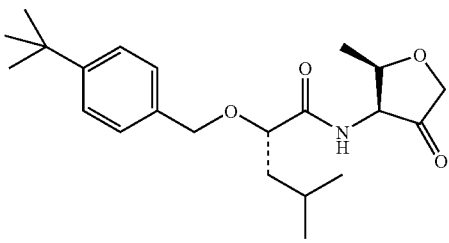

HPLC Rt=21.429 mins, HPLC-MS 376.2 [M+H]$^+$, 773.4 [2M+Na]$^+$.

The required ether carboxylic acid building block 2RS-(4-tert-butyl-benzyloxy)-4-methyl-pentanoic acid (compound (33), Scheme 10) was prepared from (S)-2-hydroxyisocaproic acid (32) as follows:

(1) Preparation of 2RS-(4-tert-butylbenzyloxy)-4-methylpentanoic acid (compound (33), Scheme 10)

A solution of (S)-2-hydroxyisocaproic acid (compound (32) 0.66 g, 5 mmol) in dichloromethane (10 ml) was added to a suspension of sodium hydride (0.44 g of 60% dispersion in oil, 11 mmol) in dimethylformamide (20 ml) at 0° C. The mixture was stirred at 0° C. for 0.5 hours then a solution of 4-tert-butylbenzyl bromide (1.42 g, 6.25 mmol) in dichloromethane (5 ml) was added drop-wise. The suspension was stirred for 2 hours then 1M hydrochloric acid (40 ml) was added and the product extracted into dichloromethane (100 ml) then washed with saturated aqueous sodium chloride solution (2×50 ml), dried (Na$_2$SO$_4$) and the solvent removed in vacuo to leave a residue. The residue was purified by chromatography over silica gel eluting with methanol:dichloromethane 1:100. Appropriate fractions were combined and the solvents removed in vacuo to leave 2RS-(4-tert-butylbenzyloxy)-4-methyl-pentanoic acid as a yellow oil (79 mg, 6%). Analytical HPLC peak Rt=21.310 mins, HPLC-MS (single peak with Rt=10.424 mins, 301.1 [M+Na]$^+$, 579.2 [2M+Na]$^+$).

$\delta_H$ (CDCl$_3$ at 298K); 0.71 and 0.88 (6H, CH$_2$CH(CH$_3$)$_2$, both d, J=6.6 Hz), 1.23 (9H, C(CH$_3$)$_3$, s), 1.42–1.54 (1HCH$_2$CH(CH$_3$)$_2$, m), 1.63–1.74 (1HCH$_2$CH(CH$_3$)$_2$, m), 1.75–1.87 (1H, CH$_2$CH(CH$_3$)$_2$, m), 3.88–3.97 (1H, OCHCOOH, m), 4.28–4.35 (1H, ArCH$_2$O, d, J=11.26 Hz), 4.55–4.67 (1H, ArCH$_2$O, d, J=11.25 Hz), 7.20–7.33 (4H, ArH, m).

$\delta_C$ (CDCl$_3$ at 298K); 23.61 (u, CH$_2$CH(CH$_3$)$_2$), 24.83 (u, CH$_2$CH(CH$_3$)$_2$), 31.51 (u, C(CH$_3$)$_3$), 42.14 (d, CH$_2$CH(CH$_3$)$_2$), 72.68 (d, ArCH$_2$O), 76.54 (u, OCHCOOH), 125.75/125.84 (u, aromatic CH), 128.29/128.48 (u, aromatic CH), 134.71 (q, Ar C), 151.36 (q, Ar C), 178.41 (q, CO).

Carboxylic acid building (33) and (4S, 5R) 4-amino-5-methyl-dihydro-furan-3-one hydrochloride (31) were coupled as follows:

iso-Butyl chloroformate (20.09 mg, 0.1471 mmol) in dichloromethane (2 ml) and N-methyl morpholine (29.75 mg, 0.294 mmol) in dichloromethane (2 ml) were simultaneously added were simultaneously added to a stirred solution of (31) (37.22 mg, 0.1337 mmol) in dichloromethane (2 ml) at −15° C. under argon over 5 minutes. The mixture was stirred at −15° C. for 15 minutes. A freshly prepared solution of (33) (20.27 mg, 0.1337 mmol) in dichloromethane (2 ml) and 4-methylmorpholine (13.52 mg, 0.1337 mmol) was then added dropwise. The mixture was then stirred at ambient temperature for 16 hours. The solvent was removed in vacuo to give a residue which was purified over silica gel eluting with a gradient of n-heptane:ethyl acetate 3:1 to 2:1. Desired fractions were combined and reduced in vacuo to leave a white foam (37.10 mg, 73.9% from starting acid). TLC (single UW spot, Rf=0.85, 10% MeOH in DCM), analytical HPLC single peak with Rt=21.429 mins, HPLC-MS (single UV peak with Rt=10.829 mins, 376.2 [M+H]$^+$, 773.4 [2M+Na]$^+$.

$\delta_H$ (CDCl$_3$ at 298K); 0.75–0.90 (6H, (CH$_3$)$_2$CH$_2$, m), 1.25 (9H, C(CH$_3$)$_3$, s), 1.34–1.41 (3H, OCHCH$_3$, d, J=6.03 Hz), 1.45–1.63 (2H, CH$_2$CH(CH$_3$)$_2$, m), 1.71–1.87 (1H, CH$_2$CH(CH$_3$)$_2$, m), 3.71–3.80 (1H, OCHCH$_3$, m), 3.83–4.04 (3H, OCHCO, NHCHCO and COCH$_2$O, m), 4.12–4.21 (1H, COCH$_2$O, m), 4.47 (2H, ArCH$_2$, s), 6.77 (1H, NH, s), 7.18–7.36 (4H, ArH, m).

EXAMPLE 49

(2R, 3S)N-(2-Methyl-4-oxo-tetrahydrofuran-3-yl)-2-(naphthalen-1-ylmethoxy)-3-phenyl-propionamide

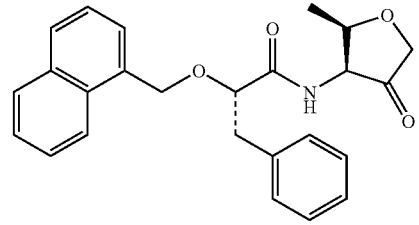

Analytical HPLC Rt=20.50 mins (major isomer) and 20.64 mins (minor isomer) and HPLC-MS (single major UV peak with Rt=9.746 mins, 404.2 [M+H]$^+$, 426.2 [M+Na]$^+$, 829.4 [2M+Na]$^+$).

The required ether carboxylic acid building block 2RS-(Naphthalen-1-ylmethoxy)-3-phenylpropionic acid was prepared as follows:

Sodium hydride (265 mg of 60% dispersion in oil, 6.6 mmol) was added in two portions to a stirred mixture of (S)-2-hydroxy-3-phenylpropionic acid (0.5 g, 3.0 mmol), dimethylformamide (5 ml) and dichloromethane (5 ml) at 0° C. over 5 minutes. The mixture was stirred at 0° C. for 5 minutes then at ambient temperature for 30 minutes. 1-(Chloromethyl)naphthalene (95%, 0.57 ml, 3.6 mmol) was added then the mixture stirred for 5 hours before adding potassium iodide (50 mg, 0.3 mmol). The mixture was stirred for 20 hours then heated at 55° C. for 1 hour then allowed to cool to ambient temperature and poured into water (15 ml). A saturated aqueous sodium chloride solution (5 ml) was added then the mixture was extracted with dichloromethane (5 ml then 10 ml) that was discarded. The aqueous layer was acidified using 1M hydrochloric acid (10 ml) then extracted with dichloromethane (2×10 ml). The dichloromethane layer was dried (MgSO$_4$) and the solvent removed in vacuo. The residue (0.48 g) was dissolved in dimethylformamide (6 ml) then cooled to 0° C. before adding sodium hydride (150 mg of 60% dispersion in oil, 3.75 mmol). The mixture was stirred for 30 minutes then polymer bound isocyanate (300 mg, 2 mmol Ng$^{-1}$) added. The mixture was stirred for 2 hours at ambient temperature then poured into water (15 ml). 1M Hydrochloric acid (10 ml) was added then the product extracted into dichloromethane (2×10 ml), dried (MgSO$_4$) and the solvent removed in vacuo. The residue was dissolved in aqueous sodium hydroxide solution (1M, 10 ml) then extracted with dichloromethane (2×10 ml) that was discarded. Crushed ice was added to the aqueous layer followed by 1M hydrochloric acid (12 ml). The product was extracted into dichloromethane (2×10 ml) then dried (Na$_2$SO$_4$) and the solvent removed in vacuo. The residue was purified by flash chromatography over silica gel eluting with a gradient of methanol:dichloromethane 0:1→1:20. Appropriate fractions were combined and the solvents removed in vacuo to leave 2RS-(Naphthalen-1-ylmethoxy)-3-phenylpropionic acid (40 mg) as a colourless oil. HPLC-MS (single main UV peak with Rt=9.22 mins, 307.2 [M+H]$^+$, 329.2 [M+Na]$^+$).

$\delta_H$ (CDCl$_3$ at 298K); 2.82–3.18 (2H, PhC$\underline{H}_2$, m), 4.00–4.25 (1H, OC$\underline{H}$CO, m), 4.63–4.81 (1H, C$\underline{H}_2$O, d, J=11.55 Hz), 4.92–5.10 (1H C$\underline{H}_2$O, d, J=11.52 Hz), 6.90–7.86 (12H, ArH, m), 8.78 (1H, O$\underline{H}$, brs).

2RS-(Naphthalen-1-ylmethoxy)-3-phenylpropionic acid and (4S, 5R) 4-amino-5-methyl-dihydro-furan-3-one hydrochloride (31) were coupled as follows:

Solutions of isobutyl chloroformate (18.6 μl, 0.14 mmol) in dichloromethane (0.67 ml) and 4-methylmorpholine (31.6 μl, 0.29 mmol) in dichloromethane (0.67 ml) were added simultaneously at −15° C. over 10 minutes drop-wise to a stirred solution of 2RS-Naphthalen-1-ylmethoxy)-3-phenylpropionic acid (40 mg, 0.13 mmol) in dichloromethane (0.5 ml) under argon. The solution was stirred for 15 minutes then (4S, 5R) 4-amino-5-methyldihydrofuran-3-one hydrochloride (20 mg, 0.13 mmol) followed by a solution of 4-methylmorpholine (14.4 μl, 0.13 mmol) in dichloromethane (0.3 ml) were added. The mixture was allowed to warm to 0° C. over 3 hours, stirred at ambient temperature for 20 hours then the solvents were removed in vacuo. The residue was purified by flash chromatography over silica gel eluting with a gradient of ethyl acetate:heptane 1:3→7:13. Appropriate fractions were combined and the solvents removed in vacuo to leave (2R, 3S)N-(2-Methyl-4-oxo-tetrahydrofuran-3-yl)-2-(naphthalen-1-ylmethoxy)-3-phenyl-propionamide as a white solid (28.5 mg, 3.5:1 mixture of diastereoisomers, 70%). TLC (two spots, Rf=0.45 and 0.42, ethyl acetate:heptane 7:13).

$\delta_H$ (CDCl$_3$ at 298K); Major isomer 1.4 (3H, C$\underline{H}_3$CH, d, J=6.0 Hz), 2.90 (1H, PhC$\underline{H}_2$, dd, J=14.1, 8.0 Hz), 3.15 (1H, PhC$\underline{H}_2$, dd, J=14.1, 3.6 Hz), 3.32 and 3.51 (both 1H, CH$_3$C$\underline{H}$CHN, m), 3.85 (1H, OC$\underline{H}_2$CO, d, J=17.1 Hz), 4.08 (1H, OC$\underline{H}_2$CO, d, J=17.1 Hz), 4.19 (1H, OC$\underline{H}$CO, m), 4.6 (1H, OC$\underline{H}_2$Naphthyl, d, J=11.8 Hz), 4.90 (1H, OC$\underline{H}_2$Naphthyl, d, J=11.8 Hz), 6.55 (1H, N$\underline{H}$, d, J=6 Hz), 7.18–7.93 (12H, aromatic); Minor isomer 1.50 (3H, C$\underline{H}_3$CH, d, J=6.0 Hz), 2.94 (1H, PhC$\underline{H}_2$, m), 3.15 (1H, PhC$\underline{H}_2$, m), 3.52 and 3.89 (both 1H, CH$_3$C$\underline{H}$CHN, m), 4.02–4.22 (3H, OC$\underline{H}_2$CO and OC$\underline{H}$CO, m), 4.6 (2H, OC$\underline{H}_2$Naphthyl, s), 6.74 (1H, N$\underline{H}$, d, J=6 Hz), 7.18–7.93 (12H, aromatic).

EXAMPLE 50

(2R, 3S) 2-(Biphenyl-4-ylmethoxy)-4-methyl-pentanoic Acid (2-methyl-4-oxo-tetrahydrofuran-3-yl)-amide

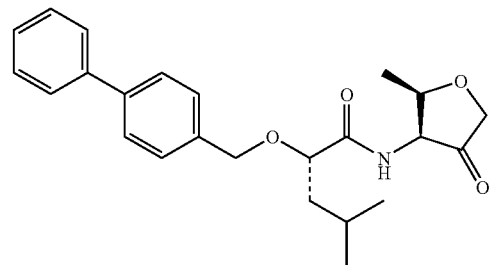

HPLC Rt=20.178 mins (>95%), HPLC-MS 396.2 [M+H]$^+$, 813.4 [2M+Na]$^+$.

The required ether carboxylic acid building block 2RS 2-(Biphenyl-4-ylmethoxy)-4-methyl-pentanoic acid was prepared as follows:

(1) Preparation of 2RS-(Biphenyl-4-ylmethoxy)4-methyl-pentanoic acid methyl ester Sodium hydride (98.4 mg of 60% dispersion in oil, 2.46 mmol) was added in two portions to a stirred solution of 2S-hydroxy-4-methyl-pentanoic acid methyl ester (300 mg, 2.05 mmol) in tetrahydrofuran (2.5 ml) at 0° C. under an atmosphere of nitrogen over 5 minutes. The mixture was stirred at ambient temperature for 10 minutes then a solution of 4-phenylbenzylchloride (830 mg, 4.1 mmol) followed by potassium iodide (25 mg) was added. The mixture was stirred for 20 hours then saturated aqueous ammonium chloride solution (40 ml) was added. The product was extracted into ethyl acetate (3×30 ml) then the combined ethyl acetate layers were washed with aqueous saturated sodium chloride solution, dried (Na$_2$SO$_4$) and the solvents removed in vacuo. The residue (1.2 g) was purified by flash chromatography over silica gel eluting with ethyl acetate: heptane 1:20→1:9. Appropriate fractions were combined and the solvents removed in vacuo to leave 3-cyclohexyl-2-(furan-3-ylmethoxy)-propionic acid methyl ester (110 mg, 17.1%) as a colourless oil. TLC (single spot, Rf=0.2, heptane:ethyl acetate 9:1), HPLC-MS main UV peak with 313.1 [M+H]$^+$.

(2) Preparation of 2RS-(Biphenyl-4-ylmethoxy)-4-methyl-pentanoic acid.

A solution of lithium hydroxide monohydrate (0.0443 g, 1.056 mmol) in water (3 ml) was added drop-wise over 1 minute to a solution of 2-(biphenyl-4-ylmethoxy)-4-methyl-pentanoic acid methyl ester (0.11 g, 0.3521 mmol) in tetrahydrofuran:methanol 2:1 (15 ml) at 0° C. The mixture was stirred at ambient temperature for 16 hours then poured into saturated aqueous sodium chloride solution (10 ml). The aqueous layer was extracted with diethyl ether (2×10 ml) which was discarded. The aqueous layer was acidified with 1M hydrochloric acid to pH (1~2), then the product was extracted into dichloromethane (3×10 ml). The combined dichloromethane layers were washed with water (2×10 ml), saturated aqueous sodium chloride solution (2×10 ml) then dried (Na$_2$SO$_4$) and the solvents removed in vacuo to leave 2-(biphenyl-4-ylmethoxy)-4-methyl-pentanoic acid as a colourless oil (0.048 g, 45.69%). TLC (single UV spot, Rf=0.2, methanol:dichloromethane 0.5:9.5), HPLC-MS (297.1 [M−1]$^+$, 321.1 [M+Na]$^+$, 619.3 [2M+Na]$^+$).

δ$_H$ (CDCl$_3$ at 298K); 0.71–0.94 (6H, (CH$_3$)$_2$CH, two d, J1a=6.57, J1b=6.66 Hz, J2=29.87 Hz), 1.19 (1H, OH, bs,), 1.45–1.76 (2H, CH$_2$CH(CH$_3$)$_2$, m), 1.77–1.92 (1H, CH$_2$CH(CH$_3$)$_2$, m), 2.93–4.05 (1H, CHCOOH, m), 4.37–4.48 (1H, CH$_2$Ar, d, J=11.43 Hz), 4.64–4.75 (1H, CH$_2$Ar, d, J=11.42 Hz), 7.23–7.60 (9H, ArH, m).

δ$_C$ (CDCl$_3$ at 298K); 23.17 (u, (CH$_3$)$_2$CH), 24.81/26.13 (u, (CH$_3$)$_2$CH), 43.30 (d, CH$_3$)$_2$CHCH$_2$), 74.06 (d, ArCH$_2$), 78.02 (u, OCHCOOH), 128.77/128.91/129.03.43 (u, Ar), 130.31/130.44 (u, Ar), 137.71 (q, Ar), 142.42/142.71 (q, Ar), 179.79 (q, OCO).

2RS-2-(Biphenyl-4-ylmethoxy)-4-methyl-pentanoic acid and (4S, 5R) 4-amino-5-methyl-dihydro-furan-3-one hydrochloride (31) were coupled as follows:

iso-Butyl chloroformate (15.61 mg, 0.1143 mmol) in dichloromethane (2 ml) and N-methyl morpholine (23.12 mg, 0.2286 mmol) in dichloromethane (2 ml) were simultaneously added were simultaneously added to a stirred solution of 2RS-2-(biphenylylmethoxy)-4-methyl-pentanoic acid (31 mg, 0.104 mmol) in dichloromethane (2 ml) at −15° C. under argon over 5 minutes. The mixture was stirred at −15° C. for 15 minutes. A freshly prepared solution of (31) (15.75 mg, 0.104 mmol) in dichloromethane (2 ml) and 4-methylmorpholine (11.56 mg, 0.1143 mmol) was then added dropwise. The mixture was then stirred at ambient temperature for 16 hours. The solvent was removed in vacuo to give a residue which was purified over silica gel eluting with a gradient of n-heptane: ethyl acetate 3:1. Desired fractions were combined and reduced in vacuo to leave (2R, 3S) 2-(Biphenyl-4-ylmethoxy)-4-methyl-pentanoic acid (2-methyl-4-oxo-tetrahydrofuran-3-yl)-amide as an off-white gum (34 mg, 82.7% from starting acid). TLC (single UV spot, Rf=0.85, 10% MeOH in DCM).

δ$_H$ (CDCl$_3$ at 298K); 0.72–0.93 (6H, (CH$_3$)$_2$CH$_2$, m), 1.39 (3H, OCHCH$_3$, d, J=6.04 Hz), 1.45–1.69 (2H, CH$_2$CH(CH$_3$)$_2$, m), 1.73–1.89 (1H, CH$_2$CH(CH$_3$)$_2$, m), 3.70–3.81 (1H, OCHCH$_3$, m), 3.84–4.08 (3H, OCHCONH, COCH$_2$O and NHCHCOCH$_2$, m), 4.10–4.20 (1H, COCH$_2$O, d, J=17.35 Hz), 4.40–4.67 (2H, ArCH$_2$O, m), 6.71 (1H, NH, bs), 7.60–7.24 (9H, ArH, m).

δ$_C$ (CDCl$_3$ at 298K); 17.19/17.27 (u, CH$_3$, furanone), 19.70/19.89/19.94 (u, CH$_2$CH(CH$_3$)$_2$), 21.38/21.43/22.74/22.79 (u, CH$_2$CH(CH$_3$)$_2$), 40.42/40.59/40.80 (d, OCHCH$_2$CH(CH$_3$)$_2$), 59.29 (u, NHCHCOCH$_2$), 69.17/69.24 (d, ArCH$_2$O), 70.93/71.05/71.28 (d, COCH$_2$), 74.68 (u, Cβ), 77.11/77.22 (u, OCHCONH), 125.22/125.51/125.57/125.60/125.63/126.68/126.97/127.18 (u, Ar CH), 133.81/133.98/134.11 (q, Ar C), 138.69/138.75/139.40/139.43 (q, Ar C, 171.99/172.23 (q, CON), 209.36/209.98/210.21/172.23 (q, COCH$_2$).

EXAMPLE 51

(2R, 3S) 3-Cyclohexyl-2-(furan-3-ylmethoxy)-N-(2-methyl-4-oxo-tetrahydro-furan-3-yl)-propionamide

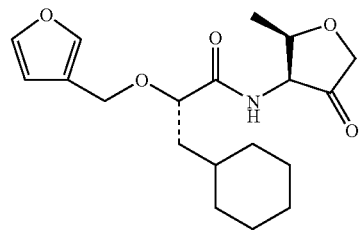

HPLC Rt=17.858 mins (>90%), HPLC-MS 350.2 [M+H]$^+$, 372.2 [M+Na]$^+$, 721.3 [2M+Na]$^+$.

The required ether carboxylic acid building block 2RS 3-Cyclohexyl-2-(furan-3-ylmethoxy)-propionic acid was prepared as follows:

(1) Preparation of 3-cyclohexyl-2-(furan-3-ylmethoxy)-propionic acid methyl ester.

Sodium hydride (204 mg of 60% dispersion in oil, 5.1 mmol) was added in two portions to a stirred solution of 3-cyclohexyl-2S-hydroxypropionic acid methyl ester (18) (794 mg, 4.27 mmol) in tetrahydrofuran (5 ml) at 0° C. under an atmosphere of nitrogen over 5 minutes. The mixture was stirred at ambient temperature for 10 minutes then a solution of 3-bromomethylfuran (2.75 g, 17.08 mmol) in tetrahydrofuran (1 ml) was added. The mixture was stirred for 20 hours then saturated aqueous ammonium chloride solution (40 ml) was added. The product was extracted into ethyl acetate (3×30 ml) then the combined ethyl acetate layers were washed with aqueous saturated sodium chloride solution, dried (Na$_2$SO$_4$) and the solvents removed in vacuo. The residue (2.0 g) was purified by flash chromatography over silica gel eluting with ethyl acetate:heptane 1:4. Appropriate fractions were combined and the solvents removed in vacuo to leave 3-cyclohexyl-2-(furan-3-ylmethoxy)-propionic acid methyl ester (64 mg, 6%) as a colourless oil. TLC (single spot, Rf=0.2, heptane: ethyl acetate 9:1), HPLC-MS (main UV peak [1]with Rt=10.701 mins, 289.1 [M+Na]$^+$, 555.3 [2M+Na]$^+$).

(2) Preparation of 3-cyclohexyl-2-(furan-3-ylmethoxy)-propionic acid.

A solution of lithium hydroxide monohydrate (0.03025 g, 0.721 mmol) in water (3 ml) was added drop-wise over 1 minute to a solution of 3-cyclohexyl-2-(furan-3-ylmethoxy)-propionic acid methyl ester (0.064 g, 0.240 mmol) in tetrahydrofuran: methanol 2:1 (15 ml) at 0° C. The mixture was stirred at ambient temperature for 16 hours then poured into saturated aqueous sodium chloride solution (10 ml). The aqueous layer was extracted with diethyl ether (2×10 ml) which was discarded. The aqueous layer was acidified with 1M hydrochloric acid to pH (1~2), then the product was extracted into dichloromethane (3×10 ml). The combined dichloromethane layers were washed with water (2×10 ml), saturated aqueous sodium chloride solution (2×10 ml) then dried (Na$_2$SO$_4$) and the solvents removed in vacuo to leave Preparation of 3-cyclohexyl-2-(furan-3-ylmethoxy)-propionic acid as a light yellow oil (0.012 g, 19.80%). TLC (single UV spot, Rf=0.35, methanol:dichloromethane 1:9), HPLC-MS (252.1 [M]$^+$, 275.2 [M+Na]$^+$, 527.2 [2M+Na]$^+$).

2RS 3-Cyclohexyl-2-(furan-3-ylmethoxy)-propionic acid and (4S, 5R) 4-amino-5-methyl-dihydro-furan-3-one hydrochloride (31) were coupled as follows:

iso-Butyl chloroformate (7.15 mg, 0.0523 mmol) in dichloromethane (2 ml) and N-methyl morpholine (10.58 mg, 0.1046 mmol) in dichloromethane (2 ml) were simultaneously added to a stirred solution of 2RS 3-Cyclohexyl-2-(furan-3-ylmethoxy)-propionic acid (12.00 mg, 0.048 mmol) in dichloromethane (2 ml) at −15° C. under argon over 5 minutes. The mixture was stirred at −15° C. for 15 minutes. A freshly prepared solution of (31) (7.21 mg, 0.048 mmol) in dichloromethane (2 ml) and 4-methylmorpholine (5.29 mg, 0.0523 mmol) was then added dropwise. The mixture was then stirred at ambient temperature for 16 hours. The solvent was removed in vacuo to give a residue which was purified over silica gel eluting with a gradient of n-heptane:ethyl acetate 3:1. Desired fractions were combined and reduced in vacuo to leave (2R, 3S) 3-Cyclohexyl-2-(furan-3-ylmethoxy)-N-(2-methyl-4-oxo-tetrahydro-furan-3-yl)-propionamide as an off-white gum (6 mg, 35.77% from starting acid). TLC (single spot, Rf=0.8, methanol:dichloromethane 1:9), analytical $\delta_H$ (CDCl$_3$ at 298K); 0.70–0.95 (2H, CH$_2$ (cyclohexyl), m), 1.02–1.25 (2H, CH$_2$ (cyclohexyl), m), 1.38 (3H, OCHC$\underline{H}_3$, d, J=6.12 Hz), 1.45–1.70 (8H, CH, CH$_2$ (cyclohexyl), m), 3.70–3.79 (1H, OC$\underline{H}$CH$_3$, m), 3.80–4.08 (3H, OC$\underline{H}$CONH, COC$\underline{H}_2$O and NHC$\underline{H}$COCH$_2$, m), 4.144.23 (1H, COC$\underline{H}_2$O, d, J=17.20 Hz), 4.30–4.46 (2H, 3-Furan-C$\underline{H}_2$O, m), 6.35 (1H, 2-Furan-CH, s), 6.76 (1H, NH, bs), 7.37 (2H, 4 and 5-Furan-CH, d, J=1.67 Hz).

EXAMPLE A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

General Materials and Methods

Unless otherwise stated, all general chemicals and biochemicals were purchased from either the Sigma Chemical Company, Poole, Dorset, U.K. or from Fisher Scientific UK, Loughborough, Leicestershire, U.K. Absorbance assays were carried out in flat-bottomed 96-well plates (Spectra; Greiner Bio-One Ltd., Stonehouse, Gloucestershire, U.K.) using a SpectraMax PLUS384 plate reader (Molecular Devices, Crawley, U.K.). Fluorescence high throughput assays were carried out in either 384-well microtitre plates (Corning Costar 3705 plates, Fisher Scientific) or 96-well 'U' bottomed Microfluor W1 microtitre plates (Thermo Labsystems, Ashford, Middlesex, U.K.). Fluorescence assays were monitored using a SpectraMax Gemini fluorescence plate reader (Molecular Devices). For substrates employing either a 7-amino-4-methylcoumarin (AMC) or a 7-amino-4-trifluoromethylcoumarin (AFC) fluorophore, assays were monitored at an excitation wavelength of 365 nm and an emission wavelength of 450 nm and the fluorescence plate reader calibrated with AMC. For substrates employing a 3-amino-benzoyl (Abz) fluorophore, assays were monitored at an excitation wavelength of 310 nm and an emission wavelength of 445 nm; the fluorescence plate reader calibrated with 3-amino-benzamide (Fluka). Unless otherwise indicated, all the peptidase substrates were purchased from Bachem UK, St. Helens, Merseyside, UK. Substrates utilizing fluorescence resonance energy transfer methodology (i.e. FRET-based substrates) were synthesized at Incenta Limited using published methods (Atherton & Sheppard, *Solid Phase Peptide Synthesis*, IRL Press, Oxford, U.K., 1989) and employed Abz (2-aminobenzoyl) as the fluorescence donor and 3-nitro-tyrosine [Tyr(NO$_2$)] as the fluorescence quencher (Meldal, M. and Breddam, K., *Anal. Biochem.*, 195, 141–147, 1991). Hydroxyethylpiperazine ethanesulfonate (HEPES), tris-hydroxylmethyl aminomethane (tris) base, bis-tris-propane and all the biological detergents (e.g. CHAPS, zwittergents, etc.) were purchased from CN Biosciences UK, Beeston, Nottinghamshire, U.K. Glycerol was purchased from Amersham Pharmacia Biotech, Little Chalfont, Buclinghamshire, U.K. Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.).

Assay protocols were based on literature precedent (Table 1; Barrett, A. J., Rawlings, N. D. and Woessner, J. F., 1998, *Handbook of Proteolytic Enzymes*, Academic Press, London and references therein) and modified as required to suit local assay protocols. Enzyme was added as required to initiate the reaction and the activity, as judged by the change in fluorescence upon conversion of substrate to product, was monitored over time. All assays were carried out at 25±1° C.

TABLE 1

The enzyme assays described herein were carried out according to literature precedents.

| Enzyme | Buffer | Substrate | Reference |
|---|---|---|---|
| Cathepsin B | I | Z-Phe-Arg-AMC | a, b |
| Cathepsin H | II | Bz-Phe-Val-Arg-AMC | a, b |
| Cathepsin L | I | Ac-Phe-Arg-AMC | b, c |
| Cathepsin S | I | Boc-Val-Leu-Lys-AMC | c, d |
| Caspase 1 | III | Ac-Leu-Glu-His-Asp-AMC | e |
| Caspase 2 | III | Z-Val-Asp-Val-Ala-Asp-AFC | f |
| Caspase 3 | III | Ac-Asp-Glu-Val-Asp-AMC | g, h |
| Caspase 4 | III | Suc-Tyr-Val-Ala-Asp-AMC | f |
| Caspase 5 | III | Ac-Leu-Glu-His-Asp-AMC | |
| Caspase 6 | III | Ac-Val-Glu-Ile-Asp-AMC | i, j, k |
| Caspase 7 | III | Ac-Asp-Glu-Val-Asp-AMC | |
| Caspase 8 | III | Ac-Ile-Glu-Thr-Asp-AMC | l |
| Caspase 9 | III | Ac-Leu-Glu-His-Asp-AMC | |
| Caspase 10 | III | Ac-Ile-Glu-Thr-Asp-AMC | |
| Cruzipain | IV | D-Val-Leu-Lys-AMC | m, n |
| CPB2.8ΔCTE | XI | Pro-Phe-Arg-AMC | q |
| *S. Aureus* Extracellular cysteine peptidase | I | Abz-Ile-Ala-Ala-Pro-Tyr(NO$_2$)-Glu-NH$_2$ | o |
| Clostripain | | Z-Gly-Gly-Arg-AMC | p |
| FMDV LP | V | Abz-Arg-Lys-Leu-Lys-Gly-Ala-Gly-Ser-Tyr(NO$_2$)-Glu-NH$_2$ | r |
| Trypsin | VI | Z-Gly-Gly-Arg-AMC | s |
| Calpain μ | VII | Abz-Ala-Asn-Leu-Gly-Arg-Pro-Ala-Leu-Tyr(NO$_2$)-Asp-NH$_2$ | t |
| Calpain m | VIII | Abz-Lys-Leu-Cys(Bzl)-Phe-Ser-Lys-Gln-Tyr(NO$_2$)-Asp-NH$_2$ | t |
| Cathepsin K | IX | Z-Phe-Arg-AMC | u |
| Cathepsin X | X | | v, w |

I: 10 mM BTP, pH 6.5 containing 1 mM EDTA, 5 mM 2-mercaptoethanol and 1 mM CaCl$_2$
II: 10 mM BTP, pH 6.5 containing 1 mM EDTA, 142 mM NaCl, 1 mM DTT, 1 mM CaCl$_2$, 0.035 mM Zwittergent 3–16

TABLE 1-continued

The enzyme assays described herein were carried out according to literature precedents.

Enzyme  Buffer Substrate  Reference

III: 50 mM HEPES pH 7.2, 10% Glycerol, 0.1% CHAPS, 142 mM NaCl, 1 mM EDTA, 5 mM DTT
IV: 100 mM sodium phosphate, pH 6.75 containing 1 mM EDTA and 10 mM L-cysteine
V: 50 mM triacetate, pH 8.4 containing 1 mM EDTA, 10 mM L-cysteine and 0.25% (w/v) CHAPS
VI: 10 mM HEPES, pH 8.0 containing 5 mM $CaCl_2$
VII: 10 mM HEPES, pH 7.5 containing 2 mM 2-mercaptoethanol and 100 µM $CaCl_2$
VIII: 10 mM HEPES, pH 7.5 containing 2 mM 2-mercaptoethanol and 200 µM $CaCl_2$
IX: 100 mM sodium acetate; pH 5.5 containing 10 mM L-cysteine and 1 mM EDTA
X: 100 mM sodium acetate; pH 5.5 containing 10 mM L-cysteine; 0.05% (w/v) Brij 35 and 1 mM EDTA
XI: 100 mM sodium acetate; pH 5.5 containing 10 mM L-cysteine; 142 mM sodium chloride and 1 mM EDTA
a Barrett, A. J., Biochem. J., 187, 909–912, 1980
b Barrett, A. J. and Kirschke, H., Methods Enzymol., 80, 535–561, 1981
c Quibell, M. and Taylor, S., WO0069855, 2000
d Bromme, D., Steinert, ., Freibe, S., Fittkau, S., Wiederanders, B., and Kirschke, H., Biochem. J., 264, 475–481, 1989
e Rano, T. A., et. al., Chem. Biol., 4, 149, 1997
f Talanian, R. V., et. al., J. Biol. Chem., 272, 9677, 1997
g Lazebnik, Y. A., Kaufmann, S. H., Desnoyers, S., Poirer, G. G. and Earnshaw, W. C., Nature, 371, 768–774, 1994
h Han, Z., et. al., J. Biol. Chem., 272, 13432, 1997
i Takahashi, A., et. al., PNAS, 93, 8395, 1996
j Martins, L. M., et. al., J. Biol. Chem., 272, 7421, 1997
k Nagata, S., Cell., 88, 355, 1997
l Harris, J. L., et. al., J. Biol. Chem., 273, 27364, 1998
m Cazzulo, J. J., Cazzulo Franke, M. C., Martinez, J. and Franke de Cazzulo, B. M., Biochim. Biophys. Acta., 1037, 186–191, 1990
n Cazzulo, J. J., Bravo, M., Raimondi, A., Engstrom, U., Lindeberg, G. and Hellman, U., Cell Mol. Biol., 42, 691–696, 1996
o Potempa, J., Dubin, A., Korzus, G. and Travis, J., Biochem. J., 263, 2664–2667, 1998
p Kembhavi, A. A., Buttle, D. J., Rauber, P. and Barrett, A. J., FEBS Lett., 283, 277–280, 1991
q Alves, L. C., et. al., Mol. Biochem. Parasitol, 116, 1–9, 2001.
r Guarné, et. al., J. Mol. Biol., 302, 1227–1240, 2000.
s Halfon and Craik,. (Barret, Rawlings and Woessner, eds.), in Handbook of Proteolytic Enzymes, Academic Press, London, 12–21, 1998.
t Sasaki, et. al., (1984), J. Biol. Chem., 259, 12489–12494, 1984.
u Bossard, M. J., et. al., J. Biol. Chem., 21, 12517–12524, 1996
v Santamaria, I., et. al., J. Biol. Chem., 273, 16816–16823, 1998
w Klemencic, J, et al., Eur. J. Biochem., 267, 5404–5412, 2000

*Trypanosoma cruzi* Cruzipain Peptidase Activity Assays

Wild-type cruzipain, derived from *Trypanosoma cruzi* Dm28 epimastigotes, was obtained from Dr. Julio Scharfstein (Instituto de Biofisica Carlos Chagas Filho, Universidade Federal do Rio de Janeiro, R10 de Janeiro, Brazil). Activity assays were carried out in 100 mM sodium phosphate, pH 6.75 containing 1 mM EDTA and 10 mM L-cysteine using 2.5 nM enzyme. Ac-Phe-Arg-AMC ($K_M^{app} \approx 12$ µM) and D-Val-Leu-Lys-AMC ($K_M^{app} \approx 4$ µM) were used as the substrates. Routinely, Ac-FR-AMC was used at a concentration equivalent to $K_M^{app}$ and D-Val-Leu-Lys-AMC was used at a concentration of 25 µM. The rate of conversion of substrate to product was derived from the slope of the increase in fluorescence monitored continuously over time.

*Leishmania mexicana* Cysteine Protease B (CPB) Peptidase Activity Assays

Wild-type recombinant CPB without the C-terminal extention (i.e. CPB2.8ΔCTE; Sanderson, S. J., et. al., *Biochem. J*, 347, 383–388, 2000) was obtained from Dr. Jeremy Mottram (Wellcome Centre for Molecular Parasitology, The Anderson College, University of Glasgow, Glasgow, U.K.). Activity assays were carried out in 100 mM sodium acetate; pH 5.5 containing 1 mM EDTA; 200 nM NaCl and 10 mM DTT (Alves, L. C., et. al., *Mol. Biochem. Parasitol,* 116, 1–9, 2001) using 0.25 nM enzyme. Pro-Phe-Arg-AMC ($K_M^{app} \approx 38$ µM) was used as the substrate at a concentration equivalent to $K_M^{app}$. The rate of conversion of substrate to product was derived from the slope of the increase in fluorescence monitored continuously over time.

Cathepsin Peptidase Activity Assays

Bovine cathepsin S, human cathepsin L, human cathepsin H and human cathepsin B were obtained from CN Biosciences. Recombinant human cathepsin S, human cathepsin K and human cathepsin X were obtained from Dr. Boris Turk (Josef Stefan Institute, Ljubljana, Slovenia). Unless otherwise stated, all peptidase activity assays were carried out in 10 mM bis-tris-propane (BTP), pH 6.5 containing 1 mM EDTA, 5 mM 2-mercaptoethanol and 1 mM $CaCl_2$. Human cathepsin H activity assays were carried out in 10 mM BTP pH 6.5, 142 mM $NaCl_2$, 1 mM $CaCl_2$, 1 mM EDTA, 1 mM DTT, 0.035 mM Zwittergent 3–16. Human cathepsin K assays were carried out in 100 mM sodium acetate; pH 5.5 containing 20 mM L-cysteine and 1 mM EDTA (Bossard, M. J., et. al., *J. Biol. Chem.,* 2, 12517–12524, 1996). Human cathepsin X assays were carried out in 100 mM sodium acetate; pH 5.5 containing 20 mM L-cysteine; 0.05% (w/v) Brij 35 and 1 mM EDTA (Santamaria, I., et. al., *J. Biol. Chem.,* 273, 16816–16823, 1998; Klemencic, J, et al., *Eur. J. Biochem.,* 267, 5404–5412, 2000). The final enzyme concentrations used in the assays were 0.5 nM bovine cathepsin S, 1 nM cathepsin L, 0.1 nM cathepsin B, 0.25 nM Cathepsin K; 1 nM cathepsin X and 10 nM cathepsin H. For the inhibition assays, the substrates used for cathepsin S, cathepsin L, cathepsin B, cathepsin K and cathepsin H were boc-Val-Leu-Lys-AMC ($K_M^{app} \approx 30$ µM, KMaPP 20 EM), Z-Phe-Arg-AMC ($K_M^{app} \approx 40$ µM), Z-Leu-Arg-AMC ($K_M^{app} \approx 2$ µM); Bz-Phe-Val-Arg-AMC ($K_M^{app} \approx 150$ µM) respectively. In each case the substrate concentration used in each assay was equivalent to the $K_M^{app}$. The rate of conversion of substrate to product was derived from the slope of the increase in fluorescence monitored continuously over time.

Trypsin Peptidase Activity Assays

Human pancreatic trypsin (iodination grade; CN Biosciences) activity assays were carried out in 10 mM HEPES, pH 8.0 containing 5 mM $CaCl_2$ using 0.1 nM trypsin. For the inhibition assays, Z-Gly-Gly-Arg-AMC ($K_M^{app} \approx 84$ µM) was used as the substrate at a concentration equivalent to $K_M^{app}$. The rate of conversion of substrate to product was derived from the slope of the increase in fluorescence monitored continuously over time.

Clostripain Peptidase Activity Assays

Clostripain (Sigma) activity assays were carried out in 10 mM BTP, pH 6.5 containing 1 mM EDTA, 5 mM 2-mercaptoethanol and 1 mM $CaCl_2$ using 0.3 nM enzyme. For the inhibition assays, Z-Gly-Gly-Arg-AMC ($K_M^{app} \approx 100$ µM was used as the substrate at a concentration equivalent to $K_M^{app}$. The rate of conversion of substrate to product was derived from the slope of the increase in fluorescence monitored continuously over time.

Calpain Peptidase Activity Assays

Calpain (human erythrocyte µ-calpain and porcine kidney m-calpain; CN Biosciences) activity assays were carried out in 10 mM HEPES, pH 7.5 containing 2 mM 2-mercaptoethanol and $CaCl_2$ using 25 nM of either enzyme (Sasaki, et. al., *J. Biol. Chem.,* 259, 12489–12494, 1984). For µ-calpain inhibition assays, the buffer contained 100 µM $CaCl_2$ and Abz-Ala-Asn-Leu-Gly-Arg-Pro-Ala-Leu-Tyr($NO_2$Asp-$NH_2$ ($K_M^{app} \approx 20$ μM; Incenta Limited) was used as the substrate. For m-calpain inhibition assays, the assay buffer contained 200 μM $CaCl_2$ and Abz-Lys-Leu-Cys(Bzl)-Phe-Ser-Lys-Gln-Tyr($NO_2$)-Asp-$NH_2$ ($K_M^{app} \approx 22$ μM; Incenta Limited) was used as the substrate. In both cases the substrate concentration employed in the assays was equivalent to the $K_M^{app}$. The rate of conversion of substrate to product was derived from the slope of the increase in fluorescence monitored continuously over time.

Extracellular *S. aureus* V8 Cysteine Peptidase (staphylopain) Peptidase Activity Assays

*S. aureus* V8 was obtained from Prof. S. Arvidson, Karolinska Institute, Stockholm, Sweden. Extracellular *S. aureus* V8 cysteine peptidase (staphylopain) activity assays were carried out using partially purified *S. aureus* V8 culture supernatant (obtained from Dr. Peter Lambert, Aston University, Birmingham, U.K.). Activity assays were carried out in 10 mM BTP, pH 6.5 containing 1 mM EDTA, 5 mM 2-mercaptoethanol and 1 mM $CaCl_2$ using two-times diluted partially purified extract. For the inhibition assays, Abz-Ile-Ala-Ala-Pro-Tyr($NO_2$)-Glu-$NH_2$ ($K_M^{app} \approx 117$ μM; Incenta Limited) was used as the substrate at a concentration equivalent to $K_M^{app}$. The rate of conversion of substrate to product was derived from the slope of the increase in fluorescence monitored continuously over time.

Foot-and-mouth Disease Leader Peptidase (FMDV-LP) Activity Assays

Recombinant wild-type FMDV-LP was obtained from Dr. Tim Skern (Institut für Medizinische Biochemie, Abteilung für Biochemie, Universtit Wien, Wien, Austria). Activity assays were carried out in 50 mM trisacetate, pH 8.4 containing 1 mM EDTA, 10 mM L-cysteine and 0.25% (w/v) CHAPS using 10 nM enzyme. For the inhibition assays, Abz-Arg-Lys-Leu-Lys-Gly-Ala-Gly-Ser-Tyr$NO_2$)-Glu-$NH_2$ ($K_M^{app} \approx 51$ μM, Incenta Limited) was used as the substrate at a concentration equivalent to $K_M^{app}$. The rate of conversion of substrate to product was derived from the slope of the increase in fluorescence monitored continuously over time.

Caspase Peptidase Activity Assays

Caspases 1–10 were obtained from CN Biosciences or BioVision Inc. (Mountain View, Calif., USA) and all assays were carried out in 50 mM HEPES; pH 7.2, 10% (v/v) glycerol, 0.1% (w/v) CHAPS, 142 mM NaCl, 1 mM EDTA, 5 mM dithiothreitol (DIT) using 0.1–1 U per assay. For caspase 1, Ac-Leu-Glu-His-Asp-AMC was used as the substrate; for caspase 2, Z-Val-Asp-Val-Ala-Asp-AFC was used as the substrate; for caspase 3, Ac-Asp-Glu-Val-Asp-AMC was used as the substrate; for caspase 4, Suc-Tyr-Val-Ala-Asp-AMC was used as the substrate; for caspase 5, Ac-Leu-Glu-His-Asp-AMC was used as the substrate; for caspase 6, Ac-Val-Glu-Ile-Asp-AMC was used as the substrate; for caspase 7, Ac-Asp-Glu-Val-Asp-AMC was used as the substrate; for caspase 8, Ac-Ile-Glu-Thr-Asp-AMC was used as the substrate; for caspase 9, Ac-Leu-Glu-His-Asp-AMC was used as the substrate; for caspase 10, Ac-Ile-Glu-Thr-Asp-AMC was used as the substrate (Nicholson, D. W. and Thomberry, N. A., *TIBS*, 2, 299–306, 1997; Stennicke, H. R. and Salvesen, G. S., *J. Biol. Chem.*, 272(41), 25719–25723, 1997; Talanian, R. V., et. al., *J. Biol. Chem.*, 272(15), 9677–9682, 1997; Wolf, B. B. and Green, D. R., *J. Biol. Chem.*, 274(29), 20049–20052, 1999). The rate of conversion of substrate to product was derived from the slope of the increase in fluorescence monitored continuously over time.

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93–128.).

$$v_i = \frac{V_{max}^{app} \cdot [S_o]}{[S_o] + K_M^{app}} \qquad (1)$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '$[S_o]$' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995.).

$$v_i = \frac{V_{max}^{app} \cdot [S]}{[S] + \{K_M^{app} \cdot ([I]/K_i)\}} \qquad (2)$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '$[S]$' is the initial substrate concentration, '$K_i$' is the apparent dissociation constant and '$[I]$' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102–105, 1982; Morrison, J. F. *Biochim. Biophys. Acta*, 185, 269–286, 1969; Stone, S. R. and Hofsteenge, *J. Biochemistry*, 25, 4622–4628, 1986).

$$v_i = \frac{F\{E_o - I_o - K_i^{app} + \sqrt{(E_o - I_o - K_i^{app})^2 + 4 \cdot K_i^{app} \cdot E_o}\}}{2} \qquad (3)$$

$$K_i^{app} = K_i(1 + [S_o]/K_M^{app}) \qquad (4)$$

In Equation 3 '$v_1$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '$[S_o]$' is the initial substrate concentration and '$K_M^{app}$' is the apparent macroscopic binding (Michaelis) constant for the substrate (Morrison, 1982).

The Second-order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., TIBS, 102–105, 1982; Tian, W. X. and Tsou, C. L., Biochemistry, 21, 1028–1032, 1982; Morrison, J. F. and Walsh, C. T., from Meister (Ed.), Advances in Enzmol., 61, 201–301, 1988; Tsou, C. L., from Meister (Ed.), Advances in Enzymol., 61, 381–436, 1988;). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \quad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '[$S_o$]' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \quad (6)$$

Compounds of the invention were tested by the above described assays and observed to exhibit cruzipain inhibitory activity or inhibitory activity against an alternative CA C1 cysteine protease with an in vitro Ki inhibitory constant of less than or equal to 100 μM. Exemplary inhibition data for a number of example compounds of the invention are given in table 2.

TABLE 2

Exemplary inhibition data (Ki expressed as μM).

| EXAMPLE N° | Cruzipain | Bovine Cathepsin S | Human Cathepsin L | Human Cathepsin K |
|---|---|---|---|---|
| 22 | <5 | >50 | >100 | >5 |
| 46 | >10 | >20 | >5 | <1 |
| 49 | >100 | >100 | <10 | >100 |
| 4 | >100 | <10 | >100 | >100 |

What is claimed is:
1. A compound according to general formula (I):

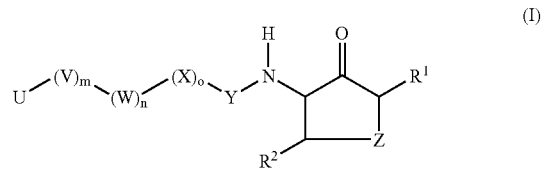

wherein: $R^1$=$C_{0-7}$-alkyl (when C=0, $R^1$ is hydrogen), $C_{3-6}$-cycloalkyl or Ar—$C_{0-7}$-alkyl (when C=0, $R^1$ is Ar);

$R^2$=$C_{1-7}$-alkyl, $C_{3-6}$-cycloalkyl or Ar—$C_{0-7}$-alkyl;

Y=CHR$^3$—CO or CR$^3$R$^4$—CO where $R^3$ and $R^4$ are independently chosen from $C_{0-7}$-alkyl, $C_{3-6}$-cycloalkyl and Ar—$C_{0-7}$-alkyl, or Y represents

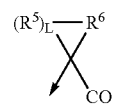

where L is a number from one to four and $R^5$ and $R^6$ are independently chosen from CR$^7$R$^8$ where $R^7$ and $R^8$ are independently chosen from $C_{0-7}$-alkyl, $C_{3-6}$-cycloalkyl, Ar—$C_{0-7}$-alkyl or halogen; and for each $R^5$ and $R^6$ either $R^7$ or $R^8$ (but not both $R^7$ and $R^8$) may additionally be chosen from O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N—($C_{0-7}$-alkyl)$_2$, N—($C_{3-6}$-cycloalkyl)$_2$, and N—(Ar—$C_{0-7}$-alkyl)$_2$;

in (X)$_o$ X=CR$^9$R$^{10}$, where $R^9$ and $R^{10}$ are independently chosen from $C_{0-7}$-alkyl, $C_{3-6}$-cycloalkyl and Ar—$C_{0-7}$-alkyl and o is a number from zero to three;

in (W)$_n$ W=O, S, C(O), S(O) or S(O)$_2$ or, when o is one or greater, NR$^{11}$, where $R^{11}$ is chosen from $C_{0-7}$-alkyl, $C_{3-6}$-cycloalkyl and Ar—$C_{0-7}$-alkyl and n is zero or one;

in (V)$_m$ V=C(O), C(S), S(O), S(O)$_2$, S(O)$_2$NH, OC(O), NHC(O), NHS(O)$_2$, OC(O)NH, C(O)NH or CR$^{12}$R$^{13}$, where $R^{12}$ and $R^{13}$ are independently chosen from $C_{0-7}$-alkyl, $C_{3-6}$-cycloalkyl, Ar—$C_{0-7}$-alkyl and m is a number from zero to three, provided that when m is greater than one, (V)$_m$ contains a maximum of one carbonyl or sulphonyl group;

Z=O (in which case compounds of general formula (I) may be named as (2-alkyl-4-oxo-tetrahydrofuran-3-yl) amides), S (in which case compounds of general formula (I) may be named as (2-alkyl-4-oxo-tetrahydrothiophen-3-yl)amides), or CH$_2$ (in which case compounds of general formula (I) may be named as (2-alkyl-5-oxocyclopentyl)amides);

U=a stable 5- to 7-membered monocyclic or a stable 8- to 11-membered bicyclic ring which is either saturated or unsaturated and which includes zero to four heteroatoms (as detailed below):

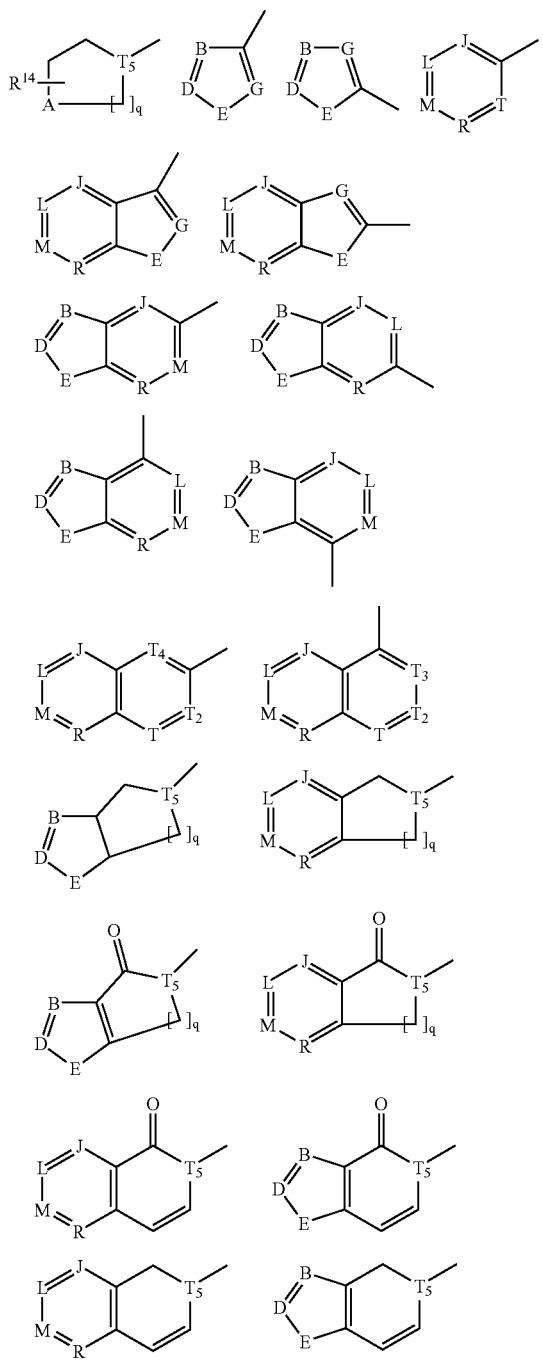

wherein $R^{14}$ is chosen from:
$C_{0-7}$-alkyl, $C_{3-6}$-cycloalkyl, Ar—$C_{0-7}$-alkyl, halogen, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N—($C_{0-7}$-alkyl)$_2$, N—($C_{3-6}$-cycloalkyl)$_2$ and N—(Ar—C0-7-alkyl)$_2$;

A is chosen from:
$CH_2$, $CHR^{14}$, O, S and $NR^{15}$, where $R^{14}$ as defined above and where $R^{15}$ is chosen from $C_{0-7}$-alkyl, $C_{3-6}$-cycloalkyl and Ar—$C_{0-7}$-alkyl;

B, D and G are independently chosen from:
$CR^{14}$, where $R^{14}$ is as defined above, or N;

E is chosen from:
$CH_2$, $CHR^{14}$, O, S and $NR^{15}$, where $R^{14}$ and $R^{15}$ are defined as above;

J, L, M, R, T, $T_2$, $T_3$ and $T_4$ are independently chosen from:
$CR^{14}$ and N, where $R^{14}$ as defined above;

$T_5$ is chosen from:
CH or, only when m+n+o≧1, $T_5$ may additionally be N;

q is a number from one to three, thereby defining a 5-, 6- or 7-membered ring.

provided that when Z is O or S and Y is $CHR^3CO$ (wherein $R^3$ is not hydrogen or unsubstituted $C_{0-7}$ alkyl):
either o=0, m=1 and V is not $CR^{12}R^{13}$;
or o=0, n=0, m=2 or 3 and the V group directly attached to the substituent Y is not $CR^{12}R^{13}$;

provided that when Z is O and Y is $CHR^3CO$:
either o=0, n≠0;
or o=0, n=0, m=1 and V is not OC(O)NH, $SO_2NH$ or C(O)NH;
or o=0, n=0, m=2 or 3 and the V group directly attached to the substituent Y is not OC(O)NH, $SO_2NH$ or C(O)NH.

2. A compound as claimed in claim 1, wherein $R^1$ comprises $C_{0-7}$-alkyl or Ar—$C_{0-7}$-alkyl.

3. A compound as claimed in claim 2, wherein $R^1$ is selected from hydrogen or one of the following moieties:

4. A compound as claimed in claim 1, wherein $R^2$ is $C_{1-7}$-alkyl or Ar—$C_{0-7}$-alkyl.

5. A compound as claimed in claim 4, wherein $R^2$ is selected from one of the following moieties:

wherein $R^{14}$ and $R^{15}$ are as defined previously.

6. A compound as claimed in claim 1 in which Z represents an oxygen atom.

7. A compound as claimed in claim 1, wherein Y is $CHR^4CO$ where $R^4$ is selected from $C_{0-7}$-alkyl or $Ar—C_{0-7}$-alkyl; or wherein Y comprises a group:

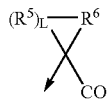

where $R^5$ and $R^6$ are each $CR^7R^8$ and each $R^7$ and $R^8$ is, independently, selected from $C_{0-7}$-alkyl or $Ar—C_{0-7}$-alkyl.

8. A compound as claimed in claim 1, wherein Y is $CHR^4CO$ where $R^4$ is selected from $C_{3-6}$-cycloalkyl.

9. A compound as claimed in claim 1, wherein Y is selected from one of the following moieties:

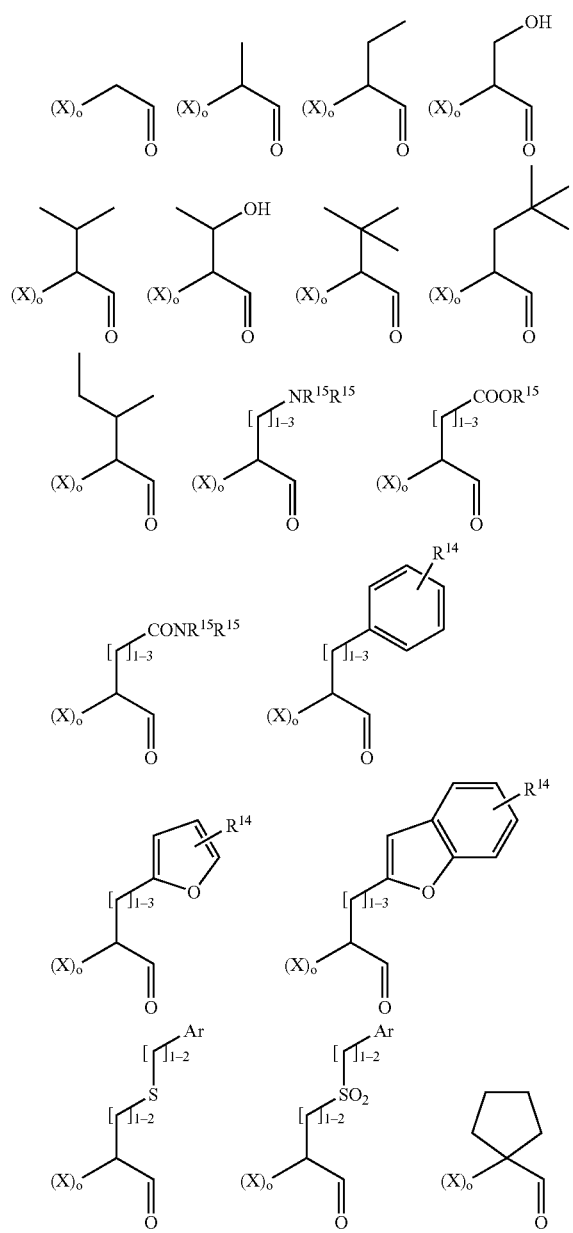

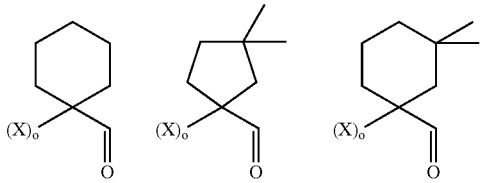

wherein $R^{14}$ and $R^{15}$ and Ar are as defined previously.

10. A compound as claimed in claim 1, wherein Y is $CHR^4CO$ where $R^4$ is $Ar—CH_2—$, where the aromatic ring is an optionally substituted phenyl or monocyclic heterocycle.

11. A compound as claimed in claim 1, wherein Y is $CHR^4CO$ where $R^4$ represents a simple branched alkyl group or a straight heteroalkyl chain.

12. A compound as claimed in claim 1, wherein Y is $CHR^4CO$ where the $R^4$ group comprises cyclohexylmethyl.

13. A compound as claimed in claim 1, wherein Y is selected from the following:

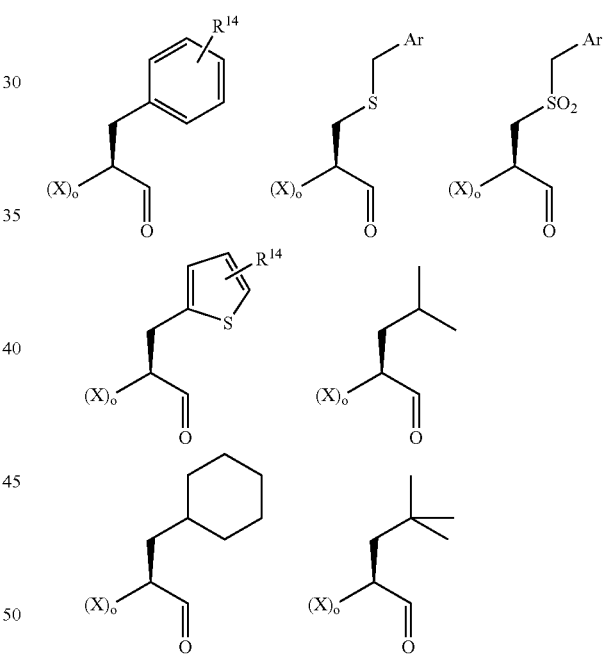

wherein $R^{14}$ and Ar are as defined previously.

14. A compound as claimed in claim 1 wherein, in the group $(X)_o$, X is $CR^8R^9$ and each of $R^9$ and $R^{10}$ is selected from $C_{0-7}$-alkyl or $Ar—C_{0-7}$-alkyl.

15. A compound as claimed in claim 1, wherein $(X)_o$ is one of the following moieties:

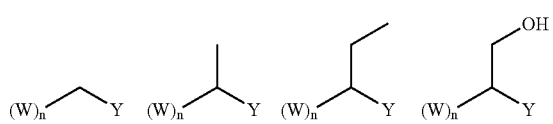

-continued

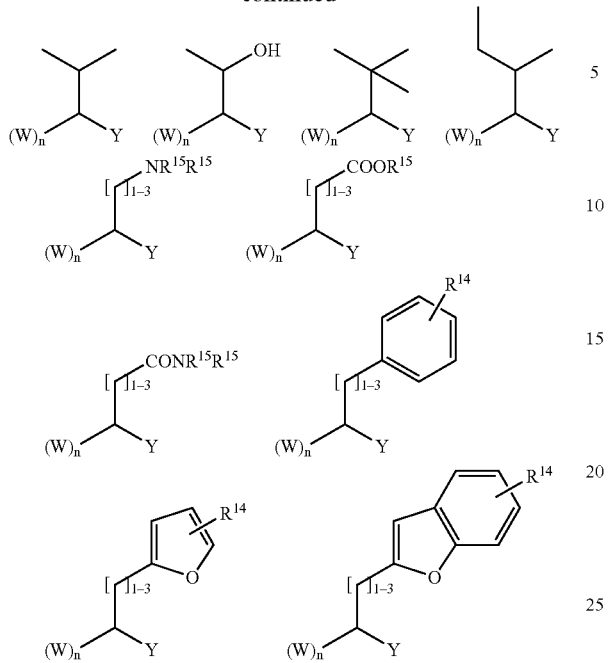

wherein $R^{14}$ and $R^{15}$ are as defined previously.

16. A compound as claimed in claim 1, wherein $(X)_o$ a simple alkyl group and where o=0 or 1.

17. A compound as claimed in claim 1 wherein, in the group $(W)_n$:
W is O, S, $SO_2$, SO, C(O) or when o is one or greater, $NR^{11}$, where $R^{11}$ is $C_{0-4}$-alkyl; and n is 0 or 1.

18. A compound as claimed in claim 1 wherein, in the group $(W)_n$:
W is O, S, $SO_2$, C(O) and n is 0 or 1.

19. A compound as claimed in claim 1 wherein, in the group $(V)_m$:
V is C(O), C(O)NH or $CHR^{13}$, where $R^{13}$ is $C_{0-4}$-alkyl; and
m is 0 or 1.

20. A compound as claimed in claim 1, wherein the combination $(V)_m$ and $(W)_m$ is one of the following:

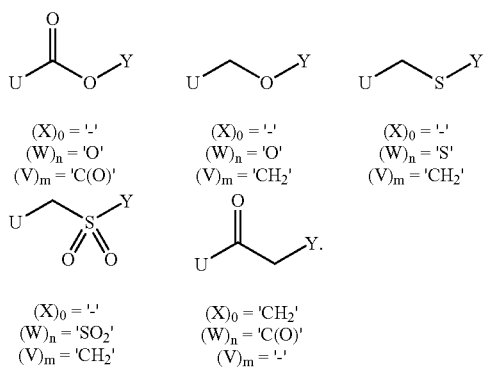

-continued

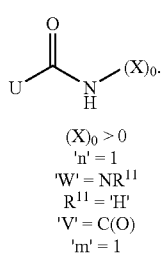

$(X)_0 > 0$
'n' = 1
'W' = $NR^{11}$
$R^{11}$ = 'H'
'V' = C(O)
'm' = 1

21. A compound as claimed in claim 1, wherein the combination $(X)_o$, $(V)_m$ and $(W)_m$ is one of the following:

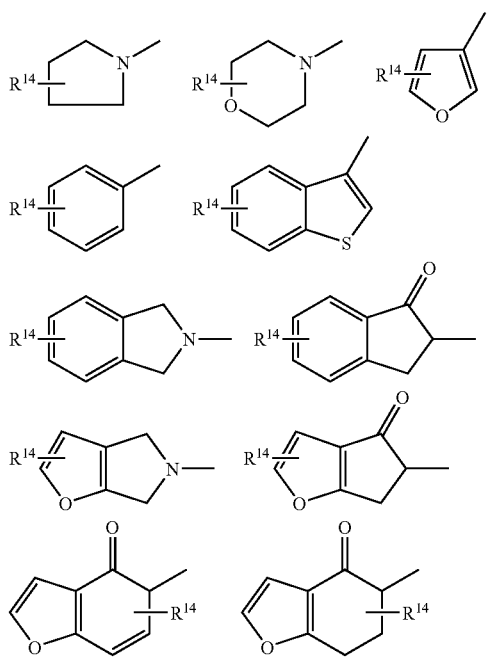

22. A compound as claimed in claim 1, wherein U comprises an optionally substituted 5- or 6-membered saturated or unsaturated heterocycle or an optionally substituted saturated or unsaturated 9- or 10-membered heterocycle.

23. A compound as claimed in claim 22, wherein U comprises one of the following:

-continued

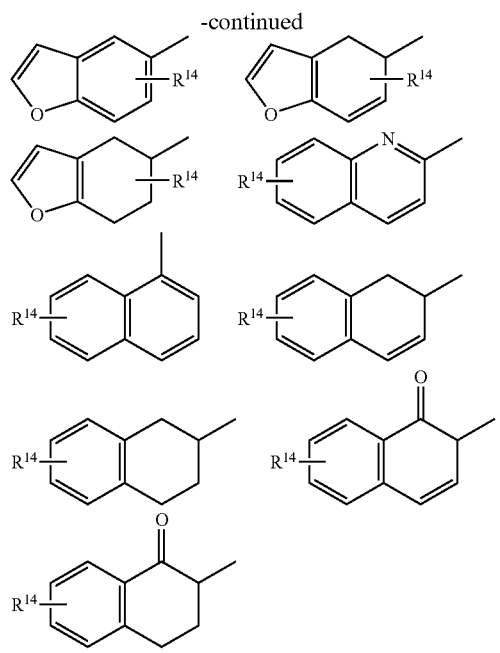

wherein R[14] is as defined previously.

24. A compound as claimed in claim 1, wherein U comprises a bulky alkyl or aryl group at the para position of an aryl Ar.

25. A compound as claimed in claim 1, wherein U comprises a meta or para-biaryl Ar—Ar, where Ar is as previously defined.

26. A compound as claimed in claim 1, wherein U comprises a 6,6 or 6,5 or 5,6-fused aromatic ring.

27. A compound as claimed in claim 1, wherein U represents a group:

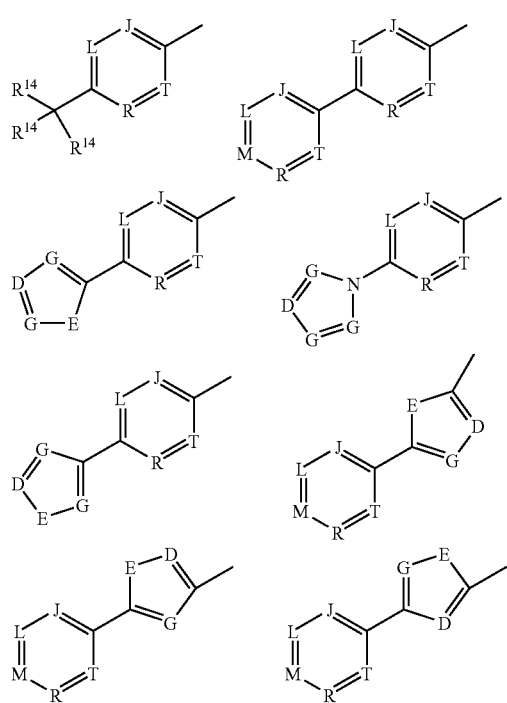

-continued

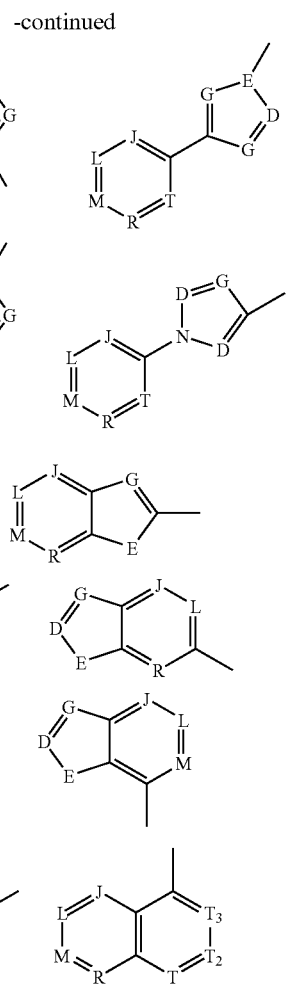

wherein R[14], D, E, G, J, L, M, R, T, $T_2$, $T_3$ and $T_4$ are as defined previously.

28. A compound as claimed in claim 1, wherein U represents a group

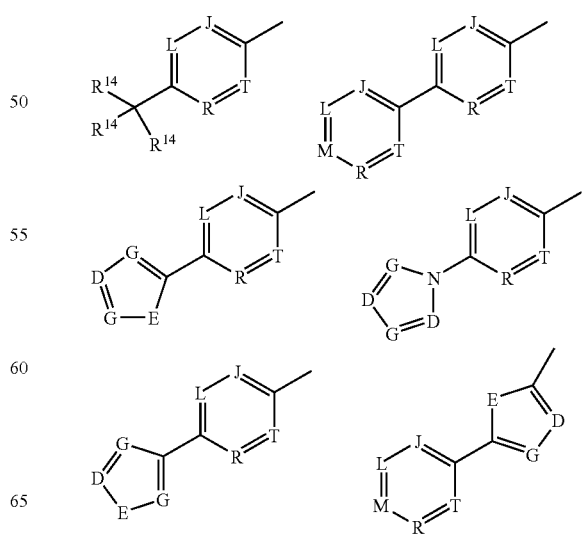

-continued

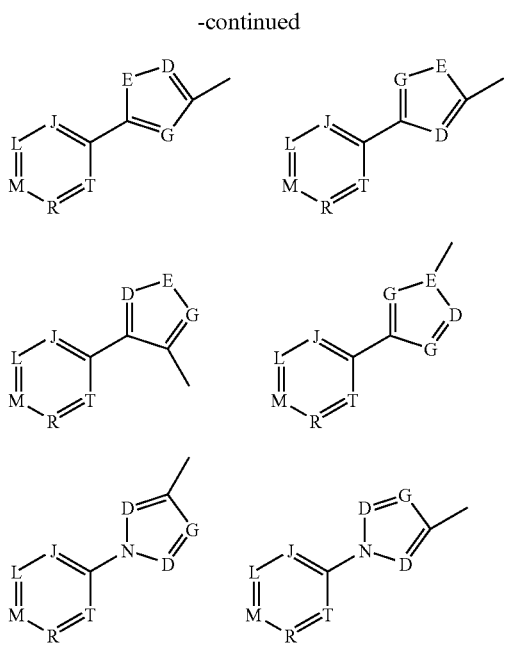

wherein R¹⁴, D, E, G, J, L, M, R and T are as defined previously.

29. A compound as claimed in claim 1, wherein U represents a group

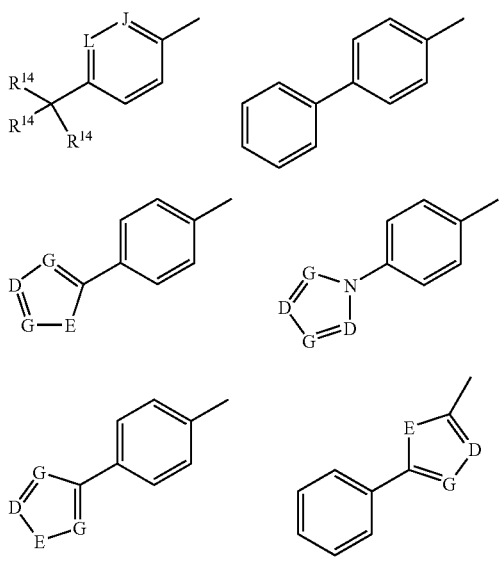

-continued

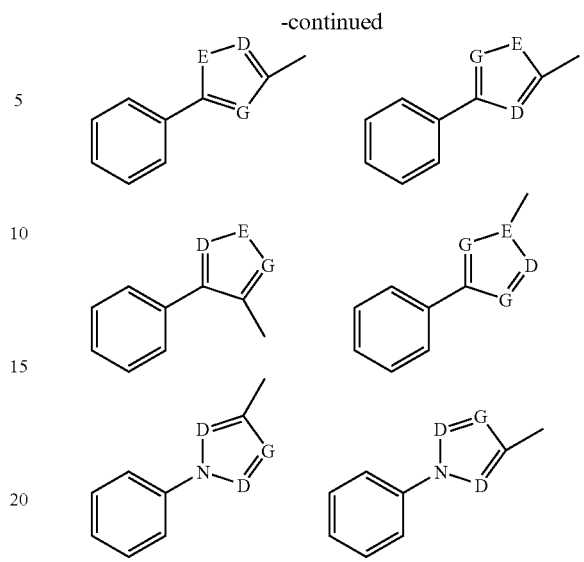

wherein $R^{14}$, D, E, G, J and L are as defined previously.

30. A method of validating a known or putative cysteine protease inhibitor as a therapeutic target, the method comprising:
   (a) assessing the in vitro binding of a compound as claimed in claim 1 to an isolated known or putative cysteine protease, providing a measure of 'potency'; and optionally, one or more of the steps of:
   (b) assessing the binding of a compound as claimed in claim 1 to closely related homologous proteases of the target and general house-keeping proteases (e.g. trypsin) to provides a measure of 'selectivity';
   (c) monitoring a cell-based functional marker of a particular cysteine protease activity, in the presence of a compound as claimed in any one of claim 1; and
   (d) monitoring an animal model-based functional marker of a particular cysteine protease activity, in the presence of a compound as claimed in claim 1.

31. The use of a compound as claimed in claim 1 in the validation of a known or putative cysteine protease inhibitor as a therapeutic target.

32. A compound as claimed in claim 1 for use in medicine, especially for preventing or treating diseases in which the disease pathology may be modified by inhibiting a cysteine protease.

33. A composition comprising one or more compounds as claimed in claim 1 and a pharmaceutically or veterinarily acceptable carrier.

34. A compound as claimed in claim 1 for preventing or treating Chagas' disease.

35. A method for preventing or treating Chagas' disease comprising administering an effective amount of one or more compounds of claim 1.

* * * * *